US011236372B2

(12) United States Patent
Wessel et al.

(10) Patent No.: US 11,236,372 B2
(45) Date of Patent: Feb. 1, 2022

(54) LIPID PRODUCTION

(71) Applicant: EVONIK OPERATIONS GMBH, Essen (DE)

(72) Inventors: Mirja Wessel, Bochum (DE); Steffen Schaffer, Herten (DE); Anne Jeremias, Wuppertal (DE); Martin Schilling, Bonn (DE); Hans Henning Wenk, Mülheim an der Ruhr (DE)

(73) Assignee: Evonik Operations GmbH, Essen (DE)

( * ) Notice: Subject to any disclaimer, the term of this patent is extended or adjusted under 35 U.S.C. 154(b) by 0 days.

(21) Appl. No.: 16/968,586

(22) PCT Filed: Feb. 8, 2019

(86) PCT No.: PCT/EP2019/053133

§ 371 (c)(1),
(2) Date: Aug. 8, 2020

(87) PCT Pub. No.: WO2019/154984

PCT Pub. Date: Aug. 15, 2019

(65) Prior Publication Data

US 2020/0407761 A1 Dec. 31, 2020

(30) Foreign Application Priority Data

Feb. 9, 2018 (EP) .................................... 18156045

(51) Int. Cl.

| | |
|---|---|
| ***C12N 15/52*** | (2006.01) |
| ***C12P 7/64*** | (2006.01) |
| ***C07K 14/195*** | (2006.01) |
| ***C11D 1/10*** | (2006.01) |
| ***C12N 9/10*** | (2006.01) |

(52) U.S. Cl.

CPC .......... *C12P 7/6445* (2013.01); *C07K 14/195* (2013.01); *C11D 1/10* (2013.01); *C12N 9/1051* (2013.01); *C12N 15/52* (2013.01)

(58) Field of Classification Search

CPC ...... C12P 7/6436; C07K 14/195; C12N 15/52
See application file for complete search history.

(56) References Cited

U.S. PATENT DOCUMENTS

| | | | |
|---|---|---|---|
| 10,174,353 | B2 | 1/2019 | Thum |
| 2018/0066297 | A1 | 3/2018 | Haas |
| 2018/0371504 | A1 | 12/2018 | Haas |
| 2020/0199492 | A1 | 6/2020 | Xue |

FOREIGN PATENT DOCUMENTS

| | | |
|---|---|---|
| WO | WO 2014/197457 | 12/2014 |

OTHER PUBLICATIONS

International Search Report for corresponding international application PCT/EP2019/053133, filed Feb. 8, 2019.
Written Opinion of the International Searching Authority for corresponding international application PCT/EP2019/053133, filed Feb. 8, 2019.
International Preliminary Report on Patentability for corresponding international application PCT/EP2019/053133, filed Feb. 8, 2019.
European Search Report and Search Opinion for corresponding European application EP 18 15 6045 filed Feb. 9, 2018.
Matsuyama, et al., "Surface-Active Novel Glycolipid and Linked 3-Hydroxy Fatty Acids Produced by *Serratia rubidaea*," *Journal of Bacteriology* 172(6):3015-3022 (Jun. 1990).
Uniprot: AXX16_0219-RhIB, TDP-rhamnosyltransferase 1-Serratia rubidaea, gene and protein (Jun. 2016).
U.S. Appl. No. 16/063,256, filed Jun. 16, 2018, US-2018/0371504 A1, Dec. 27, 2018, Haas.
U.S. Appl. No. 16/608,791, filed Oct. 25, 2019, US-2020/0199492 A1, Jun. 25, 2020, Xue.

*Primary Examiner* — Tekchand Saidha
(74) *Attorney, Agent, or Firm* — Law Office of Michael A. Sanzo, LLC

(57) ABSTRACT

The present invention relates to at least one cell for producing at least one lipid with general formula II from at least one carbon substrate, General Formula II $CH_2OH$ H H O O O COOH $R^1$ O $R^2$ OH OH OH wherein $R^1$ and $R^2$ independently of one another comprises identical or different organic radicals each with 5 to 13 carbon atoms,
wherein the cell is a non-pathogenic cell that is genetically modified to increase the heterologous expression relative to the wild type cell of:
- an enzyme ($E_2$) capable of converting 3-hydroxyalkanoyl-3-hydroxyalkanoyl-CoA/ACP or 3-(3-hydroxyalkanoyloxy)alkanoic acid (HAA) and NDP-glucose into β-D-glucopyranosyl-3-hydroxyalkanoyl-3-hydroxyalkanoate.

18 Claims, No Drawings

Specification includes a Sequence Listing.

LIPID PRODUCTION

CROSS REFERENCE TO RELATED APPLICATIONS

The present application is US national stage of international application PCT/EP2019/053133, which had an international filing date of Feb. 8, 2019, and which was published on Aug. 15, 2019. Priority is claimed to European application 18156045.9, filed on Feb. 9, 2018. The contents of these prior applications is hereby incorporated by reference in their entirety.

FIELD OF THE INVENTION

The present invention relates to a recombinant cell and a biotechnological method for producing lipids. In particular, the cell is a non-pathogenic cell genetically modified to produce at least one rubiwettin.

BACKGROUND OF THE INVENTION

Today, most of the available surfactants such as sodium laureth sulfate (SLES), betaine and the like are produced chemically at an industrial scale. These chemically produced surfactants have all the disadvantages that usually come with the use of a chemical production process such as the formation of harmful byproducts. For example, in the SLES production process, at least one harmful byproduct 1,4-dioxane is produced. In order to reduce the amount of toxic products generated and in view of consumers' increasing demand for environmentally friendly products, there is a general trend towards production and use of biosurfactants. Besides producing less poisonous byproducts during the manufacture process, biosurfactants also have useful properties like high structural diversity, beneficial surfactant properties, low environmental toxicity, antibiotic or bioactive properties and complete biological degradability. There is thus a general impetus towards producing and using biosurfactants instead of chemical surfactants.

Rubiwettins are at least one example of such a biosurfactant. Rubiwettins represent an economically interesting class of surfactants because they may potentially replace chemically produced surfactants.

Rubiwettins are exolipids composed of one β-D-glucose molecule linked to a 3-hydroxy fatty acid dimer with chain length $C_{14}$ and $C_{10}$ as lipid main components. They have surface-active properties. Rubiwettins are currently being synthesized by a wildtype *Serratia rubidaea* isolate which is a human- and animal pathogen. The fact that this production organism is able to cause diseases considerably reduces the customer acceptance for these conventionally produced rubiwettins. Further, higher safety requirements are also needed during the production process of rubiwettins and this increases the costs owing to increased capital expenditure and possibly additional production steps.

The current methods available for production of biosurfactants such as rubiwettins involve the use of these pathogenic organisms. The yield of production can be optimized by varying pH, oxygen supply, media composition, feeding strategies, nitrogen supply, temperature, choice of substrate and the like. However, if rubiwettins are to be employed on a large scale as surfactants they will have to compete with the currently employed surfactants. The latter are bulk chemicals, which can be produced at a very low cost. Therefore, rubiwettins must also be produced at costs as low as possible, without health risks for the customer and with defined properties as far as possible. This is not possible by merely optimizing the performance parameters via process optimization.

Accordingly, there is a need in the art for a cheaper and more efficient method of producing biosurfactants, for example rubiwettins with high product yields.

DESCRIPTION OF THE INVENTION

The present invention attempts to solve the problems above by providing a biotechnological means of producing biosurfactants such as lipids, in particular rubiwettins from a carbon source using a non-pathogenic cell. In particular, the non-pathogenic cell may be genetically modified to increase the expression of at least one enzyme ($E_2$) that is capable of converting an enzyme ($E_2$) capable of converting 3-hydroxyalkanoyl-3-hydroxyalkanoyl-CoA/ACP and/or 3-(3-hydroxyalkanoyloxy)alkanoic acid (HAA) in combination with NDP-glucose into β-D-glucopyranosyl-3-hydroxyalkanoyl-3-hydroxyalkanoate. The genetically modified cell may then be used to convert a suitable carbon source to a lipid with general formula II below:

General Formula II

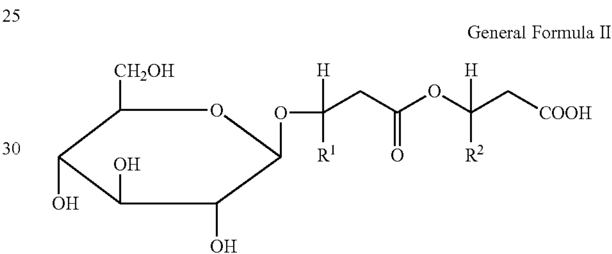

wherein $R^1$ and $R^2$ independently of one another is an identical or different alkyl group with 5 to 13 carbon atoms. In particular, the alkyl group may be saturated or unsaturated. More in particular, the alkyl group of $R^1$ and/or $R^2$ may be a monounsaturated alkyl radical. Even more in particular, $R^1$ and/or $R^2$ may be selected from the group consisting of pentenyl, heptenyl, nonenyl, undecenyl, tridecenyl and $(CH_2)_n$—$CH_3$ with n=4-12.

This lipid of General Formula II may also be known as a glycolipid and more particularly a rubiwettin RG1. The genetically modified cell according to any aspect of the present invention has the advantage of being non-pathogenic and simple to culture. This enables the cell to be safer for production and also keeps the costs lower as no special safety requirements are needed in the lab during production and use of the rubiwettin. The cells according to any aspect of the present invention has the further advantage of being able to use a variety of carbon substrates to produce the lipids according to any aspect of the present invention. For examples simple carbons such as glucose may be used as a carbon substrate. Also, the lipids formed according to any aspect of the present invention have defined and flexible properties. It is another advantage according to any aspect of the present invention that rubiwettins can be produced using a non-pathogenic cell. A further advantage is that rubiwettins can be produced with higher space-time yield, higher carbon yields, product concentration, product homogeneity (fatty acid species) than with cells without enhancement of these activities.

According to one aspect of the present invention, there is provided a microbial cell for producing at least one lipid with general formula II from at least one carbon substrate, General Formula II

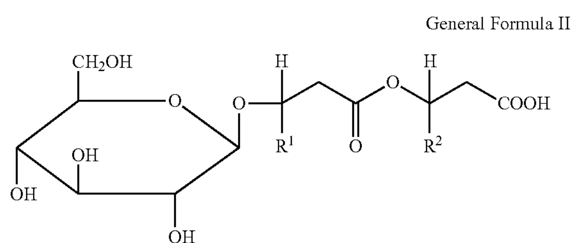

wherein $R^1$ and $R^2$ independently of one another is an identical or different alkyl group with 5 to 13 carbon atoms, and wherein the cell is a non-pathogenic cell that is genetically modified to increase the heterologous expression relative to the wild type cell of:

an enzyme ($E_2$) capable of converting 3-hydroxyalkanoyl-3-hydroxyalkanoyl-CoA/ACP and/or 3-(3-hydroxyalkanoyloxy)alkanoic acid (HAA) into β-D-glucopyranosyl-3-hydroxyalkanoyl-3-hydroxyalkanoate.

In particular, glucose may be added for either or both of the conversions to take place. Glucose may thus be added for the conversion of 3-hydroxyalkanoyl-3-hydroxyalkanoyl-CoA/ACP into β-D-glucopyranosyl-3-hydroxyalkanoyl-3-hydroxyalkanoate. In another example, glucose may be added for conversion of HAA into β-D-glucopyranosyl-3-hydroxyalkanoyl-3-hydroxyalkanoate. In another example, both HAA and 3-hydroxyalkanoyl-3-hydroxyalkanoyl-CoA/ACP may be present at the same time for β-D-glucopyranosyl-3-hydroxyalkanoyl-3-hydroxyalkanoate production.

The enzyme $E_2$ may be capable of converting 3-hydroxyalkanoyl-3-hydroxyalkanoyl-CoA/ACP into β-D-glucopyranosyl-3-hydroxyalkanoyl-3-hydroxyalkanoate. In one example, the enzyme $E_2$ may be capable of converting HAA into β-D-glucopyranosyl-3-hydroxyalkanoyl-3-hydroxyalkanoate. In yet another example, the enzyme $E_2$ may be capable of converting 3-hydroxyalkanoyl-3-hydroxyalkanoyl-CoA/ACP and HAA into β-D-glucopyranosyl-3-hydroxyalkanoyl-3-hydroxyalkanoate. In all these examples, NDP-glucose may be present particularly to include the glucose moiety in General Formula II. The enzyme $E_2$ may be a glycosyltransferase (EC 2.4). In particular, the enzyme $E_2$ comprises SEQ ID NO: 4 or variant thereof. The term "variant", as used herein, comprises amino acid or nucleic acid sequences, respectively, that are at least 60, 65, 70, 75, 80, 85, 90, 92, 94, 95, 96, 97, 98 or 99% identical to the reference amino acid or nucleic acid sequence, wherein preferably amino acids other than those essential for the function, for example the catalytic activity of a protein, or the fold or structure of a molecule are deleted, substituted or replaced by insertions or essential amino acids are replaced in a conservative manner to the effect that the biological activity of the reference sequence or a molecule derived therefrom is preserved. The state of the art comprises algorithms that may be used to align two given nucleic acid or amino acid sequences and to calculate the degree of identity, see Arthur Lesk (2008), Thompson et al., 1994, and Katoh et al., 2005. The term "variant" is used synonymously and interchangeably with the term "homologue". Such variants may be prepared by introducing deletions, insertions or substitutions in amino acid or nucleic acid sequences as well as fusions comprising such macromolecules or variants thereof. In one example, the term "variant", with regard to amino acid sequence, comprises, in addition to the above sequence identity, amino acid sequences that comprise one or more conservative amino acid changes with respect to the respective reference or wild type sequence or comprises nucleic acid sequences encoding amino acid sequences that comprise one or more conservative amino acid changes. In one example, the term "variant" of an amino acid sequence or nucleic acid sequence comprises, in addition to the above degree of sequence identity, any active portion and/or fragment of the amino acid sequence or nucleic acid sequence, respectively, or any nucleic acid sequence encoding an active portion and/or fragment of an amino acid sequence. The term "active portion", as used herein, refers to an amino acid sequence or a nucleic acid sequence, which is less than the full length amino acid sequence or codes for less than the full length amino acid sequence, respectively, wherein the amino acid sequence or the amino acid sequence encoded, respectively retains at least some of its essential biological activity. For example an active portion and/or fragment of a protease may be capable of hydrolysing peptide bonds in polypeptides. The phrase "retains at least some of its essential biological activity", as used herein, means that the amino acid sequence in question has a biological activity exceeding and distinct from the background activity and the kinetic parameters characterising said activity, more specifically $k_{cat}$ and $K_M$, are preferably within 3, 2, or 1 order of magnitude of the values displayed by the reference molecule with respect to a specific substrate. Similarly, the term "variant" of a nucleic acid comprises nucleic acids the complementary strand of which hybridises, preferably under stringent conditions, to the reference or wild type nucleic acid. In one example, the variant of SEQ ID: 4 may have 60% sequence identity to SEQ ID NO:4.

In one example, the enzyme $E_2$ may have polypeptide sequence SEQ ID NO: 4 or a polypeptide sequence in which up to 25%, preferably up to 20%, particularly preferably up to 15% in particular up to 10, 9, 8, 7, 6, 5, 4, 3, 2, 1% of the amino acid radicals are modified compared to the reference sequence SEQ ID NO: 4 by deletion, insertion, substitution or a combination thereof and that still has at least 10%, preferably 50%, particularly preferably 80%, in particular more than 90% of the enzymatic activity of the enzyme having the reference sequence SEQ ID NO: 4, wherein enzymatic activity for an enzyme $E_2$ is understood as meaning the ability preferably to convert 3-hydroxyalkanoyl-3-hydroxyalkanoyl-CoA/ACP or 3-(3-hydroxyalkanoyloxy) alkanoic acid (HAA) into β-D-glucopyranosyl-3-hydroxyalkanoyl-3-hydroxyalkanoate. NDP-glucose may be present in this conversion.

The lipid of general formula II may also be called a rubiwettin. The length of the $R^1$ and $R^2$ group can be of varying lengths. In particular, $R^1$ and $R^2$ may be independently selected from the group consisting of saturated and unsaturated alkyls. More in particular, $R^1$ and/or $R^2$ may be a saturated or unsaturated alkyl group with 5 to 13 carbon atoms. Even more in particular, $R^1$ and $R^2$ may be a saturated or monounsaturated alkyl group with 5 to 13 carbon atoms. The $R^1$ and $R^2$ alkyl groups may comprise 5 to 13 carbon atoms, 7 to 13 carbon atoms, 9 to 13 carbon atoms, 5 to 11 carbon atoms, 5 to 9 carbon atoms and the like. In the examples where $R^1$ and/or $R^2$ alkyl group is a saturated alkyl group, the alkyl group may comprising 5, 6, 7, 8, 9, 10, 11, 12 or 13 carbon atoms. In the examples where $R^1$ and/or $R^2$ alkyl group is an unsaturated alkyl group, the alkyl group may be a monounsaturated alkyl comprising 5:1, 6:1, 7:1, 8:1, 9:1, 10:1, 11:1, 12:1, or 13:1 carbon atoms. The cell according to any aspect of the present invention may be able to produce a mixture of rubiwettins with varying $R^1$ and $R^2$ groups. In one example, the lipid of general formula II produced according to any aspect of the present invention may be a rubiwettin RG1 (CAS-Nr. 129039-46-9). The rubiwettin RG1 may also be called a glycolipid named β-D-Glucopyranosyl-3-(3'-hydroxytetradecanoyloxy)decanoate or β-Glucopyranosyl-3-(3'-hydroxytetradecanoyloxy)decanoate.

The cell according to any aspect of the present invention may be further genetically modified to increase the heterologous expression relative to the wild type cell of:

- an enzyme ($E_1$) capable of converting 3-hydroxyalkanoyl-CoA/ACP into 3-hydroxyalkanoyl-3-hydroxyalkanoyl-CoA/ACP and further to 3-(3-hydroxyalkanoyloxy)alkanoic acid (HAA).

The enzyme $E_1$ may be a 3-(3-hydroxyalkanoyloxy)alkanoic acid (HAA) synthase. In one example, the enzyme $E_1$ comprises SEQ ID NO: 2 or variant thereof. In another example, the enzyme $E_1$ comprises a sequence selected from the group consisting of SEQ ID NO: 6, SEQ ID NO: 8, SEQ ID NO: 10, SEQ ID NO: 12, SEQ ID NO: 14 and variants thereof, wherein the variant comprises 60% sequence identity to SEQ ID NO: 6, SEQ ID NO: 8, SEQ ID NO: 10, SEQ ID NO: 12 and SEQ ID NO: 14 respectively.

In one example, the enzyme $E_1$ may have polypeptide sequence SEQ ID NO: 6 or a polypeptide sequence in which up to 25%, preferably up to 20%, particularly preferably up to 15% in particular up to 10, 9, 8, 7, 6, 5, 4, 3, 2, 1% of the amino acid radicals are modified compared to the reference sequence SEQ ID NO: 6 by deletion, insertion, substitution or a combination thereof and that still has at least 10%, preferably 50%, particularly preferably 80%, in particular more than 90% of the enzymatic activity of the enzyme having the reference sequence SEQ ID NO: 6, wherein enzymatic activity for an enzyme $E_1$ is understood as meaning the ability preferably to convert 3-hydroxyalkanoyl-CoA/ACP into 3-hydroxyalkanoyl-3-hydroxyalkanoyl-CoA/ACP and further to HAA.

In another example, the enzyme $E_1$ may have polypeptide sequence SEQ ID NO: 8 or a polypeptide sequence in which up to 25%, preferably up to 20%, particularly preferably up to 15% in particular up to 10, 9, 8, 7, 6, 5, 4, 3, 2, 1% of the amino acid radicals are modified compared to the reference sequence SEQ ID NO: 8 by deletion, insertion, substitution or a combination thereof and that still has at least 10%, preferably 50%, particularly preferably 80%, in particular more than 90% of the enzymatic activity of the enzyme having the reference sequence SEQ ID NO: 8, wherein enzymatic activity for an enzyme $E_1$ is understood as meaning the ability preferably to convert 3-hydroxyalkanoyl-CoA/ACP into 3-hydroxyalkanoyl-3-hydroxyalkanoyl-CoA/ACP and further to 3-(3-hydroxyalkanoyloxy)alkanoic acid (HAA).

In a further example, the enzyme $E_1$ may have polypeptide sequence SEQ ID NO: 10 or a polypeptide sequence in which up to 25%, preferably up to 20%, particularly preferably up to 15% in particular up to 10, 9, 8, 7, 6, 5, 4, 3, 2, 1% of the amino acid radicals are modified compared to the reference sequence SEQ ID NO: 10 by deletion, insertion, substitution or a combination thereof and that still has at least 10%, preferably 50%, particularly preferably 80%, in particular more than 90% of the enzymatic activity of the enzyme having the reference sequence SEQ ID NO: 10, wherein enzymatic activity for an enzyme $E_1$ is understood as meaning the ability preferably to convert 3-hydroxyalkanoyl-CoA/ACP into 3-hydroxyalkanoyl-3-hydroxyalkanoyl-CoA/ACP and further to 3-(3-hydroxyalkanoyloxy) alkanoic acid (HAA).

In yet another example, the enzyme $E_1$ may have polypeptide sequence SEQ ID NO: 12 or a polypeptide sequence in which up to 25%, preferably up to 20%, particularly preferably up to 15% in particular up to 10, 9, 8, 7, 6, 5, 4, 3, 2, 1% of the amino acid radicals are modified compared to the reference sequence SEQ ID NO: 12 by deletion, insertion, substitution or a combination thereof and that still has at least 10%, preferably 50%, particularly preferably 80%, in particular more than 90% of the enzymatic activity of the enzyme having the reference sequence SEQ ID NO: 12, wherein enzymatic activity for an enzyme $E_1$ is understood as meaning the ability preferably to convert 3-hydroxyalkanoyl-CoA/ACP into 3-hydroxyalkanoyl-3-hydroxyalkanoyl-CoA/ACP and further to 3-(3-hydroxyalkanoyloxy)alkanoic acid (HAA).

In one other example, the enzyme $E_1$ may have polypeptide sequence SEQ ID NO: 14 or a polypeptide sequence in which up to 25%, preferably up to 20%, particularly preferably up to 15% in particular up to 10, 9, 8, 7, 6, 5, 4, 3, 2, 1% of the amino acid radicals are modified compared to the reference sequence SEQ ID NO: 14 by deletion, insertion, substitution or a combination thereof and that still has at least 10%, preferably 50%, particularly preferably 80%, in particular more than 90% of the enzymatic activity of the enzyme having the reference sequence SEQ ID NO: 14, wherein enzymatic activity for an enzyme $E_1$ is understood as meaning the ability preferably to convert 3-hydroxyalkanoyl-CoA/ACP into 3-hydroxyalkanoyl-3-hydroxyalkanoyl-CoA/ACP and further to 3-(3-hydroxyalkanoyloxy) alkanoic acid (HAA).

The cell according to any aspect of the present invention may produce a further lipid with general formula I from a carbon substrate, General Formula I

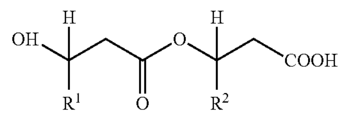

wherein $R^1$ and $R^2$ independently of one another is an identical or different alkyl group with 5 to 13 carbon atoms. In particular, the alkyl group may be saturated or unsaturated. More in particular, the alkyl group of $R^1$ and/or $R^2$ may be a monounsaturated alkyl radical. Even more in particular, $R^1$ and/or $R^2$ may be selected from the group consisting of pentenyl, heptenyl, nonenyl, undecenyl, tridecenyl and $(CH_2)_n$—$CH_3$ with n=4-12.

The lipid of general formula I may have $R^1$ and $R^2$ groups of varying lengths. In particular, $R^1$ and $R^2$ may be independently selected from the group consisting of saturated and unsaturated alkyls. More in particular, $R^1$ and/or $R^2$ may be a saturated or unsaturated alkyl group with 5 to 13 carbon atoms. Even more in particular, $R^1$ and $R^2$ may be a saturated or monounsaturated alkyl group with 5 to 13 carbon atoms. The $R^1$ and $R^2$ alkyl groups may comprise 5 to 13 carbon atoms, 7 to 13 carbon atoms, 9 to 13 carbon atoms, 5 to 11 carbon atoms, 5 to 9 carbon atoms and the like. In the examples where $R^1$ and/or $R^2$ alkyl group is an unsaturated alkyl group, the alkyl group may be a monounsaturated alkyl comprising 5:1, 6:1, 7:1, 8:1, 9:1, 10:1, 11:1, 12:1, or 13:1 carbon atoms. In the examples where $R^1$ and/or $R^2$ alkyl group is a saturated alkyl group, the alkyl group may comprising 5, 6, 7, 8, 9, 10, 11, 12 or 13 carbon atoms. The cell according to any aspect of the present invention may be able to produce a mixture of lipids with varying $R^1$ and $R^2$ groups. In particular, the lipid with formula I may also be called a rubiwettin R1 (CAS-Nr. 129039-45-8). In particular, the lipid is a mixture of 3-(3'-hydroxytetradecanoyloxy) tetradecanoate, 3-(3'-hydroxydecanoyloxy)decanoate, 3-(3'-hydroxyhexadecenoyloxy)hexadecenoate, 3-(3'-hydroxytetradecanoyloxy)decanoate, 3-(3'-hydroxyhexadecenoyloxy) decanoate, 3-(3'-hydroxyhexadecenoyloxy)tetradecanoate and minor molecular isomers.

Surprisingly, it could be shown that recombinant cells according to any aspect of the present invention with increased expression of $E_2$ and/or $E_1$ are able to produce increased amounts of lipids with the formulas II and/or I compared to the wildtype of the cell. The cells according to any aspect of the present invention may thus allow for high selective production of rubiwettins RG1 with reduced production of undesirable intermediates like dimers of β-hydroxy fatty acids.

The phrase "increased heterologous expression of an enzyme", as used herein is to be understood as increased intracellular activity. Basically, an increase in enzymatic activity can be achieved by increasing the copy number of the gene sequence or gene sequences that code for the enzyme, using a strong promoter or employing a gene or allele that codes for a corresponding enzyme with increased activity and optionally by combining these measures. Genetically modified cells used in the method according to the invention are for example produced by transformation, transduction, conjugation or a combination of these methods with a vector that contains the desired gene, an allele of this gene or parts thereof and a vector that makes expression of the gene possible. Heterologous expression is in particular achieved by integration of the gene or of the alleles in the chromosome of the cell or an extrachromosomally replicating vector. In particular, an increase in an activity of an enzyme relative to the wild type cell may be a 10, 15, 20, 25, 30, 35, 40, 45, 50, 55, 60, 65, 70, 75, 80, 85, 90, 95 or 100% more than the wild type cell.

A skilled person would be able to use any method known in the art to genetically modify a cell. Whether or not a nucleic acid molecule, polypeptide, more specifically an enzyme used according to any aspect of the present invention, is recombinant or not has not necessarily implications for the level of its expression. However, in one example one or more recombinant nucleic acid molecules, polypeptides or enzymes used according to any aspect of the present invention may be overexpressed. The term "overexpressed", as used herein, means that the respective polypeptide encoded or expressed is expressed at a level higher or at higher activity than would normally be found in the cell under identical conditions in the absence of genetic modifications carried out to increase the expression, for example in the respective wild type cell. The person skilled in the art is familiar with numerous ways to bring about overexpression. For example, the nucleic acid molecule to be overexpressed or encoding the polypeptide or enzyme to be overexpressed may be placed under the control of a strong inducible promoter such as the lac promoter. The state of the art describes standard plasmids that may be used for this purpose, for example the pET system of vectors exemplified by pET-3a (commercially available from Novagen). Whether or not a nucleic acid or polypeptide is overexpressed may be determined by way of quantitative PCR reaction in the case of a nucleic acid molecule, SDS polyacrylamide electrophoreses, Western blotting or comparative activity assays in the case of a polypeptide. Genetic modifications may be directed to transcriptional, translational, and/or post-translational modifications that result in a change of enzyme activity and/or selectivity under selected and/or identified culture conditions. Thus, in various examples of the present invention, to function more efficiently, a microorganism may comprise one or more gene deletions. Gene deletions may be accomplished by mutational gene deletion approaches, and/or starting with a mutant strain having reduced or no expression of one or more of these enzymes, and/or other methods known to those skilled in the art.

DE-A-100 31 999 gives a general survey of the possibilities for increasing the enzyme activity in cells as exemplified by pyruvate carboxylase, which is inserted hereby as a reference and whose disclosure content with respect to the possibilities for increasing the enzyme activity in cells forms a part of the disclosure of the present invention.

The expression of the above and all subsequently mentioned enzymes or genes is detectable with the aid of 1- and 2-dimensional protein gel separation and subsequent optical identification of the protein concentration in the gel using appropriate analytical software. If the increase in an enzyme activity is based exclusively on an increase in the expression of the corresponding gene, the quantification of the increase in the enzyme activity can be determined in a simple manner by a comparison of the 1- or 2-dimensional protein separations between wild-type and genetically modified cell. A customary method for the preparation of the protein gels in the case of coryneforme bacteria and for the identification of the proteins is the procedure described by Hermann et al. (Electrophoresis, 22: 1712.23 (2001)). The protein concentration can likewise be analyzed by Western Blot hybridization using an antibody specific for the protein to be detected (Sambrook et al., Molecular Cloning: a laboratory manual, 2nd Ed. Cold Spring Harbor Laboratory Press, Cold Spring Harbor, N.Y. USA, 1989) and subsequent optical analysis using appropriate software for the concentration determination (Lohaus and Meyer (1989) Biospektrum, 5: 32-39; Lottspeich (1999) Angewandte Chemie 111: 2630-2647). The activity of DNA-binding proteins can be measured by means of DNA band shift assays (also called gel retardation) (Wilson et al. (2001) Journal of Bacteriology, 183: 2151-2155). The action of DNA-binding proteins on the expression of other genes can be detected by various well-described methods of the reporter gene assay (Sambrook et al., Molecular Cloning: a laboratory manual, 2nd Ed. Cold Spring Harbor Laboratory Press, Cold Spring Harbor, N.Y. USA, 1989). The intracellular enzymatic activities can be determined according to various described methods (Donahue et al. (2000) Journal of Bacteriology 182 (19): 5624-5627; Ray et al. (2000) Journal of Bacteriology 182 (8): 2277-2284; Freedberg et al. (1973) Journal of Bacteriology 115 (3): 816-823). If in the following embodiments no practical methods are indicated for the determination of the activity of a certain enzyme, the determination of the increase in the enzyme activity and also the determination of the decrease of an enzyme activity preferably take place by means of the methods described in Hermann et al., Electophoresis, 22: 1712-23 (2001), Lohaus et al., Biospektrum 5 32-39 (1998), Lottspeich, Angewandte Chemie 111: 2630-2647 (1999) and Wilson et al., Journal of Bacteriology 183: 2151-2155 (2001).

If the increase in the enzyme activity is accomplished by mutation of the endogenous gene, such mutations can be randomly produced either by conventional methods, such as, for example, by UV irradiation or by mutagenic chemicals, or selectively by means of genetic engineering methods such as deletion(s), insertion(s) and/or nucleotide exchange(s).

Modified cells are obtained by these mutations. Particularly preferred mutants of enzymes are in particular also those enzymes that are no longer feedback-, product- or substrate-inhibitable or are so to a reduced degree at least in comparison to the wild-type enzyme.

If the increase in the enzyme activity is accomplished by increase in the synthesis of an enzyme, the copy number of the corresponding genes is increased or the promoter and regulation region or the ribosome binding site, which is situated upstream of the structural gene, is mutated. Expression cassettes, which are incorporated upstream of the structural gene, act in the same manner. It is additionally possible, by means of inducible promoters, to increase the expression at any desired point in time. In addition, however, also "enhancers" can be assigned to the enzyme gene as regulatory sequences, which likewise bring about increased gene expression by means of an improved interaction between RNA polymerase and DNA. As a result of measures for the prolongation of the lifetime of the mRNA, the expression is likewise improved. Furthermore, by prevention of the degradation of the enzyme protein the enzyme activity is likewise increased. The genes or gene constructs are present here either in plasmids having a different copy number or are integrated and amplified in the chromosome. Alternatively, an overexpression of the genes concerned can furthermore be achieved by modification of the media composition and culture management. The person skilled in the art finds directions for this, inter alia, in Martin et al. (Bio/Technology 5, 137-146 (1987)), in Guerrero et al. (Genes 138, 35-41 (1994)), Tsuchiya and Morinaga (Bio/Technology 6, 428-430 (1988)), in Eikmanns et al. (Genes 102, 93-98 (1991)), in EP-A-0 472 869, in U.S. Pat. No. 4,601,893, in Schwarzer and Pühler (Bio/Technology 9, 84-87 (1991)), in Reinscheid et al. (Applied and Environmental Microbiology 60, 126-132 (1994)), in LaBarre et al. (Journal of Bacteriology 175, 1001-1007 (1993)), in WO-A-96/15246, in Malumbres et al. (Genes 134, 15-24 (1993)), in JP-A-10-229891, in Jensen and Hammer (Biotechnology and Bioengineering 58, 191-195 (1998)) and in known textbooks of genetics and molecular biology. The measures described above likewise lead, like the mutations, to genetically modified cells.

Episomal plasmids, for example, are employed for increasing the expression of the respective genes. Suitable plasmids or vectors are in principle all embodiments available for this purpose to the person skilled in the art. Such plasmids and vectors can be taken, for example, from the brochures of the companies Novagen, Promega, New England Biolabs, Clontech or Gibco BRL. Further preferred plasmids and vectors can be found in: Glover, D. M. (1985) DNA cloning: a practical approach, Vol. I-III, IRL Press Ltd., Oxford; Rodriguez, R. L. and Denhardt, D. T (eds) (1988) Vectors: a survey of molecular cloning vectors and their uses, 179-204, Butterworth, Stoneham; Goeddel, D. V. (1990) Systems for heterologous gene expression, Methods Enzymol. 185, 3-7; Sambrook, J.; Fritsch, E. F. and Maniatis, T. (1989), Molecular cloning: a laboratory manual, 2nd ed., Cold Spring Harbor Laboratory Press, New York.

The plasmid vector, which contains the gene to be amplified, is then converted to the desired strain by conjugation or transformation. The method of conjugation is described, for example, in Schäfer et al., Applied and Environmental Microbiology 60: 756-759 (1994). Methods for transformation are described, for example, in Thierbach et al., Applied Microbiology and Biotechnology 29: 356-362 (1988), Dunican and Shivnan, Bio/Technology 7: 1067-1070 (1989) and Tauch et al., FEMS Microbiology Let-ters 123: 343-347 (1994). After homologous recombination by means of a "cross-over" event, the resulting strain contains at least two copies of the gene concerned.

According to any aspect of the present invention, the cell may be genetically modified so that in a defined time interval, within 2 hours, in particular within 8 hours or 24 hours, it forms at least twice, especially at least 10 times, at least 100 times, at least 1000 times or at least 10000 times more lipids of the general Formula I or II than the wild-type cell. The increase in product formation can be determined for example by cultivating the cell according to any aspect of the present invention and the wild-type cell each separately under the same conditions (same cell density, same nutrient medium, same culture conditions) for a specified time interval in a suitable nutrient medium and then determining the amount of target product (lipid with general formula II or I) in the nutrient medium.

Changes of amino acid residues of a given polypeptide sequence, which lead to no significant changes in the properties and function of the given polypeptide, are known to the person skilled in the art. Thus, for example, "conserved amino acids" can be mutually exchanged; examples of such suitable amino acid substitutions are: Ala for Ser; Arg for Lys; Asn for Gln or His; Asp for Glu; Cys for Ser; Gln for Asn; Glu for Asp; Gly for Pro; His for Asn or Gln; Ile for Leu or Val; Leu for Met or Val; Lys for Arg or Gln or Glu; Met for Leu or Ile; Phe for Met or Leu or Tyr; Ser for Thr; Thr for Ser; Trp for Tyr; Tyr for Trp or Phe; Val for Ile or Leu. It is likewise known that changes, particularly at the N- or C-terminus of a polypeptide, in the form of, for example, amino acid insertions or deletions often exert no significant influence on the function of the polypeptide.

The activity of an enzyme can be determined by disrupting cells which contain this activity in a manner known to the person skilled in the art, for example with the aid of a ball mill, a French press or of an ultrasonic disintegrator and subsequently separating off cells, cell debris and disruption aids, such as, for example, glass beads, by centrifugation for 10 minutes at 13,000 rpm and 4° C. Using the resulting cell-free crude extract, enzyme assays with subsequent LC-ESI-MS detection of the products can then be carried out. Alternatively, the enzyme can be enriched in the manner known to the person skilled in the art by chromatographic methods (such as nickel-nitrilotriacetic acid affinity chromatography, streptavidin affinity chromatography, gel filtration chromatography or ion-exchange chromatography) or else purified to homogeneity.

In one example the method used to determine the activity of enzyme $E_2$ involves first disrupting cells which contain this activity (i.e. the cells according to any aspect of the present invention) in a manner known to the person skilled in the art, for example with the aid of a ball mill, a French press or an ultrasonic disintegrator and subsequently separating of cells, cell debris and disruption aids, such as, for example, glass beads, by centrifugation for 10 min at 16,100 g at 4° C. Using the resulting cell-free crude extract, enzyme assays with subsequent LC-ESI-MS detection of the products can be carried out. As an alternative, the enzyme can be enriched in the manner known to the person skilled in the art by chromatography methods (such as nickel/nitrilotriacetic acid affinity chromatography, streptavidin affinity chromatography, gel filtration chromatography or ion-exchange chromatography) or else purified to homogeneity. This sample may then be used to measure the activity of enzyme $E_2$. In particular, the activity of enzyme $E_2$ may be determined using a standard assay that may consists of 185 μl of 10 mM Tris-HCl (pH 7.5), 10 μl mM NDP-glucose and 50

μl of protein crude extract (about 1 mg of total protein) or purified protein in solution (5 μg of purified protein). The reaction may be started by the addition of 10 μl mM ethanolic solution of 3-hydroxytetradecanoyl-3-hydroxydecanoic acid or 3-hydroxyhexadecanoyl-3-hydroxydecanoic acid and incubated for 1 h at 30° C. with shaking (600 rpm). Subsequently, the reaction may be treated with 1 ml of acetone. Undissolved constituents, may be sedimented by centrifugation (16,100 g, 5 min RT) and the sample may be analyzed by means of LC-ESI-MS. The identification of the products may then take place by analysis of the corresponding mass traces and the MS2 spectra. This method may be used to measure the activity of $E_2$.

In another example, the method used to determine the activity of enzyme $E_1$ involves first disrupting cells which contain this activity (i.e. the cells according to any aspect of the present invention) in a manner known to the person skilled in the art and subsequently separating of cells, cell debris and disruption aids, such as, for example, glass beads, by centrifugation for 10 min at 16,100 g at 4° C. Using the resulting cell-free crude extract, enzyme assays with subsequent LC-ESI-MS detection of the products can be carried out. As an alternative, the enzyme can be enriched in the manner known to the person skilled in the art by chromatography methods (such as nickel/nitrilotriacetic acid affinity chromatography, streptavidin affinity chromatography, gel filtration chromatography or ion-exchange chromatography) or else purified to homogeneity. This sample may then be used to measure the activity of enzyme $E_1$. In particular, the activity of enzyme $E_1$ may be determined using a standard assay which may contain 100 μM *E. coli* ACP, 1 mM β-mercaptoethanol, 200 μM malonyl-coenzyme A, 40 μM octanoyl-coenzyme A and 40 μM dodecanoyl-coenzyme A or 40 μM octanoyl-coenzyme A and 40 mM tetradecanoyl-coenzyme A, 100 μM NADPH, 2 μg of *E. coli* FabD, 2 μg of *Mycobacterium tuberculosis* FabH, 1 μg of *E. coli* FabG, 0.1 M sodium phosphate buffer (pH 7.0), and 5 μg of enzyme $E_1$ in a final volume of 120 μl. ACP, β-mercaptoethanol and sodium phosphate buffer may be preincubated for 30 min at 37° C. to reduce the ACP completely. The reaction may be started by addition of enzyme $E_1$. The reactions may be stopped using 2 ml of water, which has been acidified with HCl to pH 2.0, and subsequently extracted twice with 2 ml of chloroform/methanol (2:1 (v:v)). Phase separation may take place by centrifugation (16,100 g, 5 min, RT). The lower organic phase may be removed, evaporated completely in the vacuum centrifuge and the sediment may be taken up in 50 μl of methanol. Undissolved constituents, may be sedimented by centrifugation (16,100 g, 5 min RT) and the sample may be analyzed by means of LC-ESI-MS. The identification of the products may take place by analysis of the corresponding mass traces and the MS2 spectra.

The enzyme used according to any aspect of the present invention may be recombinant. The term "recombinant" as used herein, refers to a molecule or is encoded by such a molecule, particularly a polypeptide or nucleic acid that, as such, does not occur naturally but is the result of genetic engineering or refers to a cell that comprises a recombinant molecule. For example, a nucleic acid molecule is recombinant if it comprises a promoter functionally linked to a sequence encoding a catalytically active polypeptide and the promoter has been engineered such that the catalytically active polypeptide is overexpressed relative to the level of the polypeptide in the corresponding wild type cell that comprises the original unaltered nucleic acid molecule.

The cell used according to any aspect of the present invention may also be a non-pathogenic cell. A non-pathogenic cell refers to a cell that does not cause disease, harm or death to another organism. The cells according to any aspect of the present invention may any non-pathogenic prokaryote or eukaryote. These can be mammalian cells (such as, for example, cells from man), plant cells or microorganisms such as yeasts, fungi or bacteria, wherein microorganisms in particular bacteria and yeasts are preferred.

Suitable bacteria, yeasts or fungi are in particular those bacteria, yeasts or fungi that are deposited in the Deutsche Sammlung von Mikroorganismen and Zellkulturen (German Collection of Microorganisms and Cell Cultures) GmbH (DSMZ), Brunswick, Germany, as bacterial, yeast or fungal strains. Bacteria suitable according to the invention belong to the genera that are listed under:

http://www.dsmz.de/species/bacteria.htm, yeasts suitable according to the invention belong to those genera that are listed under:

http://www.dsmz.de/species/yeasts.htm and fungi suitable according to the invention are those that are listed under:

http://www.dsmz.de/species/fungi.htm.

In particular, the cells may be selected from the genera *Aspergillus, Corynebacterium, Brevibacterium, Bacillus, Acinetobacter, Alcaligenes, Lactobacillus, Paracoccus, Lactococcus, Candida, Pichia, Hansenula, Kluyveromyces, Saccharomyces, Escherichia, Zymomonas, Yarrowia, Methylobacterium, Ralstonia, Pseudomonas, Rhodospirillum, Rhodobacter, Burkholderia, Clostridium* and *Cupriavidus*. More in particular, the cells may be selected from the group consisting of *Aspergillus nidulans, Aspergillus niger, Alcaligenes latus, Bacillus megaterium, Bacillus subtilis, Brevibacterium flavum, Brevibacterium lactofermentum, Burkholderia andropogonis, B. brasilensis, B. caledonica, B. caribensis, B. caryophylli, B. fungorum, B. gladioli, B. glathei, B. glumae, B. graminis, B. hospita, B. kururiensis, B. phenazinium, B. phymatum, B. phytofirmans, B. plantarii, B. sacchari, B. singaporensis, B. sordidicola, B. terricola, B. tropica, B. tuberum, B. ubonensis, B. unamae, B. xenovorans, B. anthina, B. pyrrocinia, B. thailandensis, Candida blankii, Candida rugosa, Corynebacterium glutamicum, Corynebacterium efficiens, Escherichia coli, Hansenula polymorpha, Kluveromyces lactis, Methylobacterium extorquens, Paracoccus versutus, Pseudomonas argentinensis, P. borbori, P. citronellolis, P. flavescens, P. mendocina, P. nitroreducens, P. oleovorans, P. pseudoalcaligenes, P. resinovorans, P. straminea, P. aurantiaca, P. aureofaciens, P. chlororaphis, P. fragi, P. lundensis, P. taetrolens, P. antarctica, P. azotoformans, 'P. blatchfordae', P. brassicacearum, P. brenneri, P. cedrina, P. corrugata, P. fluorescens, P. gessardii, P. libanensis, P. mandelii, P. marginalis, P. mediterranea, P. meridiana, P. migulae, P. mucidolens, P. orientalis, P. panacis, P. proteolytica, P. rhodesiae, P. synxantha, P. thivervalensis, P. tolaasii, P. veronii, P. denitrificans, P. pertucinogena, P. cremoricolorata, P. fulva, P. monteilii, P. mosselii, P. parafulva, P. putida, P. balearica, P. stutzeri, P. amygdali, P. avellanae, P. caricapapayae, P. cichorii, P. coronafaciens, P. ficuserectae, 'P. helianthi', P. meliae, P. savastanoi, P. syringae, P. tomato, P. viridiflava, P. abietaniphila, P. acidophila, P. agarici, P. alcaliphila, P. alkanolytica, P. amyloderamosa, P. asplenii, P. azotifigens, P. cannabina, P. coenobios, P. congelans, P. costantinii, P. cruciviae, P. delhiensis, P. excibis, P. extremorientalis, P. frederiksbergensis, P. fuscovaginae, P. gelidicola, P. grimontii, P. indica, P. jessenii, P. jinjuensis, P. kilonensis, P.*

*knackmussii, P. koreensis, P. lini, P. lutea, P. moraviensis, P. otitidis, P. pachastrellae, P. palleroniana, P. papaveris, P. peli, P. perolens, P. poae, P. pohangensis, P. psychrophila, P. psychrotolerans, P. rathonis, P. reptilivora, P. resiniphila, P. rhizosphaerae, P. rubescens, P. salomonii, P. segitis, P. septica, P. simiae, P. suis, P. thermotolerans, P. aeruginosa, P. tremae, P. trivialis, P. turbinellae, P. tuticorinensis, P. umsongensis, P. vancouverensis, P. vranovensis, P. xanthomarina, Ralstonia eutropha, Rhodospirillum rubrum, Rhodobacter sphaeroides, Saccharomyces cerevisiae, Yarrowia lipolytica* and *Zymomonas mobile*. More in particular, the cell may be a bacterial cell selected from the group consisting of *Acinetobacter* sp., *Bacillus* sp., *Brevibacterium* sp., *Burkholderia* sp., *Chloralla* sp., *Clostridium* sp., *Corynebacterium* sp., *Cyanobakterien, Escherichia* sp., *Pseudomonas* sp., *Klebsiella* sp., *Salmonella* sp., *Rhizobium* sp., *Saccharomyces* sp., *Pichia* sp., and *Nostoc* sp. Even more in particular, the cell may be selected from the group consisting of *Bacillus subtilis, Burkholderia thailandensis, Corynebacterium glutamicum, E. coli, Klebsiella oxytoca, Pseudomonas fluorescens, Pseudomonas putida, Pseudomonas stutzeri, Rhizobium meliloti, Saccharomyces cerevisiae* and *Pichia pastoris.*

In one example, the cell according to any aspect of the present invention may be a cell that is genetically modified to increase the expression of

- enzyme $E_2$ comprises SEQ ID NO: 4 or variant thereof, and
- enzyme $E_1$ comprises SEQ ID NO: 2 or variant thereof.

The cell according to any aspect of the present invention may be a non-pathogenic cell that is genetically modified to increase the heterologous expression relative to the wild type cell of:

- an enzyme ($E_2$) capable of converting 3-hydroxyalkanoyl-3-hydroxyalkanoyl-CoA/ACP and/or 3-(3-hydroxyalkanoyloxy)alkanoic acid (HAA) to β-D-glucopyranosyl-3-hydroxyalkanoyl-3-hydroxyalkanoate, wherein $E_2$ is a glycosyltransferase (EC 2.4); and
- an enzyme ($E_1$) capable of converting 3-hydroxyalkanoyl-CoA/ACP into 3-hydroxyalkanoyl-3-hydroxyalkanoyl-CoA/ACP and further to 3-(3-hydroxyalkanoyloxy)alkanoic acid (HAA), wherein $E_1$ is a 3-(3-hydroxyalkanoyloxy)alkanoic acid (HAA) synthase.

The cell according to a further aspect of the present invention may be a non-pathogenic cell that is genetically modified to increase the heterologous expression relative to the wild type cell of:

- an enzyme ($E_2$) capable of converting 3-hydroxyalkanoyl-3-hydroxyalkanoyl-CoA/ACP or HAA to β-D-glucopyranosyl-3-hydroxyalkanoyl-3-hydroxyalkanoate, wherein $E_2$ is a glycosyltransferase (EC 2.4) that comprises SEQ ID NO:4; and
- an enzyme ($E_1$) capable of converting 3-hydroxyalkanoyl-CoA/ACP into 3-hydroxyalkanoyl-3-hydroxyalkanoyl-CoA/ACP and further to 3-(3-hydroxyalkanoyloxy)alkanoic acid (HAA), wherein $E_1$ is a 3-(3-hydroxyalkanoyloxy)alkanoic acid (HAA) synthase that comprises SEQ ID NO:2.

The cell according to any aspect of the present invention may be a non-pathogenic cell that is genetically modified to increase the heterologous expression relative to the wild type cell of:

- an enzyme ($E_2$) capable of converting 3-hydroxyalkanoyl-3-hydroxyalkanoyl-CoA/ACP or 3-(3-hydroxyalkanoyloxy)alkanoic acid (HAA) to β-D-glucopyranosyl-3-hydroxyalkanoyl-3-hydroxyalkanoate, wherein $E_2$ is a glycosyltransferase (EC 2.4); and
- an enzyme ($E_1$) capable of converting 3-hydroxyalkanoyl-CoA/ACP into 3-hydroxyalkanoyl-3-hydroxyalkanoyl-CoA/ACP and further to HAA, wherein $E_1$ is a 3-(3-hydroxyalkanoyloxy)alkanoic acid (HAA) synthase that comprises SEQ ID NO:6.

The cell according to one other aspect of the present invention may be a non-pathogenic cell that is genetically modified to increase the heterologous expression relative to the wild type cell of:

- an enzyme ($E_2$) capable of converting 3-hydroxyalkanoyl-3-hydroxyalkanoyl-CoA/ACP or HAA to β-D-glucopyranosyl-3-hydroxyalkanoyl-3-hydroxyalkanoate, wherein $E_2$ is a glycosyltransferase (EC 2.4); and
- an enzyme ($E_1$) capable of converting 3-hydroxyalkanoyl-CoA/ACP into 3-hydroxyalkanoyl-3-hydroxyalkanoyl-CoA/ACP and further to 3-(3-hydroxyalkanoyloxy)alkanoic acid (HAA), wherein $E_1$ is a 3-(3-hydroxyalkanoyloxy)alkanoic acid (HAA) synthase that comprises SEQ ID NO:8.

The cell according to yet another aspect of the present invention may be a non-pathogenic cell that is genetically modified to increase the heterologous expression relative to the wild type cell of:

- an enzyme ($E_2$) capable of converting 3-hydroxyalkanoyl-3-hydroxyalkanoyl-CoA/ACP or HAA to β-D-glucopyranosyl-3-hydroxyalkanoyl-3-hydroxyalkanoate, wherein $E_2$ is a glycosyltransferase (EC 2.4); and
- an enzyme ($E_1$) capable of converting 3-hydroxyalkanoyl-CoA/ACP into 3-hydroxyalkanoyl-3-hydroxyalkanoyl-CoA/ACP and further to 3-(3-hydroxyalkanoyloxy)alkanoic acid (HAA), wherein $E_1$ is a 3-(3-hydroxyalkanoyloxy)alkanoic acid (HAA) synthase that comprises SEQ ID NO:10.

The cell according to a further aspect of the present invention may be a non-pathogenic cell that is genetically modified to increase the heterologous expression relative to the wild type cell of:

- an enzyme ($E_2$) capable of converting 3-hydroxyalkanoyl-3-hydroxyalkanoyl-CoA/ACP or HAA to β-D-glucopyranosyl-3-hydroxyalkanoyl-3-hydroxyalkanoate, wherein $E_2$ is a glycosyltransferase (EC 2.4) that comprises SEQ ID NO:4; and
- an enzyme ($E_1$) capable of converting 3-hydroxyalkanoyl-CoA/ACP into 3-hydroxyalkanoyl-3-hydroxyalkanoyl-CoA/ACP and further to 3-(3-hydroxyalkanoyloxy)alkanoic acid (HAA), wherein $E_1$ is a 3-(3-hydroxyalkanoyloxy)alkanoic acid (HAA) synthase that comprises SEQ ID NO:12.

The cell according to a further aspect of the present invention may be a non-pathogenic cell that is genetically modified to increase the heterologous expression relative to the wild type cell of:

- an enzyme ($E_2$) capable of converting 3-hydroxyalkanoyl-3-hydroxyalkanoyl-CoA/ACP or HAA to β-D-glucopyranosyl-3-hydroxyalkanoyl-3-hydroxyalkanoate, wherein $E_2$ is a glycosyltransferase (EC 2.4) that comprises SEQ ID NO:4; and
- an enzyme ($E_1$) capable of converting 3-hydroxyalkanoyl-CoA/ACP into 3-hydroxyalkanoyl-3-hydroxyalkanoyl-CoA/ACP and further to 3-(3-hydroxyalkanoyloxy)alkanoic acid (HAA), wherein $E_1$ is a 3-(3-hydroxyalkanoyloxy)alkanoic acid (HAA) synthase that comprises SEQ ID NO:14.

The cells according to any aspect of the present invention may be used to produce a lipid according to General formula I and/or II from a carbon substrate:

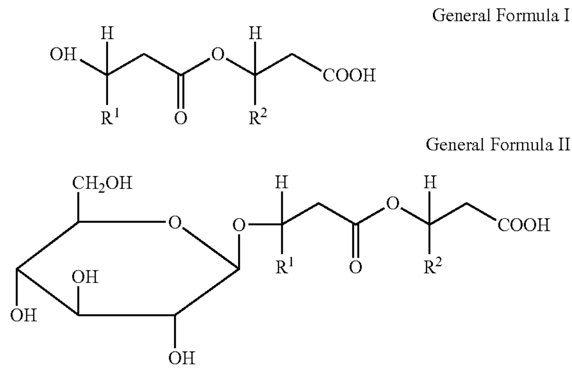

wherein $R^1$ and $R^2$ independently of one another in General Formula I or II is an identical or different alkyl group with 5 to 13 carbon atoms. In particular, the alkyl group may be saturated or unsaturated. More in particular, the alkyl group of $R^1$ and/or $R^2$ may be a monounsaturated alkyl radical. Even more in particular, $R^1$ and/or $R^2$ may be selected from the group consisting of pentenyl, heptenyl, nonenyl, undecenyl, tridecenyl and $(CH_2)_n$—$CH_3$ with n=4-12.

The lipids formed may be combination of lipids with general formula I and II with varying R group that may be produced during a single reaction.

The genetically modified cells according to the invention can be brought into contact with the nutrient medium continuously or discontinuously in the batch process (batch culture) or in the fed-batch process (feed process) or repeated fed-batch process (repetitive feed process) for the purpose of the production of the abovementioned products and thus cultured. A semi-continuous process is also conceivable, as is described in GB-A-1009370. A summary of known culturing methods are described in the textbook of Chmiel ("Bioprozesstechnik 1. Einfuhrung in die Bioverfahrenstechnik" [Bioprocess Technology 1. Introduction to the Bioprocess Technique] (Gustav Fischer Verlag, Stuttgart, 1991)) or in the textbook of Storhas ("Bioreaktoren and periphere Einrichtungen" [Bioreactors and Peripheral Devices], Vieweg Verlag, Brunswick/Wiesbaden, 1994).

The culture medium to be used must satisfy in a suitable manner the demands of the respective strains. Descriptions of culture media of different yeast strains are contained, for example, in "Nonconventional yeast in biotechnology" (Ed. Klaus Wolf, Springer-Verlag Berlin, 1996).

The carbon source used as a substrate according to any aspect of the present invention may be selected from the group consisting of carbohydrates such as, for example, glucose, sucrose, arabinose, xylose, lactose, fructose, maltose, molasses, starch, cellulose and hemicellulose, vegetable and animal oils and fats such as, for example, soybean oil, safflower oil, peanut oil, hempseed oil, jatropha oil, coconut fat, calabash oil, linseed oil, corn oil, poppyseed oil, evening primrose oil, olive oil, palm kernel oil, palm oil, rapeseed oil, sesame oil, sunflower oil, grapeseed oil, walnut oil, wheat germ oil and coconut oil, fatty acids, such as, for example, caprylic acid, capric acid, lauric acid, myristic acid, palmitic acid, palmitoleic acid, stearic acid, arachidonic acid, behenic acid, oleic acid, linoleic acid, linolenic acid, gamma-linolenic acid and its methyl or ethyl ester as well as fatty acid mixtures, mono-, di- and triglycerides containing the fatty acids just mentioned, alcohols such as, for example, glycerol, ethanol and methanol, hydrocarbons such as methane, ethane, propane or butane carbon-containing gases and gas mixtures, such as CO, $CO_2$, synthesis or flue gas, amino acids such as L-glutamate or L-valine or organic acids such as, for example, acetic acid. These substances can be used individually or as a mixture. The use of carbohydrates, in particular of monosaccharides, oligosaccharides or polysaccharides, as the carbon source as is described in U.S. Pat. No. 6,136,576 as well as of hydrocarbons, in particular of alkanes, alkenes and alkynes. In particular, the carbon source may be selected from the group consisting of glucose, dextrose, sucrose, polysaccharides, such as cellulose or hemicelluloses, vegetal oils, animal fats, fatty acids, fatty acid esters, carbonaceous gases, alkanes, glycerol, acetate, ethanol and methanol. More in particular, the carbon source may be selected from the group consisting of glucose, sucrose, glycerol, vegetal oils, methane, ethane, and butane. It is a great advantage of the present invention that the cells according to the invention are able to form lipids with general formula I and/or II from the simplest carbon sources such as, for example, glucose, sucrose or glycerol, such that a provision of longer-chain C sources in the medium during the method according to any aspect of the present invention is not necessary.

According to one aspect of the present invention there is provided a method of producing at least one lipid with general formula II:

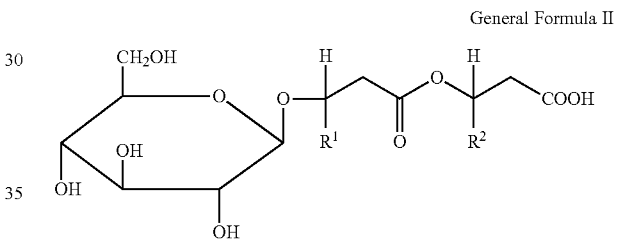

wherein $R^1$ and $R^2$ independently of one another is an identical or different alkyl group with 5 to 13 carbon atoms, and wherein the method comprises a step of contacting at least one cell according to any aspect of the present invention with at least one carbon source.

In particular, the alkyl group of $R^1$ and/or $R^2$ may be saturated or unsaturated. More in particular, the alkyl group of $R^1$ and/or $R^2$ may be a monounsaturated alkyl radical. Even more in particular, $R^1$ and/or $R^2$ may be selected from the group consisting of pentenyl, heptenyl, nonenyl, undecenyl, tridecenyl and $(CH_2)_n$—$CH_3$ with n=4-12.

The method according to any aspect of the present invention may also be used to produce a further lipid with general formula I from the carbon substrate,

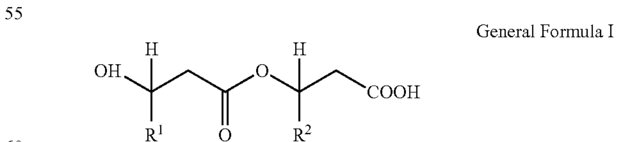

wherein $R^1$ and $R^2$ independently of one another is an identical or different alkyl group with 5 to 13 carbon atoms. In particular, the alkyl group of $R^1$ and/or $R^2$ may be saturated or unsaturated. More in particular, the alkyl group of $R^1$ and/or $R^2$ may be a monounsaturated alkyl radical. Even more in particular, $R^1$ and/or $R^2$ may be selected from the group consisting of pentenyl, heptenyl, nonenyl, undecenyl tridecenyl and $(CH_2)_n$—$CH_3$ with n=4-12.

The method according to any aspect of the present invention may be used to produce a mixture of lipids comprising the lipid in general formula I and II. In particular, the lipids of general formula I and II are produced in the ratio of 1:100, 1:90, 1:80, 1:70, 1:60, 1:50, 1:40, 1:30, 1:20, 1:10, 1:5, 1:4, 1:3, 1:2, 1:1, 2:1, 3:1, 4:1, 5:1, 10:1, 20:1, 30:1, 40:1, 50:1, 60:1, 70:1, 80:1, 90:1 or 100:1. More in particular lipids of formula I and II may have varying lengths of alkyls present simultaneously in the R subgroup.

According to a further aspect of the present invention, there is provided a use of the cell according to any aspect of the present invention for producing at least one lipid with general formula I and/or II:

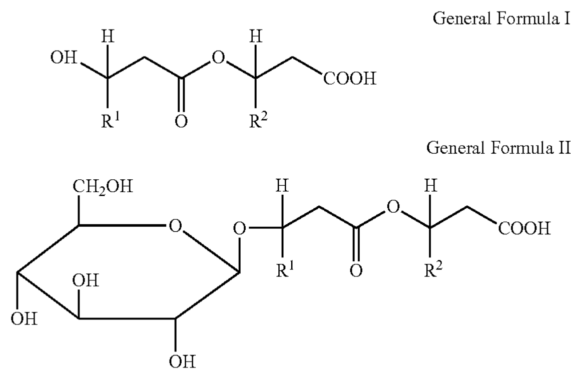

wherein $R^1$ and $R^2$ independently of one another is an identical or different alkyl group with 5 to 13 carbon atoms. In particular, the alkyl group of $R^1$ and/or $R^2$ may be saturated or unsaturated. More in particular, the alkyl group of $R^1$ and/or $R^2$ may be a monounsaturated alkyl radical. Even more in particular, $R^1$ and/or $R^2$ may be selected from the group consisting of pentenyl, heptenyl, nonenyl, undecenyl, tridecenyl and $(CH_2)_n$—$CH_3$ with n=4-12.

EXAMPLES

The foregoing describes preferred embodiments, which, as will be understood by those skilled in the art, may be subject to variations or modifications in design, construction or operation without departing from the scope of the claims. These variations, for instance, are intended to be covered by the scope of the claims.

Example 1

Construction of an expression vector for the *Serratia rubidaea* genes rbwAB For the heterologous expression of the genes rbwA (SEQ ID NO. 1) as enzyme $E_1$ and rbwB (SEQ ID NO. 3) as enzyme $E_2$ from *Serratia rubidaea* the plasmid pACYC_rbwAB_Srub was constructed. The synthetic operon consisting of rbwAB_Srub (SEQ ID NO: 15) which encode an 3-(3'-hydroxyalkanoyloxy)alkanoic acids (HAAs) synthase (RbwA, SEQ ID NO: 2) and a glucosyltransferase (RbwB, SEQ ID NO: 4), respectively, was cloned under the control of the rhamnose inducible promoter $P_{rha}$ into the vector pACYCATh-5, which is based on pAYCY184 (New England Biolabs, Frankfurt/Main, Germany). Downstream of the synthetic operon a terminator sequence is located. The genes were amplified from genomic DNA of *S. rubidaea* via PCR. The $P_{Rha}$ promoter cassette (SEQ ID NO: 16) and the terminator sequence (SEQ ID NO: 17) were amplified from *E. coli* K12 genomic DNA. The plasmid pACYCATh-5 carries a p15A origin of replication for *E. coli* and a pVS1 origin of replication for the replication in *P. putida* KT2440. The pVS1 origin comes from the Pseudomonas plasmid pVS1 (Itoh Y, et al. *Plasmid* 1984, 11(3), 206-20). rbwA and rbwB were fused via cross-over PCR to generate an optimized operon. For amplification the Phusion™ High-Fidelity Master Mix from New England Biolabs (Frankfurt/Main, Germany) was used according to manufacturer's manual. In the next step the fusion construct was cloned into the vector pACYCATh-5 using the restriction sites ApaI/PspXI. The ligated product was transformed into chemically competent *E. coli* DH5c cells (New England Biolabs, Frankfurt/Main, Germany). Procedure of PCR purification, cloning and transformation were carried out according to manufacturer's manual. The correct insertion of the target genes was checked by restriction analysis and the authenticity of the introduced DNA fragments was verified by DNA sequencing. The resulting plasmid was named pACYC_rbwAB_Srub (SEQ ID NO: 18). The *P. putida* strain KT2440 was transformed with the plasmid pACYC_rbwAB_Srub by means of electroporation (Iwasaki K, et al., *Biosci. Biotech. Biochem.* 1994. 58(5):851-854)) and plated onto LB-agar plates supplemented with kanamycin (50 μg/mL). Transformants were checked for the presence of the correct plasmid by plasmid preparation and analytic restriction analysis. The resulting strain was named BS-PP-360 (*P. putida* KT2440 pACYC_rbwAB_Srub).

Example 2

Construction of an expression vector for the *Serratia rubidaea* gene rbwA For the heterologous expression of the gene rbwA (SEQ ID NO: 1) from *S. rubidaea* the plasmid pACYC_rbwA_Srub was constructed. For this approach the plasmid pACYC_rbwAB_Srub (see Example 1) was cut with the restriction enzymes NsiI and XhoI to eliminate rbwB. To re-ligate the modified vector, the plasmid was treated with T4 DNA polymerase (New England Biolabs, Frankfurt/Main, Germany) in order to remove 3' overhangs and to fill-in of 5' overhangs to form blunt ends. The religated product was transformed into chemically competent *E. coli* DH5a cells (New England Biolabs, Frankfurt/Main, Germany). Procedure of PCR purification, cloning and transformation were carried out according to manufacturer's manual. The correct insertion of the target genes was checked by restriction analysis and the authenticity of the introduced DNA fragments was verified by DNA sequencing. The resulting plasmid was named pACYC_rbwA_Srub (SEQ ID NO: 19). The *P. putida* strain KT2440 was transformed with the plasmid pACYC_rbwA_Srub by means of electroporation (Iwasaki K, et al. *Biosci. Biotech. Biochem.* 1994. 58(5):851-854) and plated onto LB-agar plates supplemented with kanamycin (50 μg/mL). Transformants were checked for the presence of the correct plasmid by plasmid preparation and analytic restriction analysis. The resulting strain was named BS-PP-433 (*P. putida* KT2440 pACYC_rbwA_Srub).

Example 3

Construction of an expression vector for the *P. aeruginosa* gene rh/A and *S. rubidaea* gene rbwB For the heterologous expression of the gene rhIA (SEQ ID NO: 5) from *P. aeruginosa* and rbwB (SEQ ID NO: 3) from *S. rubidaea* the plasmid pACYC_rhIA_Pa rbwB_Srub was constructed. The synthetic operon consisting of rhIA_Pa (SEQ ID NO: 20) which encodes a 3-(3-hydroxyalkanoyloxy)alkanoic acid (HAAs) synthase (RhIA, SEQ ID NO: 6) and a glucosyltransferase (RbwB, SEQ ID NO: 4), respectively, was cloned under the control of the rhamnose inducible promoter $P_{rha}$ into the vector pACYCATh-5. Downstream of the synthetic operon a terminator sequence is located. The genes were amplified from genomic DNA of *P. aeruginosa* and *S. rubidaea* respectively via PCR. The $P_{Rha}$ promoter cassette (SEQ ID NO: 16) and the terminator sequence (SEQ ID NO: 17) were amplified from *E. coli* K12 genomic DNA. The vector is based on pACYC184 (New England Biolabs, Frankfurt/Main, Germany) and carries a p15A origin of replication for *E. coli* and a pVS1 origin of replication for the replication in *P. putida* KT2440. The pVS1 origin comes from the Pseudomonas plasmid pVS1 (Itoh Y, Watson J M, Haas D, Leisinger T, Plasmid 1984, 11(3), 206-20). rh/A and rbwB were fused via cross-over PCR to generate an optimized operon. For amplification the Phusion™ High-Fidelity Master Mix from New England Biolabs (Frankfurt/Main, Germany) was used according to manufacturer's manual. In the next step the fusion construct was cloned into the vector pACYCATh-5 using the restriction sites ApaI/PspXI. The ligated product was transformed into chemically competent *E. coli* DH5c cells (New England Biolabs, Frankfurt/Main, Germany). Procedure of PCR purification, cloning and transformation were carried out according to manufacturer's manual. The correct insertion of the target genes was checked by restriction analysis and the authenticity of the introduced DNA fragments was verified by DNA sequencing. The resulting plasmid was named pACYC_rhIA_Pa rbwB_Srub (SEQ ID NO: 21).

The *P. putida* strain KT2440 was transformed with the plasmid pACYC_rhIA_Pa rbwB_Srub by means of electroporation (Iwasaki K, et al., *Biosci. Biotech. Biochem.* 1994. 58(5):851-854)) and plated onto LB-agar plates supplemented with kanamycin (50 µg/mL). Transformants were checked for the presence of the correct plasmid by plasmid preparation and analytic restriction analysis. The resulting strain was named BS-PP-368 (*P. putida* KT2440 pACYC_rhIA_Pa rbwB_S rub).

Example 4

Production of Lipid R1 with Strain BS-PP-433 (*P. putida* KT2440 pACYC_rbwA_Srub)

For the production of lipid R1, DASGIP® parallel bioreactor system from Eppendorf (Hamburg, Germany) is used. The fermentation is performed using 1 L reactors. pH and pO2 are measured online for process monitoring. OTR/CTR measurements serve for estimating the metabolic activity and cell fitness, inter alia.

The pH electrodes are calibrated by means of a two-point calibration using standard solutions of pH 4.0 and pH 7.0, as specified in DASGIP's technical instructions. The reactors are equipped with the necessary sensors and connections as specified in the technical instructions, and the agitator shaft is fitted. The reactors are then filled with 300 ml water and autoclaved for 20 min at 121° C. to ensure sterility. The pO2 electrodes are connected to the measuring amplifiers and polarized overnight (for at least 6 h). Thereafter, the water is removed under a clean bench and replaced by fermentation medium (2.2 g/L $(NH_4)_2SO_4$, 0.02 g/L NaCl, 0.4 g/L $MgSO_4 \times 7H_2O$, 0.04 g/L $CaCl_2 \times 2H_2O$, sterilized separately: 2 g/L $KH_2PO_4$, 8.51 g/L $KH_2PO_4$, 20 g/L glucose, 10 mL/L trace elements solution M12 (sterile-filtered: 0.2 g/L ZnSO4×7H2O, 0.1 g/L $MnCl_2 \times 4H_2O$, 1.5 g/L $Na_3$-Citrat×$2H_2O$, 0.1 g/L $CuSO_4 \times 5H_2O$, 0.002 g/L $NiCl_2 \times 6H_2O$, 0.003 g/L $Na_2MoO_4 \times 2H_2O$, 0.03 g/L $H_3BO_3$, 1 g/L $FeSO_4 \times 7H_2O$). Thereafter, the pO2 electrodes are calibrated to 100% with a one-point calibration (stirrer: 600 rpm/aeration 10 sl/h air), and the feed, correction agent and induction agent lines are cleaned by "cleaning in place" as specified in the technical instructions. To this end, the tubes are rinsed first with 70% ethanol, then with 1 M NaOH, then with sterile fully-demineralized water and, finally, filled with the respective media.

Using the BS-PP-433 (*P. putida* strain KT2440 pACYC_rbwA_Srub), 25 ml LB1 medium (10 g/L tryptone, 5 g/L yeast extract, 1 g/L NaCl, pH 7.0) supplemented with kanamycin (50 µg/mL) in a baffeled shake flask are inoculated with 100 µl of a glycerol stock solution and incubated for ~18 h over night at 30° C. and 200 rpm. The first preculture is used to inoculate 50 ml seed medium (autoclaved: 4.4 g/L $Na_2HPO_4$*$2H_2O$, 1.5 g/L $KH_2PO_4$, 1 g/L $NH_4Cl$, 10 g/L yeast extract, sterilized separately: 20 g/L glucose, 0.2 g/L $MgSO_4$*$7H_2O$, 0.006 g/L $FeCl_3$, 0.015 g/L $CaCl_2$, 1 ml/L trace elements solution SL6 (sterile-filtered: 0.3 g/L $H_3BO_3$, 0.2 g/L $CoCl_2 \times H_2O$, 0.1 g/L $ZnSO_4 \times 7$ $H_2O$, 0.03 g/L $MnCl_2 \times 4H_2O$, 0.01 g/L $CuCl_2 \times 2H_2O$, 0.03 g/L $Na_2MoO_4 \times 2H_2O$, 0.02 g/L $NiCl_2 \times 6H_2O$) in a 500 ml baffeled shake flask (starting $OD_{600}$ 0.2). The culture is incubated for ~7 h at 200 rpm and 30° C. In order to inoculate the reactors with an optical density of 0.7, the 00600 of the second preculture stage is measured and the amount of culture required for the inoculation is calculated.

The required amount of culture is added with the help of a 30 ml syringe through a septum into the heat-treated and aerated reactor.

The standard program shown in Table 1 is used:

TABLE 1

Standard program used for heated and aerated reactor a)

| DO controller | | pH controller | |
|---|---|---|---|
| Preset | 0% | Preset | 0 mL/h |
| P | 0.1 | P | 5 |
| Ti | 300 s | Ti | 200 s |
| Min | 0% | Min | 0 mL/h |
| Max | 100% | Max | 40 mL/h |

TABLE 1-continued

Standard program used for heated and aerated reactor b)

| N (Rotation) | From | To | XO2 (gas mixture) | from | to | F (gas flow) | from | to |
|---|---|---|---|---|---|---|---|---|
| Growth and biotrans-formation | 0%<br>500 rpm | 40%<br>1500 rpm | Growth and biotrans-formation | 0%<br>21% | 100%<br>21% | Growth and biotrans-formation | 35%<br>9 sl/h | 100%<br>72 sL/h |

c)

| Script | |
|---|---|
| Trigger fires | 31% DO (1/60 h) |
| Temperature | 37° C. |
| Induction rhamnose | 3 h after the feed start |
| Feed trigger | 50% DO |
| Feed rate | 1.5 [mL/h] |

The pH is adjusted unilaterally to pH 7.0 with 12.5% strength ammonia solution. During the growth phase and the biotransformation, the dissolved oxygen (pO2 or DO) in the culture is adjusted to at least 30% via the stirrer speed and the aeration rate. After the inoculation, the DO dropped from 100% to these 30%, where it is maintained permanently for the rest of the fermentation.

The fermentation is carried out as a fed batch. The feed starts with a 2.5 g/L*h glucose feed, composed of 500 g/L glucose, and was triggered via the DO peak which indicates the end of the batch phase. 3 h after the feed start, the expression of lipid R1 production was induced with 0.2% (w/v) rhamnose. The inducer concentration refers to the volume at the beginning of fermentation.

The production of lipid R1 starts with the induction. At specified time points samples are taken from the fermenter to determine the concentration of lipid R1 produced.

The strain BS-PP-433 produces more 3-(3-hydroxyalkanoyloxy)alkanoic acid (HAA) than the reference strain with an empty plasmid.

Example 5

Production of Rubiwettin RG1 with Strain BS-PP-360 (*P. putida* KT2440 pACYC_rbwAB_Srub)

For the production of rubiwettin RG1 the DASGIP® parallel bioreactor system from Eppendorf (Hamburg, Germany) was used. The fermentation was performed using 1 L reactors. pH and pO2 were measured online for process monitoring. OTR/CTR measurements served for estimating the metabolic activity and cell fitness, inter alia.

The pH electrodes were calibrated by means of a two-point calibration using standard solutions of pH 4.0 and pH7.0, as specified in DASGIP's technical instructions. The reactors were equipped with the necessary sensors and connections as specified in the technical instructions, and the agitator shaft was fitted. The reactors were then filled with 300 ml water and autoclaved for 20 min at 121° C. to ensure sterility. The pO2 electrodes were connected to the measuring amplifiers and polarized overnight (for at least 6 h). Thereafter, the water was removed under a clean bench and replaced by fermentation medium (2.2 g/L $(NH_4)_2SO_4$, 0.02 g/L NaCl, 0.4 g/L $MgSO_4 \times 7H_2O$, 0.04 g/L $CaCl_2 \times 2H_2O$, sterilized separately: 2 g/L $KH_2PO_4$, 8.51 g/L $KH_2PO_4$, 20 g/L glucose, 10 mL/L trace elements solution M12 (sterile-filtered: 0.2 g/L $ZnSO_4 \times 7H_2O$, 0.1 g/L $MnCl_2 \times H_2O$, 1.5 g/L $Na_3$-Citrat$\times 2H_2O$, 0.1 g/L $CuSO_4 \times 5H_2O$, 0.002 g/L $NiCl_2 \times 6H_2O$, 0.003 g/L $Na_2MoO_4 \times 2H_2O$, 0.03 g/L $H_3BO_3$, 1 g/L $FeSO_4 \times 7H_2O$). thereafter, the pO2 electrodes were calibrated to 100% with a one-point calibration (stirrer: 600 rpm/aeration 10 sl/h air), and the feed, correction agent and induction agent lines were cleaned by "cleaning in place" as specified in the technical instructions. To this end, the tubes were rinsed first with 70% ethanol, then with 1 M NaOH, then with sterile fully-demineralized water and, finally, filled with the respective media.

Using the *P. putida* strain BS-PP-360, 25 ml LB1 medium (10 g/L tryptone, 5 g/L yeast extract, 1 g/L NaCl, pH 7.0) supplemented with kanamycin (50 μg/mL) in a baffeled shake flask were inoculated with 100 μl of a glycerol stock solution and incubated for ~18 h over night at 30° C. and 200 rpm. The first preculture was used to inoculate 50 ml seed medium (autoclaved: 4.4 g/L $Na_2HPO_4$*$2H_2O$, 1.5 g/L $KH_2PO_4$, 1 g/L $NH_4Cl$, 10 g/L yeast extract, sterilized separately: 20 g/L glucose, 0.2 g/L $MgSO_4$*$7H_2O$, 0.006 g/L $FeCl_3$, 0.015 g/L $CaCl_2$, 1 ml/L trace elements solution SL6 (sterile-filtered: 0.3 g/L $H_3BO_3$, 0.2 g/L $CoCl_2 \times 6H_2O$, 0.1 g/L $ZnSO_4 \times 7H_2O$, 0.03 g/L $MnCl_2 \times 4H_2O$, 0.01 g/L $CuCl_2 \times 2H_2O$, 0.03 g/L $Na_2MoO_4 \times 2H_2O$, 0.02 g/L $NiCl_2 \times 6H_2O$) in a 500 ml baffeled shake flask (starting $OD_{600}$ 0.2). The culture were incubated for ~7 h at 200 rpm and 30° C. In order to inoculate the reactors with an optical density of 0.7, the 00600 of the second preculture stage was measured and the amount of culture required for the inoculation was calculated.

The required amount of culture was added with the help of a 30 ml syringe through a septum into the heat-treated and aerated reactor. The standard program shown in example 4 of table 1 was used.

The pH was adjusted unilaterally to pH 7.0 with 12.5% strength ammonia solution. During the growth phase and the biotransformation, the dissolved oxygen (pO2 or DO) in the culture was adjusted to at least 30% via the stirrer speed and the aeration rate. After the inoculation, the DO dropped from 100% to these 30%, where it was maintained stably for the remainder of the fermentation.

The fermentation was carried out as a fed batch. The feed starts with a 2.5 g/L*h glucose feed, composed of 500 g/L glucose, and was triggered via the DO peak which indicates the end of the batch phase. 3 h after the feed start, the expression of rubiwettin production was induced with 0.2% (w/v) rhamnose. The inducer concentration referred to the volume at the beginning of fermentation. For both sugars stock solution of 220 g/L was used. The production of rubiwettin RG1 started with the induction. At specified time points samples were taken from the fermenter to determine the concentration of rubiwettins produced. After 65 h fermentation 0.53 g/L rubiwettin RG1 was produced.

Example 6

Production of Rubiwettin RG1 with Strain BS-PP-368 (*P. putida* KT2440 pACYC_rhIA_Pa rbwB_Srub)

For the production of rubiwettin RG1 the DASGIP® parallel bioreactor system from Eppendorf (Hamburg, Germany) was used. The fermentation was performed using 1 L reactors. pH and pO2 were measured online for process monitoring. OTR/CTR measurements served for estimating the metabolic activity and cell fitness, inter alia.

The pH electrodes were calibrated by means of a two-point calibration using standard solutions of pH 4.0 and pH 7.0, as specified in DASGIP's technical instructions. The reactors were equipped with the necessary sensors and connections as specified in the technical instructions, and the agitator shaft was fitted. The reactors were then filled with 300 ml water and autoclaved for 20 min at 121° C. to ensure sterility. The pO2 electrodes were connected to the measuring amplifiers and polarized overnight (for at least 6 h). Thereafter, the water was removed under a clean bench and replaced by fermentation medium (2.2 g/L $(NH_4)_2SO_4$, 0.02 g/L NaCl, 0.4 g/L $MgSO_4 \times 7H_2O$, 0.04 g/L $CaCl_2 \times 2H_2O$, sterilized separately: 2 g/L $KH_2PO_4$, 8.51 g/L $KH_2PO_4$, 20 g/L glucose, 10 mL/L trace elements solution M12 (sterile-filtered: 0.2 g/L $ZnSO_4 \times 7H_2O$, 0.1 g/L $MnCl_2 \times 4H_2O$, 1.5 g/L $Na_3$-Citrat$\times 2H_2O$, 0.1 g/L $CuSO_4 \times 5H_2O$, 0.002 g/L $NiCl_2 \times 6H_2O$, 0.003 g/L $Na_2MoO_4 \times 2H_2O$, 0.03 g/L $H_3BO_3$, 1 g/L $FeSO_4 \times 7H_2O$). Thereafter, the pO2 electrodes were calibrated to 100% with a one-point calibration (stirrer: 600 rpm/aeration 10 sl/h air), and the feed, correction agent and induction agent lines were cleaned by "cleaning in place" as specified in the technical instructions.

To this end, the tubes were rinsed first with 70% ethanol, then with 1 M NaOH, then with sterile fully-demineralized water and, finally, filled with the respective media.

Using the *P. putida* strain BS-PP-368, 25 ml LB1 medium (10 g/L tryptone, 5 g/L yeast extract, 1 g/L NaCl, pH 7.0) supplemented with kanamycin (50 μg/mL) in a baffeled shake flask were inoculated with 100 μl of a glycerol stock solution and incubated for ~18 h over night at 30° C. and 200 rpm. The first preculture was used to inoculate 50 ml seed medium (autoclaved: 4.4 g/L $Na_2HPO_4*2H_2O$, 1.5 g/L $KH_2PO_4$, 1 g/L $NH_4Cl$, 10 g/L yeast extract, sterilized separately: 20 g/L glucose, 0.2 g/L $MgSO_4*7H_2O$, 0.006 g/L $FeCl_3$, 0.015 g/L $CaCl_2$, 1 ml/L trace elements solution SL6 (sterile-filtered: 0.3 g/L $H_3BO_3$, 0.2 g/L $CoCl_2 \times 6H_2O$, 0.1 g/L $ZnSO_4 \times 7H_2O$, 0.03 g/L $MnCl_2 \times 4H_2O$, 0.01 g/L $CuCl_2 \times 2H_2O$, 0.03 g/L $Na_2MoO_4 \times 2H_2O$, 0.02 g/L $NiCl_2 \times 6H_2O$) in a 500 ml baffeled shake flask (starting OD600 0.2). The culture were incubated for ~7 h at 200 rpm and 30° C. In order to inoculate the reactors with an optical density of 0.7, the 00600 of the second preculture stage was measured and the amount of culture required for the inoculation was calculated.

The required amount of culture was added with the help of a 30 ml syringe through a septum into the heat-treated and aerated reactor. The standard program shown in table 1 of example 4 was used for the heated and aerated reactor.

The pH was adjusted unilaterally to pH 7.0 with 12.5% strength ammonia solution. During the growth phase and the biotransformation, the dissolved oxygen (pO2 or DO) in the culture was adjusted to at least 30% via the stirrer speed and the aeration rate. After the inoculation, the DO dropped from 100% to these 30%, where it was maintained stably for the remainder of the fermentation.

The fermentation was carried out as a fed batch. The feed starts with a 2.5 g/L*h glucose feed, composed of 500 g/L glucose, and was triggered via the DO peak which indicates the end of the batch phase. 3 h after the feed start, the expression of rubiwettin production was induced with 0.2% (w/v) rhamnose. The inducer concentration referred to the volume at the beginning of fermentation. For both sugars stock solution of 220 g/L was used. The production of rubiwettin RG1 started with the induction. At specified time points samples were taken from the fermenter to determine the concentration of rubiwettins produced. After 65 h fermentation 11.1 g/L rubiwettin RG1 was produced.

Example 7

HPLC-Based Quantification of Rubiwettins

Quantification of lipids R1 and RG1 was carried out by means of HPLC. Using a displacement pipette (Combitip), 900 μl of 70% (v/v) n-propanol was introduced into a 2 ml reaction vessel and the reaction vessel was immediately closed for minimization of evaporation. The addition of 100 μl fermentation broth followed. After shaking for 1 min in a Retsch mill at a frequency of 30 Hz, the resulting crude extract mixture was centrifuged for 5 min at 13,000 rpm, and 800 μl of the clear supernatant was transferred into an HPLC vial. Further dilutions of cell broth were carried out in 55% (v/v) propanol. Samples were stored at −20° C. before measurement.

For the detection and quantification of lipids an evaporation light scattering detector (Sedex LT-ELSD Model 85LT) was used. The measurement was carried out by means of Agilent Technologies 1200 Series (Santa Clara, Calif.) and a Zorbax SB-C8 Rapid Resolution column (4,6×150 mm, 3.5 μm, Agilent). The injection volume was 5.0 μl and the run time was 20 min. Mobile phase A: aqueous 0.1% TFA (trifluoracetic acid, solution); mobile phase B: methanol. The column temperature was 40° C. The ELSD (detector temperature 60° C.) and the DAD (diode array, 210 nm) were used as detectors.

Gradient:

TABLE 2

Gradient of mobile phases of A and B over time

| t [min] | | Flow [1 ml/min] |
|---|---|---|
| 0.00 | 70% | 1.00 |
| 15.00 | 100% | 1.00 |
| 15.01 | 70% | 1.00 |
| 20.00 | 70% | 1.00 |

The gradient used starts with 70% B in A to 100% B within 15 minutes at a flow rate of 1 mL/min followed by 5 minutes of re-equilibration with 70% B in A (see Table 2). Reference materials were used whose identity and purity were checked by HPLC-MS/MS and NMR.

Example 8

Construction of *Agrobacterium tumefaciens* Strains for Production of Rubiwettin R1 and Rubiwettin RG1

In order to show production of rubiwettins with yet another microbial species, *Agrobacterium tumefaciens*, we prepare electrocompetent cells of *Agrobacterium tumefaciens* LBA 4404 and transformed it with plasmids pACYC_rbwA_Srub (SEQ ID NO: 19), pACYC_rbwAB_Srub (SEQ ID NO: 18) and pACYC_rhIA_Pa rbwB_Srub (SEQ ID NO: 21).

To that end, freshly growing cells (1-2 days old) of *A. tumefaciens* LBA 4404 are spread on LB agar plates (diameter 90 mm, 10 g/L tryptone, 5 g/L yeast extract, 5 g/L NaCl, and 15 g/L agar, supplemented with 50 μg/mL rifampicin) and incubated overnight (~16 h) at 27° C. to produce a bacterial lawn that covers the surface of the plate completely.

Bacterial cells are carefully washed off the plate with 4 mL ice-cold 10% (v/v) sterile glycerol. Cells growing on the surface of the plate are scraped off with an inoculation loop avoiding damages of the agar medium and suspended in the glycerol solution. The bacterial suspension is then transferred into two sterile 2 mL centrifuge tubes.

Suspensions in the two tubes are centrifuged at 14,000 rpm (18,000 g) for 1 min at 4° C.; the supernatant is discarded.

1 mL ice-cold 10% (v/v) sterile glycerol is added to each tube containing the bacterial pellet. The tubes are thoroughly vortexed afterwards to resuspend the cells and this washing step is repeated one more time.

After the two centrifugation steps, the supernatant is removed and discarded again and the bacterial pellets in the two tubes are resuspended in 200 μl ice-cold 10% (v/v) sterile glycerol each and combined in one tube (yielding 400 μl in total).

The tube with the *Agrobacterium* cell suspension is kept on ice until electroporation.

For electroporation 70-80 μl of the ice-cold suspension of electrocompetent bacterial cells is mixed with 1-3 μl plasmid DNA (1-100 ng) in a sterile centrifuge tube. This mixture is loaded into a chilled electroporation cuvette (gap=2 mm) and placed into the cuvette holder. The electroporator (Gene Pulser Xcell™ Microbial Electroporation Systems; Bio-Rad) is used with the following parameters: 2.5 kV, 25 μF capacitance, and 400 Ohm resistance. One mL SOC medium (20 mM glucose, 20 g/L tryptone, 5 g/L yeast extract, 10 mM NaCl, 2.5 mM $MgCl_2$, and 10 mM $MgSO_4$) is added immediately to the electroporation cuvette and the resulting bacterial suspension transferred into a 15 mL centrifuge tube, and the tube is incubated at 27° C. for 1 h with rotating.

After incubation 100 μl from each suspension of electroporated cells is spread onto LB plates supplemented with kanamycin (50 μg/mL). The plates are incubated for 2 days at 27° C. and successfully transformed colonies verified by plasmid isolation and analytical restriction digests. The following strains are generated:

*A. tumefaciens* LBA 4404 pACYC_rbwA_Srub for production of rubiwettin R1

*A. tumefaciens* LBA 4404 pACYC_rbwAB_Srub for production of rubiwettin RG1

*A. tumefaciens* LBA 4404 pACYC_rhIA_Pa rbwB_Srub for production of rubiwettin RG1

Example 9

Production of rubiwettin R1 with *Agrobacterium tumefaciens* LBA 4404 pACYC_rbwA_Srub and rubiwettin RG1 with *Agrobacterium tumefaciens* LBA 4404 pACYC_rbwAB_Srub and *Agrobacterium tumefaciens* LBA 4404 pACYC_rhIA_Pa rbwB_Srub For the production of rubiwettins R1 and RG1 the DASGIP® parallel bioreactor system from Eppendorf (Hamburg, Germany) is used. The fermentation is performed using 1 L reactors. pH and pO2 are measured online for process monitoring. OTR/CTR measurements served for estimating the metabolic activity and cell fitness, inter alia.

The pH probes are calibrated by means of a two-point calibration with measurement solutions of pH 4.0 and pH 7.0 according to technical reference of DASGIP. The reactors are provided according to technical reference with the required sensors and connections and the stirrer shaft is installed. The reactors are then filled with 300 ml of water and autoclaved for 20 min at 121° C. in order to ensure sterility. The pO2 probes are polarized overnight (at least 6 h) following connection to the measurement amplifier. The water is then removed under the clean bench and replaced by high-cell-density medium consisting of $(NH_4)2504$ 1.76 g/l, $K_2HPO_4$ 19.08 g/l, KH2PO4 12.5 g/l, yeast extracts 6.66 g/l, trisodium citrate dihydrate 11.2 g/l, 17 ml/l of a filter-sterilized 1% strength ammonium iron citrate solution, and 5 ml/l of a filter-sterilized trace element stock solution (consisting of HCl (37%) 36.50 g/l, $MnCl_2$*4H2O 1.91 g/l, $ZnSO_4$*7H2O 1.87 g/l, ethylenediaminetetraacetic acid dihydrate 0.84 g/l, H3BO3 0.30 g/l, Na2MoO4*2H2O0.25 g/l, CaCl2*2H2O 4.70 g/l, FeSO4*7H2O 17.80 g/l, CuCl2*2H2O 0.15 g/l) with 15 g/l glucose as carbon source (added by metered addition of 30 ml/l of a sterile feed solution consisting of 500 g/l glucose, 1% (w/v) MgSO4*7H2O and 2.2% (w/v) NH4Cl) with 50 mg/l kanamycin.

Subsequently, the pO2 probes are calibrated using a single-point calibration (stirrer: 600 rpm/gassing: 10 sL/h air) to 100% and the feed, correction agent and induction agent stretches are cleaned by means of cleaning-in-place according to technical reference. For this, the tubes are firstly flushed with 70% ethanol, then with 1 M NaOH, then with sterile demineralized water and finally filled with the respective media.

For production of rubiwettin R1 with *Agrobacterium tumefaciens* LBA 4404 pACYC_rbwA_Srub as well as production of rubiwettin RG1 with *Agrobacterium tumefaciens* LBA 4404 pACYC_rbwAB_Srub and *Agrobacterium tumefaciens* LBA 4404 pACYC_rhIA_Pa rbwB_Srub, the three strains are cultured firstly from a cryoculture in LB medium (25 ml in a 100 ml baffled shake flask) with 50 mg/l kanamycin overnight at 28° C. and 200 rpm for about 18 h. Then, 2 ml of this culture is transferred for a second preculture stage into 25 ml of high-cell-density medium consisting of (NH4)2504 1.76 g/L, K2HPO4 19.08 g/l, KH2PO4 12.5 g/l, yeast extract 6.66 g/l, trisodium citrate dihydrate 11.2 g/l, 17 ml/l of a filter-sterilized 1% strength ammonium iron citrate solution, and 5 ml/l of a filter-sterilized trace element stock solution (consisting of HCl (37%) 36.50 g/l, MnCl2*4H2O1.91 g/l, ZnSO4*7H2O 1.87 g/l, ethylenediaminetetraacetic acid dihydrate 0.84 g/l, H3BO3 0.30 g/l. Na2MoO4*2H2O 0.25 g/l, CaCl2*2H2O 4.70 g/l, FeSO4*7H2O 17.80 g/l, CuCl2*2H2O 0.15 g/l) with 15 g/l glucose as carbon source (added by metered addition of 30 ml/l of a sterile feed solution consisting of 500 g/l glucose, 1% (w/v) MgSO4*7H2O and 2.2% (w/v) NH4Cl) with the already described antibiotics in a 100 ml shake flask and incubated at 28° C./200 rpm fora further 6 h.

In order to inoculate the reactors with an optical density of 0.1, the 00600 of the second preculture stage is measured and the amount of culture required for the inoculation is calculated. The required amount of culture is added with the help of a 5 ml syringe through a septum into the heat-treated and aerated reactor.

The standard program used is shown in Table 3:

TABLE 3

The standard program for production of rubiwettins with *Agrobacterium* strains

| DO regulator | | pH regulator | |
|---|---|---|---|
| Preset | 0% | Preset | 0 ml/h |
| P | 0.1 | P | 5 |
| Ti | 300 s | Ti | 200 s |
| min | 0% | min | 0 ml/h |
| max | 100% | max | 40 ml/h |

| N (Rotation) | from | to | XO2 (gas mixture) | from | to | F (gas flow rate) | from | to |
|---|---|---|---|---|---|---|---|---|
| growth and | 0% | 30% | growth and | 0% | 100% | growth and | 15% | 80% |
| biotransformation | 400 rpm | 1500 rpm | biotransformation | 21% | 21% | biotransformation | 6 sL/h | 72 sL/h |

| Script | |
|---|---|
| Trigger sharp | 31% DO (1/60 h) |
| Induction Rhamnose | 3 h after feed start |
| Feed trigger | 50% DO |
| Feed rate | 1 [ml/h] |

The pH is regulated to pH 6.8 on one side with 12.5% strength ammonia solution. During cultivation and biotransformation, the dissolved oxygen (pO2 or DO) in the culture is regulated to at least 30% by means of stirrer feed and gassing rate. Following inoculation, the DO drops from 100% to this 30%, where it is kept stable for the remainder of the fermentation. The temperature is kept stable at 28° C.

The fermentation is carried out as fed-batch, where the feed start is triggered as delivery to the feed phase with 1.5 g/l*h glucose feed, consisting of 500 g/l glucose, 1% (w/v) $MgSO_4*7H_2O$ and 2.2% (w/v) $NH_4Cl$, via the DO peak inducing the end of the batch phase. 3 h after the feed start, rubiwettin production is induced with 0.2% (w/v) rhamnose. The inducer concentration refers to the volume at the beginning of fermentation. A rhamnose stock solution of 220 g/L is used. Quantification of formation of rubiwettins R1 and RG1 is performed as described in Example 7.

It is shown that *Agrobacterium tumefaciens* LBA 4404 pACYC_rbwA_Srub produces rubiwettin R1.

It is also shown that *Agrobacterium tumefaciens* LBA 4404 pACYC_rbwAB_Srub and *Agrobacterium tumefaciens* LBA 4404 pACYC_rhIA_Pa rbwB_Srub both produce rubiwettins RG1.

Example 10

Construction of *E. coli* strains for production of rubiwettin R1 and rubiwettin RG1 The plasmids pACYC_rbwA_Srub (SEQ ID NO: 19), pACYC_rbwAB_Srub (SEQ ID NO: 18) and pACYC_rhIA_Pa rbwB_Srub (SEQ ID NO: 21) are transformed via electroporation into *E. coli* W3110 and plated onto LB agar plates with kanamycin (50 μg/ml). Transformants are screened for presence and authenticity of the plasmids by plasmid preparation and restriction digest analysis. The following strains are generated:

*E. coli* W3110 pACYC_rbwA_Srub for production of rubiwettin R1

*E. coli* W3110 pACYC_rbwAB_Srub for production of rubiwettin RG1

*E. coli* W3110 pACYC_rhIA_Pa rbwB_Srub for production of rubiwettin RG1

Example 11

Production of Rubiwettin R1 with *E. coli* W3110 pACYC_rbwA_Srub and Rubiwettin RG1 with *E. coli* W3110 pACYC_rbwAB_Srub and *E. coli* W3110 pACYC_rhIA_Pa rbwB_Srub For the production of rubiwettins R1 and RG1 the DASGIP® parallel bioreactor system from Eppendorf (Hamburg, Germany) is used. The fermentation is performed using 1 L reactors. pH and pO2 are measured online for process monitoring. OTR/CTR measurements served for estimating the metabolic activity and cell fitness, inter alia.

The pH probes are calibrated by means of a two-point calibration with measurement solutions of pH 4.0 and pH 7.0 according to technical reference of DASGIP. The reactors are provided according to technical reference with the required sensors and connections and the stirrer shaft is installed. The reactors are then filled with 300 ml of water and autoclaved for 20 min at 121° C. in order to ensure sterility. The pO2 probes are polarized overnight (at least 6 h) following connection to the measurement amplifier. The water is then removed under the clean bench and replaced by high-cell-density medium consisting of $(NH_4)_2SO_4$ 1.76 g/l, $K_2HPO_4$ 19.08 g/l, $KH_2PO_4$ 12.5 g/l, yeast extracts 6.66 g/l, trisodium citrate dihydrate 11.2 g/l, 17 ml/l of a filter-sterilized 1% strength ammonium iron citrate solution, and 5 ml/l of a filter-sterilized trace element stock solution (consisting of HCl (37%) 36.50 g/l, $MnCl_2*4H_2O$ 1.91 g/l, $ZnSO_4*7H_2O$ 1.87 g/l, ethylenediaminetetraacetic acid dihydrate 0.84 g/l, $H_3BO_3$ 0.30 g/l, $Na_2MoO_4*2H_2O$ 0.25 g/l, $CaCl_2*2H_2O$ 4.70 g/l, $FeSO_4*7H_2O$ 17.80 g/l, $CuCl_2*2H_2O$ 0.15 g/l) with 15 g/l glucose as carbon source (added by metered addition of 30 ml/l of a sterile feed solution consisting of 500 g/l glucose, 1% (w/v) $MgSO_4*7H_2O$ and 2.2% (w/v) $NH_4Cl$) with 50 mg/l kanamycin.

Subsequently, the pO2 probes are calibrated using a single-point calibration (stirrer: 600 rpm/gassing: 10 sL/h air) to 100% and the feed, correction agent and induction agent stretches are cleaned by means of cleaning-in-place according to technical reference. For this, the tubes are firstly flushed with 70% ethanol, then with 1 M NaOH, then with sterile demineralized water and finally filled with the respective media.

For production of rubiwettin R1 with *E. coli* W3110 pACYC_rbwA_Srub as well as production of rubiwettin RG1 with *E. coli* W3110 pACYC_rbwAB_Srub and *E. coli* W3110 pACYC_rhIA_Pa rbwB_Srub, the three strains are cultured firstly from a cryoculture in LB medium (25 ml in a 100 ml baffled shake flask) with 50 mg/l kanamycin overnight at 37° C. and 200 rpm for about 18 h. Then, 2 ml of this culture is transferred for a second preculture stage into 25 ml of high-cell-density medium consisting of $(NH_4)2SO_4$ 1.76 g/L, $K_2HPO_4$ 19.08 g/l, $KH_2PO_4$ 12.5 g/l, yeast extract 6.66 g/l, trisodium citrate dihydrate 11.2 g/l, 17 ml/l of a filter-sterilized 1% strength ammonium iron citrate solution, and 5 ml/l of a filter-sterilized trace element stock solution (consisting of HCl (37%) 36.50 g/l, $MnCl_2*4H_2O$ 1.91 g/l, $ZnSO_4*7H_2O$ 1.87 g/l, ethylenediaminetetraacetic acid dihydrate 0.84 g/l, $H_3BO_3$ 0.30 g/l. $Na_2MoO_4*2H_2O$ 0.25 g/l, $CaCl_2*2H_2O$ 4.70 g/l, $FeSO_4*7H_2O$ 17.80 g/l, $CuCl_2*2H_2O$ 0.15 g/l) with 15 g/l glucose as carbon source (added by metered addition of 30 ml/l of a sterile feed solution consisting of 500 g/l glucose, 1% (w/v) $MgSO_4*7H_2O$ and 2.2% (w/v) $NH_4Cl$) with the already described antibiotics in a 100 ml shake flask and incubated at 37° C./200 rpm for a further 6 h.

In order to inoculate the reactors with an optical density of 0.1, the 00600 of the second preculture stage is measured and the amount of culture required for the inoculation is calculated. The required amount of culture is added with the help of a 5 ml syringe through a septum into the heat-treated and aerated reactor.

The standard program used is shown in Table 4:

TABLE 4

The standard program for production of rubiwettins with *E. coli* strains

| DO regulator | | pH regulator | |
|---|---|---|---|
| Preset | 0% | Preset | 0 ml/h |
| P | 0.1 | P | 5 |
| Ti | 300 s | Ti | 200 s |
| min | 0% | min | 0 ml/h |
| max | 100% | max | 40 ml/h |

| N (Rotation) | from | to | XO2 (gas mixture) | from | to | F (gas flow rate) | from | to |
|---|---|---|---|---|---|---|---|---|
| growth and | 0% | 30% | growth and | 0% | 100% | growth and | 15% | 80% |
| biotransformation | 400 rpm | 1500 rpm | biotransformation | 21% | 21% | biotransformation | 6 sL/h | 72 sL/h |

| Script | |
|---|---|
| Trigger sharp | 31% DO (1/60 h) |
| Induction | 3 h after feed start |
| Rhamnose | |
| Feed trigger | 50% DO |
| Feed rate | 3 [ml/h] |

The pH is regulated to pH 6.8 on one side with 12.5% strength ammonia solution. During cultivation and biotransformation, the dissolved oxygen (pO2 or DO) in the culture is regulated to at least 30% by means of stirrer feed and gassing rate. Following inoculation, the DO drops from 100% to this 30%, where it is kept stable for the remainder of the fermentation. The temperature is kept stable at 37° C. The fermentation is carried out as fed-batch, where the feed start is triggered as delivery to the feed phase with 5 g/l*h glucose feed, consisting of 500 g/l glucose, 1% (w/v) $MgSO_4*7H_2O$ and 2.2% (w/v) $NH_4Cl$, via the DO peak inducing the end of the batch phase. 3 h after the feed start, rubiwettin production is induced with 0.2% (w/v) rhamnose. The inducer concentration refers to the volume at the beginning of fermentation. A rhamnose stock solution of 220 g/L is used. Quantification of formation of rubiwettins R1 and RG1 is performed as described in Example 7.

It is shown that *E. coli* W3110 pACYC_rbwA_Srub produces rubiwettin R1.

It is also shown that *E. coli* W3110 pACYC_rbwAB_Srub and *E. coli* W3110 pACYC_rhIA_Pa rbwB_Srub both produce rubiwettins RG1.

The invention claimed is:

1. A microbial cell for producing at least one lipid with general formula II from at least one carbon substrate, General Formula II

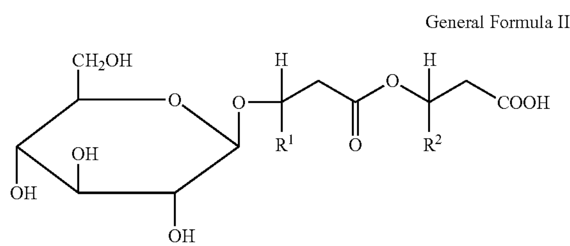

wherein $R^1$ and $R^2$ independently of one another comprise identical or different organic radicals each with 5 to 13 carbon atoms; and wherein the cell is a non-pathogenic cell that is genetically modified to increase the heterologous expression relative to the wild type cell of an enzyme ($E_2$) capable of converting 3-hydroxyalkanoyl-3-hydroxyalkanoyl-CoA/ACP and/or 3-(3-hydroxy-alkanoyloxy)alkanoic acid (HAA) in combination with NDP-glucose into β-D-glucopyranosyl-3-hydroxyalkanoyl-3-hydroxyalkanoate wherein the enzyme $E_2$ is a glycosyltransferase (EC 2.4) comprising SEQ ID NO: 4 or variant thereof, wherein the variant comprises at least 90% sequence identity to SEQ ID NO: 4.

2. The microbial cell of claim 1, wherein the R in the lipid with general formula II is a monounsaturated alkyl radical.

3. The microbial cell of claim 2, wherein the alkyl radical is selected from the group consisting of nonenyl, undecenyl and tridecenyl.

4. The microbial cell of claim 1, wherein the cell is further genetically modified to increase the heterologous expression relative to the wild type cell of an enzyme ($E_1$) capable of converting 3-hydroxyalkanoyl-CoA/ACP into 3-hydroxyalkanoyl-3-hydroxyalkanoyl-CoA/ACP and further to 3-(3-hydroxy-alkanoyloxy)alkanoic acid (HAA).

5. The microbial cell of claim 3, wherein the cell is further genetically modified to increase the heterologous expression relative to the wild type cell of an enzyme ($E_1$) capable of converting 3-hydroxyalkanoyl-CoA/ACP into 3-hydroxyalkanoyl-3-hydroxyalkanoyl-CoA/ACP and further to 3-(3-hydroxy-alkanoyloxy)alkanoic acid (HAA).

6. The microbial cell of claim 4, wherein the enzyme $E_1$ is a 3-(3-hydroxy alkanoyloxy)alkanoic acid (HAA) synthase.

7. The microbial cell of claim 4, wherein the enzyme $E_1$ comprises SEQ ID NO: 2 or variant thereof, wherein the variant comprises at least 90% sequence identity to SEQ ID NO: 2.

8. The microbial cell of claim 6, wherein the enzyme $E_1$ comprises SEQ ID NO: 2 or variant thereof, wherein the variant comprises at least 90% sequence identity to SEQ ID NO: 2.

9. The microbial cell of claim 4, wherein the enzyme $E_1$ comprises a sequence selected from the group consisting of SEQ ID NO: 6, SEQ ID NO: 8, SEQ ID NO: 10, SEQ ID NO: 12, SEQ ID NO: 14 and variants thereof, wherein the variants comprise at least 90% sequence identity to SEQ ID NO: 6, SEQ ID NO: 8, SEQ ID NO: 10, SEQ ID NO: 12 and SEQ ID NO: 14 respectively.

10. The microbial cell of claim 6, wherein the enzyme $E_1$ comprises a sequence selected from the group consisting of SEQ ID NO: 6, SEQ ID NO: 8, SEQ ID NO: 10, SEQ ID NO: 12, SEQ ID NO: 14 and variants thereof, wherein the variants comprise at least 90% sequence identity to SEQ ID NO: 6, SEQ ID NO: 8, SEQ ID NO: 10, SEQ ID NO: 12 and SEQ ID NO: 14 respectively.

11. The microbial cell of claim 1, wherein the cell is genetically modified to increase the expression of: enzyme $E_2$ comprising SEQ ID NO: 4 or a variant thereof, wherein the variant comprises at least 90% sequence identity to SEQ ID NO: 4; and —enzyme $E_1$ comprising SEQ ID NO: 2 or a variant thereof, wherein the variant comprises at least 90% sequence identity to SEQ ID NO: 2.

12. The microbial cell of claim 10, wherein the cell is genetically modified to increase the expression of: enzyme $E_2$ comprising SEQ ID NO: 4 or a variant thereof, wherein the variant comprises at least 90% sequence identity to SEQ ID NO: 4; and —enzyme $E_1$ comprising SEQ ID NO: 2 or a variant thereof, wherein the variant comprises at least 90% sequence identity to SEQ ID NO: 2.

13. The microbial cell claim 1, wherein the cell produces a further lipid with general formula I from the carbon substrate, General Formula I

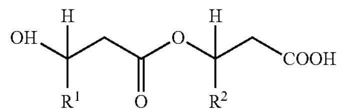

wherein $R^1$ and $R^2$ independently of one another comprise identical or different organic radicals each with 5 to 13 carbon atoms.

14. The microbial cell of claim 13, wherein the R in the lipid with general formula I is a monounsaturated alkyl radical.

15. The microbial cell of claim 1, wherein the carbon source is selected from the group consisting of glucose, dextrose, sucrose, polysaccharides, vegetal oils, animal fats, fatty acids, fatty acid esters, carbonaceous gases, alkanes, glycerol, acetate, ethanol and methanol.

16. The microbial cell of claim 14, wherein the carbon source is selected from the group consisting of glucose, dextrose, sucrose, polysaccharides, vegetal oils, animal fats, fatty acids, fatty acid esters, carbonaceous gases, alkanes, glycerol, acetate, ethanol and methanol.

17. The microbial cell of claim 1, wherein the cell is selected from the group consisting of *Acinetobacter* sp., *Bacillus* sp., *Brevibacterium* sp., *Burkholderia* sp., *Chlorella* sp., *Clostridium* sp., *Corynebacterium* sp., *Cyanobakterien, Escherichia* sp., *Pseudomonas* sp., *Klebsiella* sp., *Salmonella* sp., *Rhizobium* sp., *Saccharomyces* sp., *Pichia* sp., and *Nostoc* sp.

18. A method of producing at least one lipid with general formula II and/or general formula I:

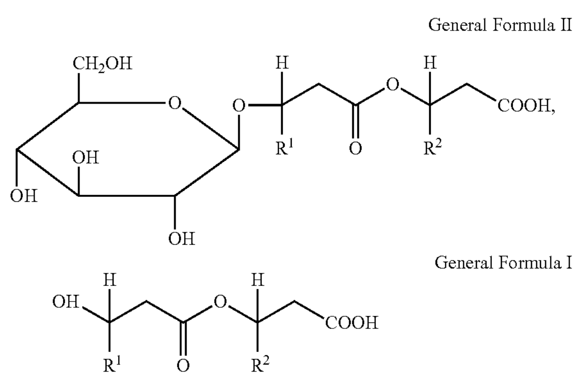

wherein IV and $R^2$ independently of one another comprise identical or different organic radicals each with 5 to 13 carbon atoms; and wherein the method comprises a step of contacting at least one microbial cell of claim 1 with at least one carbon source.

* * * * *

UNITED STATES PATENT AND TRADEMARK OFFICE

CERTIFICATE OF CORRECTION

PATENT NO. : 11,236,372 B2
APPLICATION NO. : 16/968586
DATED : February 1, 2022
INVENTOR(S) : Wessel et al.

It is certified that error appears in the above-identified patent and that said Letters Patent is hereby corrected as shown below:

In the Specification

Column 17, Lines 53-54, the first sentence of paragraph 4 under Example 1 should be a header, Beginning with "Construction of an..", Column 18, Line 14, --DH5c-- is corrected to read --DH5α--, Column 18, Lines 33-34, the first sentence of paragraph 1 under Example 2 should be a header, Beginning with "Construction of an..", Column 18, Line 44, --DH5a-- is corrected to read --DH5α--, Column 18, Line 64, --rh/A-- is corrected to read --rhIA--, Column 19, Line 17, --rh/A-- is corrected to read --rhIA--, Column 19, Line 26, --DH5c-- is corrected to read --DH5α--, Column 19, Line 42, --rbwB_S rub-- is corrected to read --rbwB_Srub--, Column 20, Line 39, --$CoCl_2$ x $H_2O$-- is corrected to read --$CoCl_2$ x $6H_2O$--, Column 20, Line 45, --00600-- is corrected to read --$OD_{600}$--, Column 22, Line 23, --$MnCl_2$ x $H_2O$-- is corrected to read --$MnCl_2$ x $4H_2O$--, Column 22, Line 50, --00600-- is corrected to read --$OD_{600}$--, Column 23, Lines 58 and 61, --00600-- is corrected to read --$OD_{600}$--, Signed and Sealed this
Thirteenth Day of June, 2023

Katherine Kelly Vidal

Katherine Kelly Vidal
*Director of the United States Patent and Trademark Office*

Column 26, Line 20, --$(NH_4)$2504-- is corrected to read --$(NH_4)$2S04--,

Column 26, Line 28, --2H2O0.25-- is corrected to read --2H2O 0.25--,

Column 26, Line 53, --(NH4)2504-- is corrected to read --(NH4)2SO4--,

Column 26, Line 57, --MnCl2*4H2O1.91-- is corrected to read --MnCl2*4H2O 1.91--, Column 27, Line 2, --00600-- is corrected to read --$OD_{600}$--, Column 30, Line 11, --00600-- is corrected to read --$OD_{600}$--.

SEQUENCE LISTING

```
<160> NUMBER OF SEQ ID NOS: 21

<210> SEQ ID NO 1
<211> LENGTH: 840
```

```
<212> TYPE: DNA
<213> ORGANISM: Serratia rubidaea ATCC 27593
<220> FEATURE:
<221> NAME/KEY: rbwA
<222> LOCATION: (1)..(840)

<400> SEQUENCE: 1

atgaaaccag aaacagaaat tgttcgcgtc ggtgactggc aggtctatgt agagcgatat     60

atttatccag gcgtcacgga ttccgtcatt tgcgttaatg gatctttttc aaccacgctg    120

gcttttcgca gctgcgtacg taacttcaag aaccgggtta acgtcattct cttcgatctg    180

ccgttcctcg gtcagtcccg tgagcataat gatttaacca aaccgctgtc gaaaaccgat    240

gaggttttca ttctgcagag tttgattaac cattatgaac cgtcttatct gctctccatc    300

tcctggggcg gactggcagc attgatggcg ctctcctccc gccctcgctc catccgcaaa    360

gccgtggtgg cctcgttctc caccaaggtg aacgacgcga tgaattacta cgtcagtcag    420

ggcaagaaat tactggatga aggcaaaggc gatgaagcgg cgatgctgct caataccgag    480

gttggcaaat atctgccgaa tctgttgaag caggtgaact acgaacactt gagacagttt    540

gacgaatcag cgcaaaaaca ggtgcgttac cacgtcgcgc aaattaccga atttaatcag    600

gcggactata tcgatacctt ccggcaaatc gatacgccga tactgttcat caacggcgag    660

caggacgaat acactacagc gcaagatatt aaggaactca gtaactatat caataactgc    720

gaatttatta ccgtaccgca ggctggccac tttatttata tggaaagccg ctttgcggcc    780

gattatttca acgacgtgat gaacggtttt ctgtttgttg aagaagcgat ggcctcctga    840


<210> SEQ ID NO 2
<211> LENGTH: 279
<212> TYPE: PRT
<213> ORGANISM: Serratia rubidaea
<220> FEATURE:
<221> NAME/KEY: RbwA, 3-(3-hydroxyalkanoyloxy)alkanoic acids (HAAs)
      synthase
<222> LOCATION: (1)..(279)

<400> SEQUENCE: 2

Met Lys Pro Glu Thr Glu Ile Val Arg Val Gly Asp Trp Gln Val Tyr
1               5                   10                  15

Val Glu Arg Tyr Ile Tyr Pro Gly Val Thr Asp Ser Val Ile Cys Val
            20                  25                  30

Asn Gly Ser Phe Ser Thr Thr Leu Ala Phe Arg Ser Cys Val Arg Asn
        35                  40                  45

Phe Lys Asn Arg Val Asn Val Ile Leu Phe Asp Leu Pro Phe Leu Gly
    50                  55                  60

Gln Ser Arg Glu His Asn Asp Leu Thr Lys Pro Leu Ser Lys Thr Asp
65                  70                  75                  80

Glu Val Phe Ile Leu Gln Ser Leu Ile Asn His Tyr Glu Pro Ser Tyr
                85                  90                  95

Leu Leu Ser Ile Ser Trp Gly Gly Leu Ala Ala Leu Met Ala Leu Ser
            100                 105                 110

Ser Arg Pro Arg Ser Ile Arg Lys Ala Val Val Ala Ser Phe Ser Thr
        115                 120                 125

Lys Val Asn Asp Ala Met Asn Tyr Tyr Val Ser Gln Gly Lys Lys Leu
    130                 135                 140

Leu Asp Glu Gly Lys Gly Asp Glu Ala Ala Met Leu Leu Asn Thr Glu
145                 150                 155                 160

Val Gly Lys Tyr Leu Pro Asn Leu Leu Lys Gln Val Asn Tyr Glu His
```

```
                165                 170                 175

Leu Arg Gln Phe Asp Glu Ser Ala Gln Lys Gln Val Arg Tyr His Val
            180                 185                 190

Ala Gln Ile Thr Glu Phe Asn Gln Ala Asp Tyr Ile Asp Thr Phe Arg
        195                 200                 205

Gln Ile Asp Thr Pro Ile Leu Phe Ile Asn Gly Glu Gln Asp Glu Tyr
    210                 215                 220

Thr Thr Ala Gln Asp Ile Lys Glu Leu Ser Asn Tyr Ile Asn Asn Cys
225                 230                 235                 240

Glu Phe Ile Thr Val Pro Gln Ala Gly His Phe Ile Tyr Met Glu Ser
                245                 250                 255

Arg Phe Ala Ala Asp Tyr Phe Asn Asp Val Met Asn Gly Phe Leu Phe
            260                 265                 270

Val Glu Glu Ala Met Ala Ser
        275


<210> SEQ ID NO 3
<211> LENGTH: 1176
<212> TYPE: DNA
<213> ORGANISM: Serratia rubidaea ATCC 27593
<220> FEATURE:
<221> NAME/KEY: rbwB
<222> LOCATION: (1)..(1176)

<400> SEQUENCE: 3

atgagagtga taatatgcgc cctggggtcc tctggcgatg tttacccatg catcgaaatt      60

ggcgcgatat taaaagaaag aaaccatgat gtgcatatac ttaccaatga atacttcaaa     120

gattacgttg agtctcgcaa tctttccttt tcagcagtag gcagtaaaga ggactttatc     180

cgttcagtac gtgacagcca gctatgggag aagaaaacct cattaataaa aatatctgca     240

tacatggcta attatcaggt tggtatgttt cattcaatcg agaggttggt aaatgataat     300

tgtgtaatta ttcattctct ttgggtattc tcagccaagg tggttagcga aaaatattcg     360

ttaaaacgat tcccgataag ccttaccaac gccaacctta aactctgccc ggggaaattt     420

attagctggt tggaaagaaa gctcggcacc tcattgaacc tgaaggctga actctttaga     480

cgccgcctgg tttctccgct gttacaggag gtcatcgcct cgataagaaa atcagagaac     540

ctcccagccg ataaaaacat ctataccgac ctggtagata ggcgcttgaa tcctattatt     600

ttgtatgagc cttggttcta cgaaaaaaaa ccgcagcacg gattttatat ggggttcctg     660

ttaaataaaa accggacatt agaccacgct ccgataatca accgctttgt ggacaaaaaa     720

acggtggttt tcttcaccag ttgggcattg tctgatgaag caggcataaa tcatgtctta     780

agcagtctga aagatgaagg tttgaaatgt gtactggtca cccccaccct cgacagcatc     840

cacgttgaag aaaatgtcat cagaacacct taccttaata tggatagcat caaaggatgt     900

ctgtttgcca ttcaccacgg cggcatcggc accagtgccc aactgcttaa aaacggcata     960

cctcagttaa tctacccaaa agcctttgat cagttcgaaa acgcaagctc tctcgaaaga    1020

ataggctgtg gcgttaaagg cggcgatata aatgcgttga ggcatatgat taaaaagtcg    1080

gttaccaatg ataataactg tgctttttac gcctcgcggc taagtgaaga gaacaaagaa    1140

cgaaacgatg cgctggaacg tttactcatg ggttaa                              1176


<210> SEQ ID NO 4
<211> LENGTH: 391
<212> TYPE: PRT
<213> ORGANISM: Serratia rubidaea
```

```
<220> FEATURE:
<221> NAME/KEY: RbwB
<222> LOCATION: (1)..(391)

<400> SEQUENCE: 4

Met Arg Val Ile Ile Cys Ala Leu Gly Ser Ser Gly Asp Val Tyr Pro
1               5                   10                  15

Cys Ile Glu Ile Gly Ala Ile Leu Lys Glu Arg Asn His Asp Val His
            20                  25                  30

Ile Leu Thr Asn Glu Tyr Phe Lys Asp Tyr Val Glu Ser Arg Asn Leu
        35                  40                  45

Ser Phe Ser Ala Val Gly Ser Lys Glu Asp Phe Ile Arg Ser Val Arg
    50                  55                  60

Asp Ser Gln Leu Trp Glu Lys Lys Thr Ser Leu Ile Lys Ile Ser Ala
65                  70                  75                  80

Tyr Met Ala Asn Tyr Gln Val Gly Met Phe His Ser Ile Glu Arg Leu
                85                  90                  95

Val Asn Asp Asn Cys Val Ile Ile His Ser Leu Trp Val Phe Ser Ala
            100                 105                 110

Lys Val Val Ser Glu Lys Tyr Ser Leu Lys Arg Phe Pro Ile Ser Leu
        115                 120                 125

Thr Asn Ala Asn Leu Lys Leu Cys Pro Gly Lys Phe Ile Ser Trp Leu
    130                 135                 140

Glu Arg Lys Leu Gly Thr Ser Leu Asn Leu Lys Ala Glu Leu Phe Arg
145                 150                 155                 160

Arg Arg Leu Val Ser Pro Leu Leu Gln Glu Val Ile Ala Ser Ile Arg
                165                 170                 175

Lys Ser Glu Asn Leu Pro Ala Asp Lys Asn Ile Tyr Thr Asp Leu Val
            180                 185                 190

Asp Arg Arg Leu Asn Pro Ile Ile Leu Tyr Glu Pro Trp Phe Tyr Glu
        195                 200                 205

Lys Lys Pro Gln His Gly Phe Tyr Met Gly Phe Leu Leu Asn Lys Asn
    210                 215                 220

Arg Thr Leu Asp His Ala Pro Ile Ile Asn Arg Phe Val Asp Lys Lys
225                 230                 235                 240

Thr Val Val Phe Phe Thr Ser Trp Ala Leu Ser Asp Glu Ala Gly Ile
                245                 250                 255

Asn His Val Leu Ser Ser Leu Lys Asp Glu Gly Leu Lys Cys Val Leu
            260                 265                 270

Val Thr Pro Thr Leu Asp Ser Ile His Val Glu Glu Asn Val Ile Arg
        275                 280                 285

Thr Pro Tyr Leu Asn Met Asp Ser Ile Lys Gly Cys Leu Phe Ala Ile
    290                 295                 300

His His Gly Gly Ile Gly Thr Ser Ala Gln Leu Leu Lys Asn Gly Ile
305                 310                 315                 320

Pro Gln Leu Ile Tyr Pro Lys Ala Phe Asp Gln Phe Glu Asn Ala Ser
                325                 330                 335

Ser Leu Glu Arg Ile Gly Cys Gly Val Lys Gly Gly Asp Ile Asn Ala
            340                 345                 350

Leu Arg His Met Ile Lys Lys Ser Val Thr Asn Asp Asn Asn Cys Ala
        355                 360                 365

Phe Tyr Ala Ser Arg Leu Ser Glu Glu Asn Lys Glu Arg Asn Asp Ala
    370                 375                 380

Leu Glu Arg Leu Leu Met Gly
```

```
385                 390

<210> SEQ ID NO 5
<211> LENGTH: 888
<212> TYPE: DNA
<213> ORGANISM: Pseudomonas aeruginosa
<220> FEATURE:
<221> NAME/KEY: rhamnosyltransferase 1, rhlA
<222> LOCATION: (1)..(888)

<400> SEQUENCE: 5

atgcggcgcg aaagtctgtt ggtatcggtt tgcaagggcc tgcgggtaca tgtcgagcgc      60

gttgggcagg atcccgggcg cagcacggtg atgctggtca acggcgcgat ggcgaccacc     120

gcctcgttcg cccggacctg caagtgcctg gccgaacatt tcaacgtggt gctgttcgac     180

ctgcccttcg ccgggcagtc gcgtcagcac aacccgcagc gggggttgat caccaaggac     240

gacgaggtgg aaatcctcct ggcgctgatc gagcgcttcg aggtcaatca cctggtctcc     300

gcgtcctggg gcggtatctc cacgctgctg gcgctgtcgc gcaatccgcg cggcatccgc     360

agctcggtgg tgatggcatt cgcccctgga ctgaaccagg cgatgctcga ctacgtcggg     420

cgggcgcagg cgctgatcga gctggacgac aagtcggcga tcggccatct gctcaacgag     480

accgtcggca aatacctgcc gccgcgcctg aaagccagca accatcagca catggcttcg     540

ctggccaccg gcgaatacga gcaggcgcgc tttcacatcg accaggtgct ggcgctcaac     600

gatcggggct acctggcttg cctggagcgg atccagagcc acgtgcattt catcaacggc     660

agctgggacg aatacaccac cgccgaggac gcccgccagt tccgcgacta cctgccgcac     720

tgcagtttct cgcgggtgga gggcaccggg catttcctcg acctggagtc caagctggcc     780

gcggtacgcg tgcaccgcgc cctgctcgag cacctgctga agcaaccgga gccgcagcgg     840

gcggaacgcg cggcgggatt ccacgagatg gccatcggct acgcctga                  888


<210> SEQ ID NO 6
<211> LENGTH: 295
<212> TYPE: PRT
<213> ORGANISM: Pseudomonas aeruginosa
<220> FEATURE:
<221> NAME/KEY: RhlA
<222> LOCATION: (1)..(295)

<400> SEQUENCE: 6

Met Arg Arg Glu Ser Leu Leu Val Ser Val Cys Lys Gly Leu Arg Val
1               5                   10                  15

His Val Glu Arg Val Gly Gln Asp Pro Gly Arg Ser Thr Val Met Leu
            20                  25                  30

Val Asn Gly Ala Met Ala Thr Thr Ala Ser Phe Ala Arg Thr Cys Lys
        35                  40                  45

Cys Leu Ala Glu His Phe Asn Val Val Leu Phe Asp Leu Pro Phe Ala
    50                  55                  60

Gly Gln Ser Arg Gln His Asn Pro Gln Arg Gly Leu Ile Thr Lys Asp
65                  70                  75                  80

Asp Glu Val Glu Ile Leu Leu Ala Leu Ile Glu Arg Phe Glu Val Asn
                85                  90                  95

His Leu Val Ser Ala Ser Trp Gly Gly Ile Ser Thr Leu Leu Ala Leu
            100                 105                 110

Ser Arg Asn Pro Arg Gly Ile Arg Ser Ser Val Val Met Ala Phe Ala
        115                 120                 125

Pro Gly Leu Asn Gln Ala Met Leu Asp Tyr Val Gly Arg Ala Gln Ala
```

```
    130                 135                 140

Leu Ile Glu Leu Asp Asp Lys Ser Ala Ile Gly His Leu Leu Asn Glu
145                 150                 155                 160

Thr Val Gly Lys Tyr Leu Pro Pro Arg Leu Lys Ala Ser Asn His Gln
                165                 170                 175

His Met Ala Ser Leu Ala Thr Gly Glu Tyr Glu Gln Ala Arg Phe His
            180                 185                 190

Ile Asp Gln Val Leu Ala Leu Asn Asp Arg Gly Tyr Leu Ala Cys Leu
        195                 200                 205

Glu Arg Ile Gln Ser His Val His Phe Ile Asn Gly Ser Trp Asp Glu
    210                 215                 220

Tyr Thr Thr Ala Glu Asp Ala Arg Gln Phe Arg Asp Tyr Leu Pro His
225                 230                 235                 240

Cys Ser Phe Ser Arg Val Glu Gly Thr Gly His Phe Leu Asp Leu Glu
                245                 250                 255

Ser Lys Leu Ala Ala Val Arg Val His Arg Ala Leu Leu Glu His Leu
            260                 265                 270

Leu Lys Gln Pro Glu Pro Gln Arg Ala Glu Arg Ala Ala Gly Phe His
        275                 280                 285

Glu Met Ala Ile Gly Tyr Ala
    290                 295

<210> SEQ ID NO 7
<211> LENGTH: 1041
<212> TYPE: DNA
<213> ORGANISM: Burkholderia thailandensis

<400> SEQUENCE: 7

atgcgcggtt ccggcgagtg ggtagccgct gcggcgcgcg tgaggcaggg cgggcagatc     60

gcgcgggagg gcggctacgt ggaggcgtcc atcaagggcg cgggatcagc tcatttgccg    120

agcagatgcg ggagatacgc catgcctatc gagaaacagg tggtagcgct gccgagcgga    180

ctgaaggtcc acgtcgagcg tcatgtgttc gatccggcct tcgagacggt catcctcgtg    240

aacggcgcgc tggcgacgac cgcgtcgttc ggccagacga ttcgctacct gggcgaacgc    300

gtgaacgcgg tgtgcttcga cttgccgtac gcgggccagt cgcgccagca caatccgggc    360

gagtacattc tgacgaagga cgacgaggtg gagattctgc tgcacctggc cgagcggttc    420

gagccgagtt tcctgctgtc ggtgtcgtgg ggcggggtgg cgtcgctgtt cgcgctggcg    480

cgggggtgcg cgagcgtgcg gcgggcggtg atcgcgtcgt tctcgccgtt cctgaacgac    540

gcgatgacgg attacgtgac gcgcgcgcgc gatcacatcg cggcggggga gaacctgaag    600

gcggcgcagt tgctcaacga cacggtgggg cgctacctgc cgcggatcat gaagctgtac    660

aactaccggt atctgacgaa gctgccgcgc accgagcagg accaggtggc gttccacgtc    720

gaccagatcc tgtcgatgcg gccggagcag tacctgccgg aattccgcca gatcggctgc    780

gcggtgaagt tcatcaacgg cgagctggac gagtacacga cggcgtcgga cgtgcggcgg    840

ctggcggcct acgtgcggcg cgcggagttc gcgacgatcc ggcaggcggg gcacttcctg    900

gacctcgagg ggcgtcagca gcaggagcag cttcgcgcgg cgatcctggg cttcttcggc    960

gacgagcggg cgagcgcggc gcgcgacgac gcgcaggacg agacgctcgc gccgctcggt   1020

cagttgccgg cgctgtcgta g                                             1041

<210> SEQ ID NO 8
<211> LENGTH: 346
```

```
<212> TYPE: PRT
<213> ORGANISM: Burkholderia thailandensis

<400> SEQUENCE: 8

Met Arg Gly Ser Gly Glu Trp Val Ala Ala Ala Ala Arg Val Arg Gln
1               5                   10                  15

Gly Gly Gln Ile Ala Arg Glu Gly Gly Tyr Val Glu Ala Ser Ile Lys
            20                  25                  30

Gly Ala Gly Ser Ala His Leu Pro Ser Arg Cys Gly Arg Tyr Ala Met
        35                  40                  45

Pro Ile Glu Lys Gln Val Val Ala Leu Pro Ser Gly Leu Lys Val His
    50                  55                  60

Val Glu Arg His Val Phe Asp Pro Ala Phe Glu Thr Val Ile Leu Val
65                  70                  75                  80

Asn Gly Ala Leu Ala Thr Thr Ala Ser Phe Gly Gln Thr Ile Arg Tyr
                85                  90                  95

Leu Gly Glu Arg Val Asn Ala Val Cys Phe Asp Leu Pro Tyr Ala Gly
            100                 105                 110

Gln Ser Arg Gln His Asn Pro Gly Glu Tyr Ile Leu Thr Lys Asp Asp
        115                 120                 125

Glu Val Glu Ile Leu Leu His Leu Ala Glu Arg Phe Glu Pro Ser Phe
    130                 135                 140

Leu Leu Ser Val Ser Trp Gly Gly Val Ala Ser Leu Phe Ala Leu Ala
145                 150                 155                 160

Arg Gly Cys Ala Ser Val Arg Arg Ala Val Ile Ala Ser Phe Ser Pro
                165                 170                 175

Phe Leu Asn Asp Ala Met Thr Asp Tyr Val Thr Arg Ala Arg Asp His
            180                 185                 190

Ile Ala Ala Gly Glu Asn Leu Lys Ala Ala Gln Leu Leu Asn Asp Thr
        195                 200                 205

Val Gly Arg Tyr Leu Pro Arg Ile Met Lys Leu Tyr Asn Tyr Arg Tyr
    210                 215                 220

Leu Thr Lys Leu Pro Arg Thr Glu Gln Asp Gln Val Ala Phe His Val
225                 230                 235                 240

Asp Gln Ile Leu Ser Met Arg Pro Glu Gln Tyr Leu Pro Glu Phe Arg
                245                 250                 255

Gln Ile Gly Cys Ala Val Lys Phe Ile Asn Gly Glu Leu Asp Glu Tyr
            260                 265                 270

Thr Thr Ala Ser Asp Val Arg Arg Leu Ala Ala Tyr Val Arg Arg Ala
        275                 280                 285

Glu Phe Ala Thr Ile Arg Gln Ala Gly His Phe Leu Asp Leu Glu Gly
    290                 295                 300

Arg Gln Gln Gln Glu Gln Leu Arg Ala Ala Ile Leu Gly Phe Phe Gly
305                 310                 315                 320

Asp Glu Arg Ala Ser Ala Ala Arg Asp Asp Ala Gln Asp Glu Thr Leu
                325                 330                 335

Ala Pro Leu Gly Gln Leu Pro Ala Leu Ser
            340                 345


<210> SEQ ID NO 9
<211> LENGTH: 888
<212> TYPE: DNA
<213> ORGANISM: Pseudomonas aeruginosa

<400> SEQUENCE: 9
```

```
atgcggcgcg aaagtctgtt ggtatcggtt tgcaagggcc tgcgggtaca tgtcgagcgc      60

gttgggcagg atcccgggcg cagcacggtg atgctggtca acggcgcgat ggcgaccacc     120

gcctcgttcg cccggacctg caagtgcctg gccgaacatt tcaacgtggt gctgttcgac     180

ctgcccttcg ccgggcagtc gcgtcagcac aacccgcagc gcgggttgat caccaaggac     240

gacgaggtgg aaatcctcct ggcgctgatc gagcgcttcg aggtcaatca cctggtctcc     300

gcgtcgtggg gcggtatctc cacgctgctg gcgctgtcgc gcaatccgcg cggcatccgc     360

agctcggtgg tgatggcatt cgcccctgga ctgaaccagg cgatgctcga ctacgtcggg     420

cgggcgcagg cgctgatcga gctggacgac aagtcggcga tcggccatct gctcaacgag     480

accgtcggca aatacctgcc gccgcgcctg aaagccagca accatcagca catggcttcg     540

ctggccaccg gcgaatacga gcaggcgcgc tttcacatcg accaggtgct ggcgctcaac     600

gatcggggct acctggcttg cctggagcgg atccagagcc acgtgcattt catcaacggc     660

agctgggacg aatacaccac cgccgaggac gcccgccagt tccgcgacta cctgccgcac     720

tgcagtttct cgcgggtgga gggcaccggg catttcctcg acctggagtc caagctggcc     780

gcggtacgcg tgcaccgcgc cctgctcgag cacctgctga agcaaccgga gccgcagcgg     840

gcggaacgcg cggcgggatt ccacgagatg gccatcggct acgcctga                  888
```

<210> SEQ ID NO 10
<211> LENGTH: 295
<212> TYPE: PRT
<213> ORGANISM: Pseudomonas aeruginosa

<400> SEQUENCE: 10

```
Met Arg Arg Glu Ser Leu Leu Val Ser Val Cys Lys Gly Leu Arg Val
1               5                   10                  15

His Val Glu Arg Val Gly Gln Asp Pro Gly Arg Ser Thr Val Met Leu
            20                  25                  30

Val Asn Gly Ala Met Ala Thr Thr Ala Ser Phe Ala Arg Thr Cys Lys
        35                  40                  45

Cys Leu Ala Glu His Phe Asn Val Val Leu Phe Asp Leu Pro Phe Ala
    50                  55                  60

Gly Gln Ser Arg Gln His Asn Pro Gln Arg Gly Leu Ile Thr Lys Asp
65                  70                  75                  80

Asp Glu Val Glu Ile Leu Leu Ala Leu Ile Glu Arg Phe Glu Val Asn
                85                  90                  95

His Leu Val Ser Ala Ser Trp Gly Gly Ile Ser Thr Leu Leu Ala Leu
            100                 105                 110

Ser Arg Asn Pro Arg Gly Ile Arg Ser Ser Val Val Met Ala Phe Ala
        115                 120                 125

Pro Gly Leu Asn Gln Ala Met Leu Asp Tyr Val Gly Arg Ala Gln Ala
    130                 135                 140

Leu Ile Glu Leu Asp Asp Lys Ser Ala Ile Gly His Leu Leu Asn Glu
145                 150                 155                 160

Thr Val Gly Lys Tyr Leu Pro Pro Arg Leu Lys Ala Ser Asn His Gln
                165                 170                 175

His Met Ala Ser Leu Ala Thr Gly Glu Tyr Glu Gln Ala Arg Phe His
            180                 185                 190

Ile Asp Gln Val Leu Ala Leu Asn Asp Arg Gly Tyr Leu Ala Cys Leu
        195                 200                 205

Glu Arg Ile Gln Ser His Val His Phe Ile Asn Gly Ser Trp Asp Glu
    210                 215                 220
```

```
Tyr Thr Thr Ala Glu Asp Ala Arg Gln Phe Arg Asp Tyr Leu Pro His
225                 230                 235                 240

Cys Ser Phe Ser Arg Val Glu Gly Thr Gly His Phe Leu Asp Leu Glu
                245                 250                 255

Ser Lys Leu Ala Ala Val Arg Val His Arg Ala Leu Leu Glu His Leu
            260                 265                 270

Leu Lys Gln Pro Glu Pro Gln Arg Ala Glu Arg Ala Ala Gly Phe His
        275                 280                 285

Glu Met Ala Ile Gly Tyr Ala
    290                 295
```

<210> SEQ ID NO 11
<211> LENGTH: 888
<212> TYPE: DNA
<213> ORGANISM: Pseudomonas aeruginosa

<400> SEQUENCE: 11

```
atgcggcgcg aaagtctgtt ggtatcggtt tgcaagggcc tgcgggtaca tgtcgagcgc     60

gttgggcagg atcccgggcg cagcacggtg atgctggtca acggcgcgat ggcgaccacc    120

gcctcgttcg cccggacctg caagtgcctg gccgaacatt tcaacgtggt gctgttcgac    180

ctgcccttcg ccgggcagtc gcgtcagcac aacccgcagc gcgggttgat caccaaggac    240

gacgaggtgg aaatcctcct ggcgctgatc gagcgcttcg aggtcaatca cctggtctcc    300

gcgtcctggg gcggtatctc cacgctgctg gcgctgtcgc gcaatccgcg cggcatccgc    360

agctcggtgg tgatggcatt cgcccctgga ctgaaccagg cgatgctcga ctacgtcggg    420

cgggcgcagg cgctgatcga gctggacgac aagtcggcga tcggccatct gctcaacgag    480

accgtcggca aatacctgcc gcagcgcctg aaagccagca accatcagca catggcttcg    540

ctggccaccg gcgaatacga gcaggcgcgc tttcacatcg accaggtgct ggcgctcaac    600

gatcggggct acttggcttg cctggagcgg atccagagcc acgtgcattt catcaacggc    660

agctgggacg aatacaccac cgccgaggac gcccgccagt tccgcgacta cctgccgcac    720

tgcagtttct cgcgggtgga gggcaccggg catttcctcg acctggagtc caagctggca    780

gcggtacgcg tgcaccgcgc cctgctcgag cacctgctga agcaaccgga gccgcagcgg    840

gcggaacgcg cggcgggatt ccacgagatg gccatcggct acgcctga                 888
```

<210> SEQ ID NO 12
<211> LENGTH: 295
<212> TYPE: PRT
<213> ORGANISM: Pseudomonas aeruginosa

<400> SEQUENCE: 12

```
Met Arg Arg Glu Ser Leu Leu Val Ser Val Cys Lys Gly Leu Arg Val
1               5                   10                  15

His Val Glu Arg Val Gly Gln Asp Pro Gly Arg Ser Thr Val Met Leu
            20                  25                  30

Val Asn Gly Ala Met Ala Thr Thr Ala Ser Phe Ala Arg Thr Cys Lys
        35                  40                  45

Cys Leu Ala Glu His Phe Asn Val Val Leu Phe Asp Leu Pro Phe Ala
    50                  55                  60

Gly Gln Ser Arg Gln His Asn Pro Gln Arg Gly Leu Ile Thr Lys Asp
65                  70                  75                  80

Asp Glu Val Glu Ile Leu Leu Ala Leu Ile Glu Arg Phe Glu Val Asn
                85                  90                  95
```

```
His Leu Val Ser Ala Ser Trp Gly Gly Ile Ser Thr Leu Leu Ala Leu
            100                 105                 110

Ser Arg Asn Pro Arg Gly Ile Arg Ser Ser Val Val Met Ala Phe Ala
        115                 120                 125

Pro Gly Leu Asn Gln Ala Met Leu Asp Tyr Val Gly Arg Ala Gln Ala
    130                 135                 140

Leu Ile Glu Leu Asp Asp Lys Ser Ala Ile Gly His Leu Leu Asn Glu
145                 150                 155                 160

Thr Val Gly Lys Tyr Leu Pro Gln Arg Leu Lys Ala Ser Asn His Gln
                165                 170                 175

His Met Ala Ser Leu Ala Thr Gly Glu Tyr Glu Gln Ala Arg Phe His
            180                 185                 190

Ile Asp Gln Val Leu Ala Leu Asn Asp Arg Gly Tyr Leu Ala Cys Leu
        195                 200                 205

Glu Arg Ile Gln Ser His Val His Phe Ile Asn Gly Ser Trp Asp Glu
    210                 215                 220

Tyr Thr Thr Ala Glu Asp Ala Arg Gln Phe Arg Asp Tyr Leu Pro His
225                 230                 235                 240

Cys Ser Phe Ser Arg Val Glu Gly Thr Gly His Phe Leu Asp Leu Glu
                245                 250                 255

Ser Lys Leu Ala Ala Val Arg Val His Arg Ala Leu Leu Glu His Leu
            260                 265                 270

Leu Lys Gln Pro Glu Pro Gln Arg Ala Glu Arg Ala Ala Gly Phe His
        275                 280                 285

Glu Met Ala Ile Gly Tyr Ala
    290                 295
```

<210> SEQ ID NO 13
<211> LENGTH: 888
<212> TYPE: DNA
<213> ORGANISM: Pseudomonas aeruginosa

<400> SEQUENCE: 13

```
atgcggcgcg aaagtctgtt ggtaacggta tgcaagggcc tgcgggtaca tgtcgagcgc     60

gtggggcagg atcccgggcg cgacacggtg atgctggtca acggcgcgat ggcgaccacc    120

gcctcgttcg cccggacctg caagtgcctg gccgaacatt tcaacgtggt gctgttcgac    180

ctgcccttcg ccgggcagtc gcggcagcac aatccgcagc gcgggttgat caccaaggac    240

gacgaggtgg agattctcct ggcgctgatc gagcgcttcg ctgtcaacca cctggtctcg    300

gcctcctggg gcggcatctc cacgctgctg gcgctgtcgc gcaacccgcg cggggtccgc    360

agctcggtgg tgatggcgtt cgcgccgggg ctgaaccagg cgatgctcga ttatgtcggg    420

cgggcccagg aactgatcga actggacgac aagtcggcga tcggccacct gctcaacgag    480

accgtcggca agtacctgcc gccgcggctg aaggccagca accatcagca catggcctcc    540

ctggccactg gcgagtacga gcaggcgcgt ttccacatcg accaggtgct ggcgctcaat    600

gaccgtggct acctgagctg cctggggcag atccagagtc acgtgcattt catcaacggc    660

agctgggacg agtacaccac cgccgaggac gcccgccagt tccgcgatta cctgccgcat    720

tgcagttttt cgcgggtgga aggcaccggg cacttcctcg acctggagtc caagctggcg    780

gcggcgcgtg tgcaccgggc gttgctcgag cacctgctgg cgcaaccgga accgtggcgc    840

tccgagcagg cggcgggatt ccacgagatg gccatcggct acgcctga                 888
```

<210> SEQ ID NO 14
<211> LENGTH: 295
<212> TYPE: PRT
<213> ORGANISM: Pseudomonas aeruginosa

<400> SEQUENCE: 14

```
Met Arg Arg Glu Ser Leu Leu Val Thr Val Cys Lys Gly Leu Arg Val
1               5                   10                  15

His Val Glu Arg Val Gly Gln Asp Pro Gly Arg Asp Thr Val Met Leu
            20                  25                  30

Val Asn Gly Ala Met Ala Thr Thr Ala Ser Phe Ala Arg Thr Cys Lys
        35                  40                  45

Cys Leu Ala Glu His Phe Asn Val Val Leu Phe Asp Leu Pro Phe Ala
    50                  55                  60

Gly Gln Ser Arg Gln His Asn Pro Gln Arg Gly Leu Ile Thr Lys Asp
65                  70                  75                  80

Asp Glu Val Glu Ile Leu Leu Ala Leu Ile Glu Arg Phe Ala Val Asn
                85                  90                  95

His Leu Val Ser Ala Ser Trp Gly Gly Ile Ser Thr Leu Leu Ala Leu
            100                 105                 110

Ser Arg Asn Pro Arg Gly Val Arg Ser Ser Val Val Met Ala Phe Ala
        115                 120                 125

Pro Gly Leu Asn Gln Ala Met Leu Asp Tyr Val Gly Arg Ala Gln Glu
    130                 135                 140

Leu Ile Glu Leu Asp Asp Lys Ser Ala Ile Gly His Leu Leu Asn Glu
145                 150                 155                 160

Thr Val Gly Lys Tyr Leu Pro Pro Arg Leu Lys Ala Ser Asn His Gln
                165                 170                 175

His Met Ala Ser Leu Ala Thr Gly Glu Tyr Glu Gln Ala Arg Phe His
            180                 185                 190

Ile Asp Gln Val Leu Ala Leu Asn Asp Arg Gly Tyr Leu Ser Cys Leu
        195                 200                 205

Gly Gln Ile Gln Ser His Val His Phe Ile Asn Gly Ser Trp Asp Glu
    210                 215                 220

Tyr Thr Thr Ala Glu Asp Ala Arg Gln Phe Arg Asp Tyr Leu Pro His
225                 230                 235                 240

Cys Ser Phe Ser Arg Val Glu Gly Thr Gly His Phe Leu Asp Leu Glu
                245                 250                 255

Ser Lys Leu Ala Ala Ala Arg Val His Arg Ala Leu Leu Glu His Leu
            260                 265                 270

Leu Ala Gln Pro Glu Pro Trp Arg Ser Glu Gln Ala Ala Gly Phe His
        275                 280                 285

Glu Met Ala Ile Gly Tyr Ala
    290                 295
```

<210> SEQ ID NO 15
<211> LENGTH: 2084
<212> TYPE: DNA
<213> ORGANISM: Artificial Sequence
<220> FEATURE:
<223> OTHER INFORMATION: Synthetical operon rbwAB

<400> SEQUENCE: 15

```
tcatgggggt gggaaatgaa accagaaaca gaaattgttc gcgtcggtga ctggcaggtc      60

tatgtagagc gatatattta tccaggcgtc acggattccg tcatttgcgt taatggatct     120

ttttcaacca cgctggcttt tcgcagctgc gtacgtaact tcaagaaccg ggttaacgtc     180
```

```
attctcttcg atctgccgtt cctcggtcag tcccgtgagc ataatgattt aaccaaaccg    240
ctgtcgaaaa ccgatgaggt tttcattctg cagagtttga ttaaccatta tgaaccgtct    300
tatctgctct ccatctcctg gggcggactg gcagcattga tggcgctctc ctcccgccct    360
cgctccatcc gcaaagccgt ggtggcctcg ttctccacca aggtgaacga cgcgatgaat    420
tactacgtca gtcagggcaa gaaattactg gatgaaggca aaggcgatga agcggcgatg    480
ctgctcaata ccgaggttgg caaatatctg ccgaatctgt tgaagcaggt gaactacgaa    540
cacttgagac agtttgacga atcagcgcaa aaacaggtgc gttaccacgt cgcgcaaatt    600
accgaattta atcaggcgga ctatatcgat accttccggc aaatcgatac gccgatactg    660
ttcatcaacg gcgagcagga cgaatacact acagcgcaag atattaagga actcagtaac    720
tatatcaata actgcgaatt tattaccgta ccgcaggctg gccactttat ttatatggaa    780
agccgctttg cggccgatta tttcaacgac gtgatgaacg gttttctgtt tgttgaagaa    840
gcgatggcct cctgaggata acaaactaaa atattgattc gacaagacag gatggtgata    900
tgagagtgat aatatgcgcc ctggggtcct ctggcgatgt ttacccatgc atcgaaattg    960
gcgcgatatt aaaagaaaga aaccatgatg tgcatatact taccaatgaa tacttcaaag   1020
attacgttga gtctcgcaat ctttcctttt cagcagtagg cagtaaagag gactttatcc   1080
gttcagtacg tgacagccag ctatgggaga agaaaacctc attaataaaa atatctgcat   1140
acatggctaa ttatcaggtt ggtatgtttc attcaatcga gaggttggta aatgataatt   1200
gtgtaattat tcattctctt tgggtattct cagccaaggt ggttagcgaa aaatattcgt   1260
taaaacgatt cccgataagc cttaccaacg ccaaccttaa actctgcccg ggaaatttta   1320
ttagctggtt ggaaagaaag ctcggcacct cattgaacct gaaggctgaa ctctttagac   1380
gccgcctggt ttctccgctg ttacaggagg tcatcgcctc gataagaaaa tcagagaacc   1440
tcccagccga taaaaacatc tataccgacc tggtagatag gcgcttgaat cctattattt   1500
tgtatgagcc ttggttctac gaaaaaaaac cgcagcacgg attttatatg gggttcctgt   1560
taaataaaaa ccggacatta gaccacgctc cgataatcaa ccgctttgtg gacaaaaaaa   1620
cggtggtttt cttcaccagt tgggcattgt ctgatgaagc aggcataaat catgtcttaa   1680
gcagtctgaa agatgaaggt ttgaaatgtg tactggtcac ccccaccctc gacagcatcc   1740
acgttgaaga aaatgtcatc agaacacctt accttaatat ggatagcatc aaaggatgtc   1800
tgtttgccat tcaccacggc ggcatcggca ccagtgccca actgcttaaa aacggcatac   1860
ctcagttaat ctacccaaaa gcctttgatc agttcgaaaa cgcaagctct ctcgaaagaa   1920
taggctgtgg cgttaaaggc ggcgatataa atgcgttgag gcatatgatt aaaaagtcgg   1980
ttaccaatga taataactgt gctttttacg cctcgcggct aagtgaagag aacaaagaac   2040
gaaacgatgc gctggaacgt ttactcatgg gttaagctcg agca                     2084
```

<210> SEQ ID NO 16
<211> LENGTH: 2028
<212> TYPE: DNA
<213> ORGANISM: Artificial Sequence
<220> FEATURE:
<223> OTHER INFORMATION: Promoter cassette Prha

<400> SEQUENCE: 16

```
ttaatctttc tgcgaattga gatgacgcca ctggctgggc gtcatcccgg tttcccgggt     60
aaacaccacc gaaaaatagt tactatcttc aaagccacat tcggtcgaaa tatcactgat    120
```

```
taacaggcgg ctatgctgga gaagatattg cgcatgacac actctgacct gtcgcagata    180

ttgattgatg gtcattccag tctgctggcg aaattgctga cgcaaaacgc gctcactgca    240

cgatgcctca tcacaaaatt tatccagcgc aaagggactt ttcaggctag ccgccagccg    300

ggtaatcagc ttatccagca acgtttcgct ggatgttggc ggcaacgaat cactggtgta    360

acgatggcga ttcagcaaca tcaccaactg cccgaacagc aactcagcca tttcgttagc    420

aaacggcaca tgctgactac tttcatgctc aagctgaccg ataacctgcc gcgcctgcgc    480

catccccatg ctacctaagc gccagtgtgg ttgccctgcg ctggcgttaa atcccggaat    540

cgccccctgc cagtcaagat tcagcttcag acgctccggg caataaataa tattctgcaa    600

aaccagatcg ttaacggaag cgtaggagtg tttatcgtca gcatgaatgt aaaagagatc    660

gccacgggta atgcgataag ggcgatcgtt gagtacatgc aggccattac cgcgccagac    720

aatcaccagc tcacaaaaat catgtgtatg ttcagcaaag acatcttgcg gataacggtc    780

agccacagcg actgcctgct ggtcgctggc aaaaaaatca tctttgagaa gttttaactg    840

atgcgccacc gtggctacct cggccagaga acgaagttga ttattcgcaa tatggcgtac    900

aaatacgttg agaagattcg cgttattgca gaaagccatc ccgtccctgg cgaatatcac    960

gcggtgacca gttaaactct cggcgaaaaa gcgtcgaaaa gtggttactg tcgctgaatc   1020

cacagcgata ggcgatgtca gtaacgctgg cctcgctgtg gcgtagcaga tgtcgggctt   1080

tcatcagtcg caggcggttc aggtatcgct gaggcgtcag tcccgtttgc tgcttaagct   1140

gccgatgtag cgtacgcagt gaaagagaaa attgatccgc cacggcatcc caattcacct   1200

catcggcaaa atggtcctcc agccaggcca gaagcaagtt gagacgtgat gcgctgtttt   1260

ccaggttctc ctgcaaactg cttttacgca gcaagagcag taattgcata aacaagatct   1320

cgcgactggc ggtcgagggt aaatcatttt ccccttcctg ctgttccatc tgtgcaacca   1380

gctgtcgcac ctgctgcaat acgctgtggt taacgcgcca gtgagacgga tactgcccat   1440

ccagctcttg tggcagcaac tgattcagcc cggcgagaaa ctgaaatcga tccggcgagc   1500

gatacagcac attggtcaga cacagattat cggtatgttc atacagatgc cgatcatgat   1560

cgcgtacgaa acagaccgtg ccaccggtga tggtataggg ctgcccatta aacacatgaa   1620

tacccgtgcc atgttcgaca atcacaattt catgaaaatc atgatgatgt tcaggaaaat   1680

ccgcctgcgg gagccggggt tctatcgcca cggacgcgtt accagacgga aaaaaatcca   1740

cactatgtaa tacggtcata ctggcctcct gatgtcgtca acacggcgaa atagtaatca   1800

cgaggtcagg ttcttacctt aaattttcga cggaaaacca cgtaaaaaac gtcgattttt   1860

caagatacag cgtgaatttt caggaaatgc ggtgagcatc acatcaccac aattcagcaa   1920

attgtgaaca tcatcacgtt catctttccc tggttgccaa tggcccattt tcctgtcagt   1980

aacgagaagg tcgcgaattc aggcgctttt tagactggtc gtaatgaa                2028
```

<210> SEQ ID NO 17
<211> LENGTH: 107
<212> TYPE: DNA
<213> ORGANISM: Artificial Sequence
<220> FEATURE:
<223> OTHER INFORMATION: Terminator sequence

<400> SEQUENCE: 17

```
caaataaaac gaaaggctca gtcgaaagac tgggcctttc gttttatctg ttgtttgtcg     60

gtgaacgctc tcctgagtag gacaaatccg ccgggagcgg atttgaa                 107
```

<210> SEQ ID NO 18
<211> LENGTH: 10738
<212> TYPE: DNA
<213> ORGANISM: Artificial Sequence
<220> FEATURE:
<223> OTHER INFORMATION: Plasmid pACYC_rbwAB_Srub

<400> SEQUENCE: 18

```
tcaggcgggc aagaatgtga ataaaggccg gataaaactt gtgcttattt ttctttacgg     60
tctttaaaaa ggccgtaata tccagctgaa cggtctggtt ataggtacat tgagcaactg    120
actgaaatgc ctcaaaatgt tctttacgat gccattggga tatatcaacg gtggtatatc    180
cagtgatttt tttctccatt ttagcttcct tagctcctga aaatctcgat aactcaaaaa    240
atacgcccgg tagtgatctt atttcattat ggtgaaagtt ggaacctctt acgtgccgat    300
caacgtctca ttttcgccaa aagttggccc agggcttccc ggtatcaaca gggacaccag    360
gatttattta ttctgcgaag tgatcttccg tcacaggtat ttattcggcg caaagtgcgt    420
cgggtgatgc tgccaactta ctgatttagt gtatgatggt gtttttgagg tgctccagtg    480
gcttctgttt ctatcagctg tccctcctgt tcagctactg acggggtggt gcgtaacggc    540
aaaagcaccg ccggacatca gcgctagcgg agtgtatact ggcttactat gttggcactg    600
atgagggtgt cagtgaagtg cttcatgtgg caggagaaaa aaggctgcac cggtgcgtca    660
gcagaatatg tgatacagga tatattccgc ttcctcgctc actgactcgc tacgctcggt    720
cgttcgactg cggcgagcgg aaatggctta cgaacggggc ggagatttcc tggaagatgc    780
caggaagata cttaacaggg aagtgagagg gccgcggcaa agccgttttt ccataggctc    840
cgcccccctg acaagcatca cgaaatctga cgctcaaatc agtggtggcg aaacccgaca    900
ggactataaa gataccaggc gtttccccct ggcggctccc tcgtgcgctc tcctgttcct    960
gcctttcggt ttaccggtgt cattccgctg ttatggccgc gtttgtctca ttccacgcct   1020
gacactcagt tccgggtagg cagttcgctc caagctggac tgtatgcacg aaccccccgt   1080
tcagtccgac cgctgcgcct tatccggtaa ctatcgtctt gagtccaacc cggaaagaca   1140
tgcaaaagca ccactggcag cagccactgg taattgattt agaggagtta gtcttgaagt   1200
catgcgccgg ttaaggctaa actgaaagga caagttttgg tgactgcgct cctccaagcc   1260
agttacctcg gttcaaagag ttggtagctc agagaacctt cgaaaaaccg ccctgcaagg   1320
cggttttttc gttttcagag caagagatta cgcgcagacc aaaacgatct caagaagatc   1380
atcttattaa tcagataaaa tatttctaga tttcagtgca atttatctct tcaaatgtag   1440
cacctgaagt cagccccata cgatataagt tgtaattctc atgtttgaca gcttatcatc   1500
gataagcttt aatgcggtag tttatcacag ttaaattgct aacgcagtca ggcaccgtgt   1560
atgattgaac aagatggatt gcacgcaggt tctccggccg cttgggtgga gaggctattc   1620
ggctatgact gggcacaaca gacaatcggc tgctctgatg ccgccgtgtt ccggctgtca   1680
gcgcaggggc gcccggttct ttttgtcaag accgacctgt ccggtgccct gaatgaactg   1740
caggacgagg cagcgcggct atcgtggctg gccacgacgg gcgttccttg cgcagctgtg   1800
ctcgacgttg tcactgaagc gggaagggac tggctgctat tgggcgaagt gccggggcag   1860
gatctcctgt catctcacct tgctcctgcc gagaaagtat ccatcatggc tgatgcaatg   1920
cggcggctgc atacgcttga tccggctacc tgcccattcg accaccaagc gaaacatcgc   1980
atcgagcgag cacgtactcg gatggaagcc ggtcttgtcg atcaggatga tctggacgaa   2040
gagcatcagg ggctcgcgcc agccgaactg ttcgccaggc tcaaggcgcg catgcccgac   2100
```

-continued

```
ggcgaggatc tcgtcgtgac ccatggcgat gcctgcttgc cgaatatcat ggtggaaaat   2160
ggccgctttt ctggattcat cgactgtggc cggctgggtg tggcggaccg ctatcaggac   2220
atagcgttgg ctacccgtga tattgctgaa gagcttggcg gcgaatgggc tgaccgcttc   2280
ctcgtgcttt acggtatcgc cgctcccgat tcgcagcgca tcgccttcta tcgccttctt   2340
gacgagttca tggaagccgg cggcacctcg ctaacggatt caccactcca agaattggag   2400
ccaatcaatt cttgcggaga actgtgaatg cgcaaaccaa cccttggcag aacatatcca   2460
tcgcgtccgc catctccagc agccgcacgc ggcgcatctc gggcagcgtt gggtcctggc   2520
cacgggtgcg catgatcgtg ctcctgtcgt tgaggacccg gctaggctgg cggggttgcc   2580
ttactggtta gcagaatgaa tcaccgatac gcgagcgaac gtgaagcgac tgctgctgca   2640
aaacgtctgc gacctgagca acaacatgaa tggtcttcgg tttccgtgtt tcgtaaagtc   2700
tggaaacgcg gaagtcccct acgtgctgct gaagttgccc gcaacagaga gtggaaccaa   2760
ccggtgatac cacgatacta tgactgagag tcaacgccat gagcggcctc atttcttatt   2820
ctgagttaca acagtccgca ccgctgtccg gtagctcctt ccggtgggcg cggggcatga   2880
ctatcgtcgc cgcacttatg actgtcttct ttatcatgca actcgtagga caggtgccgg   2940
cagcgcccaa cagtcccccg gccacggggc ctgccaccat acccacgccg aaacaagcgc   3000
cctgcaccat tatgttccgg atctgcatcg caggatgctg ctggctaccc tgtggaacac   3060
ctacatctgt attaacgaag cgctaaccgt ttttatcagg ctctgggagg cagaataaat   3120
gatcatatcg tcaattatta cctccacggg gagagcctga gcaaactggc ctcaggcatt   3180
tgagaagcac acggtcacac tgcttccggt agtcaataaa ccggtaaacc agcaatagac   3240
ataagcggct atttaacgac cctgccctga accgacgacc gggtcgaatt tgctttcgaa   3300
tttctgccat tcatccgctt attatcactt attcaggcgt agcaccaggc gtttaagggc   3360
accaataact gccttaaaaa aattacgccc cgccctgcca ctcatcgcag tactgttgta   3420
attcattaag cattctgccg acatggaagc catcacaaac ggcatgatga acctgaatcg   3480
ccagcggcat cagcaccttg tcgccttgcg tataatattt gcccatggat ttaaatttaa   3540
tctttctgcg aattgagatg acgccactgg ctgggcgtca tcccggtttc ccgggtaaac   3600
accaccgaaa aatagttact atcttcaaag ccacattcgg tcgaaatatc actgattaac   3660
aggcggctat gctggagaag atattgcgca tgacacactc tgacctgtcg cagatattga   3720
ttgatggtca ttccagtctg ctggcgaaat tgctgacgca aaacgcgctc actgcacgat   3780
gcctcatcac aaaatttatc cagcgcaaag ggacttttca ggctagccgc cagccgggta   3840
atcagcttat ccagcaacgt ttcgctggat gttggcggca acgaatcact ggtgtaacga   3900
tggcgattca gcaacatcac caactgcccg aacagcaact cagccatttc gttagcaaac   3960
ggcacatgct gactactttc atgctcaagc tgaccgataa cctgccgcgc ctgcgccatc   4020
cccatgctac ctaagcgcca gtgtggttgc cctgcgctgg cgttaaatcc cggaatcgcc   4080
ccctgccagt caagattcag cttcagacgc tccgggcaat aaataatatt ctgcaaaacc   4140
agatcgttaa cggaagcgta ggagtgttta tcgtcagcat gaatgtaaaa gagatcgcca   4200
cgggtaatgc gataagggcg atcgttgagt acatgcaggc cattaccgcg ccagacaatc   4260
accagctcac aaaaatcatg tgtatgttca gcaaagacat cttgcggata acggtcagcc   4320
acagcgactg cctgctggtc gctggcaaaa aaatcatctt tgagaagttt taactgatgc   4380
gccaccgtgg ctacctcggc cagagaacga agttgattat tcgcaatatg gcgtacaaat   4440
acgttgagaa gattcgcgtt attgcagaaa gccatcccgt ccctggcgaa tatcacgcgg   4500
```

```
tgaccagtta aactctcggc gaaaaagcgt cgaaaagtgg ttactgtcgc tgaatccaca   4560
gcgataggcg atgtcagtaa cgctggcctc gctgtggcgt agcagatgtc gggctttcat   4620
cagtcgcagg cggttcaggt atcgctgagg cgtcagtccc gtttgctgct taagctgccg   4680
atgtagcgta cgcagtgaaa gagaaaattg atccgccacg gcatcccaat tcacctcatc   4740
ggcaaaatgg tcctccagcc aggccagaag caagttgaga cgtgatgcgc tgttttccag   4800
gttctcctgc aaactgcttt tacgcagcaa gagcagtaat tgcataaaca agatctcgcg   4860
actggcggtc gagggtaaat cattttcccc ttcctgctgt tccatctgtg caaccagctg   4920
tcgcacctgc tgcaatacgc tgtggttaac gcgccagtga gacggatact gcccatccag   4980
ctcttgtggc agcaactgat tcagcccggc gagaaactga aatcgatccg gcgagcgata   5040
cagcacattg gtcagacaca gattatcggt atgttcatac agatgccgat catgatcgcg   5100
tacgaaacag accgtgccac cggtgatggt atagggctgc ccattaaaca catgaatacc   5160
cgtgccatgt tcgacaatca caatttcatg aaaatcatga tgatgttcag gaaaatccgc   5220
ctgcgggagc cggggttcta tcgccacgga cgcgttacca gacggaaaaa aatccacact   5280
atgtaatacg gtcatactgg cctcctgatg tcgtcaacac ggcgaaatag taatcacgag   5340
gtcaggttct taccttaaat tttcgacgga aaccacgta aaaaaacgtcg atttttcaag   5400
atacagcgtg aattttcagg aaatgcggtg agcatcacat caccacaatt cagcaaattg   5460
tgaacatcat cacgttcatc tttccctggt tgccaatggc ccattttcct gtcagtaacg   5520
agaaggtcgc gaattcaggc gctttttaga ctggtcgtaa tgaacattta aatgaattcc   5580
cttgggactc tagagatccg cggggcccg gcatcatttt attgttattc atgggggtgg   5640
gaaatgaaac cagaaacaga aattgttcgc gtcggtgact ggcaggtcta tgtagagcga   5700
tatatttatc caggcgtcac ggattccgtc atttgcgtta atggatcttt ttcaaccacg   5760
ctggcttttc gcagctgcgt acgtaacttc aagaaccggg ttaacgtcat tctcttcgat   5820
ctgccgttcc tcggtcagtc ccgtgagcat aatgatttaa ccaaaccgct gtcgaaaacc   5880
gatgaggttt tcattctgca gagtttgatt aaccattatg aaccgtctta tctgctctcc   5940
atctcctggg gcggactggc agcattgatg gcgctctcct cccgccctcg ctccatccgc   6000
aaagccgtgg tggcctcgtt ctccaccaag gtgaacgacg cgatgaatta ctacgtcagt   6060
cagggcaaga aattactgga tgaaggcaaa ggcgatgaag cggcgatgct gctcaatacc   6120
gaggttggca aatatctgcc gaatctgttg aagcaggtga actacgaaca cttgagacag   6180
tttgacgaat cagcgcaaaa acaggtgcgt taccacgtcg cgcaaattac cgaatttaat   6240
caggcggact atatcgatac cttccggcaa atcgatacgc cgatactgtt catcaacggc   6300
gagcaggacg aatacactac agcgcaagat attaaggaac tcagtaacta tatcaataac   6360
tgcgaattta ttaccgtacc gcaggctggc cactttattt atatggaaag ccgctttgcg   6420
gccgattatt tcaacgacgt gatgaacggt tttctgtttg ttgaagaagc gatggcctcc   6480
tgaggataac aaactaaaat attgattcga caagacagga tggtgatatg agagtgataa   6540
tatgcgccct ggggtcctct ggcgatgttt acccatgcat cgaaattggc gcgatattaa   6600
aagaaagaaa ccatgatgtg catatactta ccaatgaata cttcaaagat tacgttgagt   6660
ctcgcaatct ttccttttca gcagtaggca gtaaagagga ctttatccgt tcagtacgtg   6720
acagccagct atgggagaag aaaacctcat taataaaaat atctgcatac atggctaatt   6780
atcaggttgg tatgtttcat tcaatcgaga ggttggtaaa tgataattgt gtaattattc   6840
```

-continued

```
attctctttg ggtattctca gccaaggtgg ttagcgaaaa atattcgtta aaacgattcc   6900
cgataagcct taccaacgcc aaccttaaac tctgcccggg gaaatttatt agctggttgg   6960
aaagaaagct cggcacctca ttgaacctga aggctgaact ctttagacgc cgcctggttt   7020
ctccgctgtt acaggaggtc atcgcctcga taagaaaatc agagaacctc ccagccgata   7080
aaaacatcta taccgacctg gtagataggc gcttgaatcc tattattttg tatgagcctt   7140
ggttctacga aaaaaaaccg cagcacggat tttatatggg gttcctgtta aataaaaacc   7200
ggacattaga ccacgctccg ataatcaacc gctttgtgga caaaaaaacg gtggttttct   7260
tcaccagttg ggcattgtct gatgaagcag gcataaatca tgtcttaagc agtctgaaag   7320
atgaaggttt gaaatgtgta ctggtcaccc ccaccctcga cagcatccac gttgaagaaa   7380
atgtcatcag aacaccttac cttaatatgg atagcatcaa aggatgtctg tttgccattc   7440
accacggcgg catcggcacc agtgcccaac tgcttaaaaa cggcatacct cagttaatct   7500
acccaaaagc ctttgatcag ttcgaaaacg caagctctct cgaaagaata ggctgtggcg   7560
ttaaaggcgg cgatataaat gcgttgaggc atatgattaa aaagtcggtt accaatgata   7620
ataactgtgc tttttacgcc tcgcggctaa gtgaagagaa caaagaacga aacgatgcgc   7680
tggaacgttt actcatgggt taagctcgag cacgcgagag tagggaactg ccaggcatca   7740
aataaaacga aaggctcagt cgaaagactg ggcctttcgt tttatctgtt gtttgtcggt   7800
gaacgctctc ctgagtagga caaatccgcc gggagcggat ttgaacgatg ataagctgtc   7860
aaacatgaga attcttgaag acgaaagggc ctcgtgtgta caaacgttcg tcaaaagggc   7920
gacacaaaat tcctgcaggg gccggcccag cgccggcggt cgagtggcga cggcgcggct   7980
tgtccgcgcc ctggtagatt gcctggccgt aggccagcca tttttgagcg gccagcggcc   8040
gcgataggcc gacgcgaagc ggcggggcgt agggagcgca gcgaccgaag ggtaggcgct   8100
ttttgcagct cttcggctgt gcgctggcca gacagttatg cacaggccag gcgggtttta   8160
agagttttaa taagttttaa agagttttag gcggaaaaat cgcctttttt ctcttttata   8220
tcagtcactt acatgtgtga ccggttccca atgtacggct ttgggttccc aatgtacggg   8280
ttccggttcc caatgtacgg ctttgggttc ccaatgtacg tgctatccac aggaaagaga   8340
ccttttcgac ctttttcccc tgctagggca atttgcccta gcatctgctc cgtacattag   8400
gaaccggcgg atgcttcgcc ctcgatcagg ttgcggtagc gcatgactag gatcgggcca   8460
gcctgccccg cctcctcctt caaatcgtac tccggcaggt catttgaccc gatcagcttg   8520
cgcacggtga aacagaactt cttgaactct ccggcgctgc cactgcgttc gtagatcgtc   8580
ttgaacaacc atctggcttc tgccttgcct gcggcgcggc gtgccaggcg gtagagaaaa   8640
cggccgatgc cgggatcgat caaaaagtaa tcggggtgaa ccgtcagcac gtccgggttc   8700
ttgccttctg tgatctcgcg gtacatccaa tcaactagct cgatctcgat gtactccggc   8760
cgcccggttt cgctctttac gatcttgtag cggctaatca aggcttcacc ctcggatacc   8820
gtcaccaggc ggccgttctt ggccttcttc gtacgctgca tggcaacgtg cgtggtgttt   8880
aaccgaatgc aggtttctac caggtcgtct ttctgctttc cgccatcggc tcgccggcag   8940
aacttgagta cgtccgcaac gtgtggacgg aacacgcggc cgggcttgtc tcccttccct   9000
tcccggtatc ggttcatgga ttcggttaga tgggaaaccg ccatcagtac caggtcgtaa   9060
tcccacacac tggccatgcc ggccggccct gcggaaacct ctacgtgccc gtctggaagc   9120
tcgtagcgga tcacctcgcc agctcgtcgg tcacgcttcg acagacggaa aacggccacg   9180
tccatgatgc tgcgactatc gcgggtgccc acgtcataga gcatcggaac gaaaaaatct   9240
```

```
ggttgctcgt cgcccttggg cggcttccta atcgacggcg caccggctgc cggcggttgc   9300

cgggattctt tgcggattcg atcagcggcc gcttgccacg attcaccggg gcgtgcttct   9360

gcctcgatgc gttgccgctg ggcggcctgc gcggccttca acttctccac caggtcatca   9420

cccagcgccg cgccgatttg taccgggccg gatggtttgc gaccgctcac gccgattcct   9480

cgggcttggg ggttccagtg ccattgcagg gccggcagac aacccagccg cttacgcctg   9540

gccaaccgcc cgttcctcca cacatggggc attccacggc gtcggtgcct ggttgttctt   9600

gattttccat gccgcctcct ttagccgcta aaattcatct actcatttat tcatttgctc   9660

atttactctg gtagctgcgc gatgtattca gatagcagct cggtaatggt cttgccttgg   9720

cgtaccgcgt acatcttcag cttggtgtga tcctccgccg gcaactgaaa gttgacccgc   9780

ttcatggctg gcgtgtctgc caggctggcc aacgttgcag ccttgctgct gcgtgcgctc   9840

ggacggccgg cacttagcgt gtttgtgctt ttgctcattt tctctttacc tcattaactc   9900

aaatgagttt tgatttaatt tcagcggcca gcgcctggac ctcgcgggca gcgtcgccct   9960

cgggttctga ttcaagaacg gttgtgccgg cggcggcagt gcctgggtag ctcacgcgct  10020

gcgtgatacg ggactcaaga atgggcagct cgtacccggc cagcgcctcg gcaacctcac  10080

cgccgatgcg cgtgcctttg atcgcccgcg acacgacaaa ggccgcttgt agccttccat  10140

ccgtgacctc aatgcgctgc ttaaccagct ccaccaggtc ggcggtggcc catatgtcgt  10200

aagggcttgg ctgcaccgga atcagcacga agtcggctgc cttgatcgcg gacacagcca  10260

agtccgccgc ctggggcgct ccgtcgatca ctacgaagtc gcgccggccg atggccttca  10320

cgtcgcggtc aatcgtcggg cggtcgatgc cgacaacggt tagcggttga tcttcccgca  10380

cggccgccca atcgcgggca ctgccctggg gatcggaatc gactaacaga acatcggccc  10440

cggcgagttg cagggcgcgg gctagatggg ttgcgatggt cgtcttgcct gacccgcctt  10500

tctggttaag tacagcgata accttcatgc gttccccttg cgtatttgtt tatttactca  10560

tcgcatcata tacgcagcga ccgcatgacg caagctgttt tactcaaata cacatcacct  10620

ttttagacgg cggcgctcgg tttcttcagc ggccaagctg gccggccagg ccgccagctt  10680

ggcatcagac aaaccggcca ggatttcatg cagccgcacg gttccggatg agcattca    10738
```

<210> SEQ ID NO 19
<211> LENGTH: 9608
<212> TYPE: DNA
<213> ORGANISM: Artificial Sequence
<220> FEATURE:
<223> OTHER INFORMATION: Plasmid pACYC_rbwA_Srub

<400> SEQUENCE: 19

```
tcaggcgggc aagaatgtga ataaaggccg gataaaactt gtgcttattt ttctttacgg     60

tctttaaaaa ggccgtaata tccagctgaa cggtctggtt ataggtacat tgagcaactg    120

actgaaatgc ctcaaaatgt tctttacgat gccattggga tatatcaacg gtggtatatc    180

cagtgatttt tttctccatt ttagcttcct tagctcctga aaatctcgat aactcaaaaa    240

atacgcccgg tagtgatctt atttcattat ggtgaaagtt ggaacctctt acgtgccgat    300

caacgtctca ttttcgccaa aagttggccc agggcttccc ggtatcaaca gggacaccag    360

gatttattta ttctgcgaag tgatcttccg tcacaggtat ttattcggcg caaagtgcgt    420

cgggtgatgc tgccaactta ctgatttagt gtatgatggt gtttttgagg tgctccagtg    480

gcttctgttt ctatcagctg tccctcctgt tcagctactg acggggtggt gcgtaacggc    540
```

-continued

```
aaaagcaccg ccggacatca gcgctagcgg agtgtatact ggcttactat gttggcactg    600

atgagggtgt cagtgaagtg cttcatgtgg caggagaaaa aaggctgcac cggtgcgtca    660

gcagaatatg tgatacagga tatattccgc ttcctcgctc actgactcgc tacgctcggt    720

cgttcgactg cggcgagcgg aaatggctta cgaacggggc ggagatttcc tggaagatgc    780

caggaagata cttaacaggg aagtgagagg gccgcggcaa agccgttttt ccataggctc    840

cgcccccctg acaagcatca cgaaatctga cgctcaaatc agtggtggcg aaacccgaca    900

ggactataaa gataccaggc gtttcccccct ggcggctccc tcgtgcgctc tcctgttcct    960

gcctttcggt ttaccggtgt cattccgctg ttatggccgc gtttgtctca ttccacgcct   1020

gacactcagt tccgggtagg cagttcgctc caagctggac tgtatgcacg aacccccgt   1080

tcagtccgac cgctgcgcct tatccggtaa ctatcgtctt gagtccaacc cggaaagaca   1140

tgcaaaagca ccactggcag cagccactgg taattgattt agaggagtta gtcttgaagt   1200

catgcgccgg ttaaggctaa actgaaagga caagttttgg tgactgcgct cctccaagcc   1260

agttacctcg gttcaaagag ttggtagctc agagaacctt cgaaaaaccg ccctgcaagg   1320

cggttttttc gttttcagag caagagatta cgcgcagacc aaaacgatct caagaagatc   1380

atcttattaa tcagataaaa tatttctaga tttcagtgca atttatctct tcaaatgtag   1440

cacctgaagt cagccccata cgatataagt tgtaattctc atgtttgaca gcttatcatc   1500

gataagcttt aatgcggtag tttatcacag ttaaattgct aacgcagtca ggcaccgtgt   1560

atgattgaac aagatggatt gcacgcaggt tctccggccg cttgggtgga gaggctattc   1620

ggctatgact gggcacaaca gacaatcggc tgctctgatg ccgccgtgtt ccggctgtca   1680

gcgcaggggc gcccggttct ttttgtcaag accgacctgt ccggtgccct gaatgaactg   1740

caggacgagg cagcgcggct atcgtggctg gccacgacgg gcgttccttg cgcagctgtg   1800

ctcgacgttg tcactgaagc gggaagggac tggctgctat tgggcgaagt gccggggcag   1860

gatctcctgt catctcacct tgctcctgcc gagaaagtat ccatcatggc tgatgcaatg   1920

cggcggctgc atacgcttga tccggctacc tgcccattcg accaccaagc gaaacatcgc   1980

atcgagcgag cacgtactcg gatggaagcc ggtcttgtcg atcaggatga tctggacgaa   2040

gagcatcagg ggctcgcgcc agccgaactg ttcgccaggc tcaaggcgcg catgcccgac   2100

ggcgaggatc tcgtcgtgac ccatggcgat gcctgcttgc cgaatatcat ggtggaaaat   2160

ggccgctttt ctggattcat cgactgtggc cggctgggtg tggcggaccg ctatcaggac   2220

atagcgttgg ctacccgtga tattgctgaa gagcttggcg gcgaatgggc tgaccgcttc   2280

ctcgtgcttt acggtatcgc cgctcccgat tcgcagcgca tcgccttcta tcgccttctt   2340

gacgagttca tggaagccgg cggcacctcg ctaacggatt caccactcca agaattggag   2400

ccaatcaatt cttgcggaga actgtgaatg cgcaaaccaa cccttggcag aacatatcca   2460

tcgcgtccgc catctccagc agccgcacgc ggcgcatctc gggcagcgtt gggtcctggc   2520

cacgggtgcg catgatcgtg ctcctgtcgt tgaggacccg gctaggctgg cggggttgcc   2580

ttactggtta gcagaatgaa tcaccgatac gcgagcgaac gtgaagcgac tgctgctgca   2640

aaacgtctgc gacctgagca acaacatgaa tggtcttcgg tttccgtgtt tcgtaaagtc   2700

tggaaacgcg gaagtcccct acgtgctgct gaagttgccc gcaacagaga gtggaaccaa   2760

ccggtgatac cacgatacta tgactgagag tcaacgccat gagcggcctc atttcttatt   2820

ctgagttaca acagtccgca ccgctgtccg gtagctcctt ccggtgggcg cggggcatga   2880

ctatcgtcgc cgcacttatg actgtcttct ttatcatgca actcgtagga caggtgccgg   2940
```

```
cagcgcccaa cagtccccg gccacggggc ctgccaccat acccacgccg aaacaagcgc   3000
cctgcaccat tatgttccgg atctgcatcg caggatgctg ctggctaccc tgtggaacac   3060
ctacatctgt attaacgaag cgctaaccgt ttttatcagg ctctgggagg cagaataaat   3120
gatcatatcg tcaattatta cctccacggg gagagcctga gcaaactggc ctcaggcatt   3180
tgagaagcac acggtcacac tgcttccggt agtcaataaa ccggtaaacc agcaatagac   3240
ataagcggct atttaacgac cctgccctga accgacgacc gggtcgaatt tgctttcgaa   3300
tttctgccat tcatccgctt attatcactt attcaggcgt agcaccaggc gtttaagggc   3360
accaataact gccttaaaaa aattacgccc cgccctgcca ctcatcgcag tactgttgta   3420
attcattaag cattctgccg acatggaagc catcacaaac ggcatgatga acctgaatcg   3480
ccagcggcat cagcaccttg tcgccttgcg tataatattt gcccatggat ttaaatttaa   3540
tctttctgcg aattgagatg acgccactgg ctgggcgtca tcccggtttc ccgggtaaac   3600
accaccgaaa aatagttact atcttcaaag ccacattcgg tcgaaatatc actgattaac   3660
aggcggctat gctggagaag atattgcgca tgacacactc tgacctgtcg cagatattga   3720
ttgatggtca ttccagtctg ctggcgaaat tgctgacgca aaacgcgctc actgcacgat   3780
gcctcatcac aaaatttatc cagcgcaaag ggacttttca ggctagccgc cagccgggta   3840
atcagcttat ccagcaacgt ttcgctggat gttggcggca acgaatcact ggtgtaacga   3900
tggcgattca gcaacatcac caactgcccg aacagcaact cagccatttc gttagcaaac   3960
ggcacatgct gactactttc atgctcaagc tgaccgataa cctgccgcgc ctgcgccatc   4020
cccatgctac ctaagcgcca gtgtggttgc cctgcgctgg cgttaaatcc cggaatcgcc   4080
ccctgccagt caagattcag cttcagacgc tccgggcaat aaataatatt ctgcaaaacc   4140
agatcgttaa cggaagcgta ggagtgttta tcgtcagcat gaatgtaaaa gagatcgcca   4200
cgggtaatgc gataagggcg atcgttgagt acatgcaggc cattaccgcg ccagacaatc   4260
accagctcac aaaaatcatg tgtatgttca gcaaagacat cttgcggata acggtcagcc   4320
acagcgactg cctgctggtc gctggcaaaa aaatcatctt tgagaagttt taactgatgc   4380
gccaccgtgg ctacctcggc cagagaacga agttgattat tcgcaatatg gcgtacaaat   4440
acgttgagaa gattcgcgtt attgcagaaa gccatcccgt ccctggcgaa tatcacgcgg   4500
tgaccagtta aactctcggc gaaaaagcgt cgaaaagtgg ttactgtcgc tgaatccaca   4560
gcgataggcg atgtcagtaa cgctggcctc gctgtggcgt agcagatgtc gggctttcat   4620
cagtcgcagg cggttcaggt atcgctgagg cgtcagtccc gtttgctgct taagctgccg   4680
atgtagcgta cgcagtgaaa gagaaaattg atccgccacg gcatcccaat tcacctcatc   4740
ggcaaaatgg tcctccagcc aggccagaag caagttgaga cgtgatgcgc tgttttccag   4800
gttctcctgc aaactgcttt tacgcagcaa gagcagtaat tgcataaaca agatctcgcg   4860
actggcggtc gagggtaaat cattttcccc ttcctgctgt tccatctgtg caaccagctg   4920
tcgcacctgc tgcaatacgc tgtggttaac gcgccagtga gacggatact gcccatccag   4980
ctcttgtggc agcaactgat tcagcccggc gagaaactga aatcgatccg gcgagcgata   5040
cagcacattg gtcagacaca gattatcggt atgttcatac agatgccgat catgatcgcg   5100
tacgaaacag accgtgccac cggtgatggt atagggctgc ccattaaaca catgaatacc   5160
cgtgccatgt tcgacaatca caatttcatg aaaatcatga tgatgttcag gaaaatccgc   5220
ctgcgggagc cggggttcta tcgccacgga cgcgttacca gacggaaaaa aatccacact   5280
```

atgtaatacg gtcatactgg cctcctgatg tcgtcaacac ggcgaaatag taatcacgag 5340
gtcaggttct taccttaaat tttcgacgga aaaccacgta aaaaacgtcg atttttcaag 5400
atacagcgtg aattttcagg aaatgcggtg agcatcacat caccacaatt cagcaaattg 5460
tgaacatcat cacgttcatc tttccctggt tgccaatggc ccattttcct gtcagtaacg 5520
agaaggtcgc gaattcaggc gctttttaga ctggtcgtaa tgaacattta aatgaattcc 5580
cttgggactc tagagatccg cgggggcccg gcatcatttt attgttattc atgggggtgg 5640
gaaatgaaac cagaaacaga aattgttcgc gtcggtgact ggcaggtcta tgtagagcga 5700
tatatttatc caggcgtcac ggattccgtc atttgcgtta atggatcttt ttcaaccacg 5760
ctggcttttc gcagctgcgt acgtaacttc aagaaccggg ttaacgtcat tctcttcgat 5820
ctgccgttcc tcggtcagtc ccgtgagcat aatgatttaa ccaaaccgct gtcgaaaacc 5880
gatgaggttt tcattctgca gagtttgatt aaccattatg aaccgtctta tctgctctcc 5940
atctcctggg gcggactggc agcattgatg gcgctctcct cccgccctcg ctccatccgc 6000
aaagccgtgg tggcctcgtt ctccaccaag gtgaacgacg cgatgaatta ctacgtcagt 6060
cagggcaaga aattactgga tgaaggcaaa ggcgatgaag cggcgatgct gctcaatacc 6120
gaggttggca aatatctgcc gaatctgttg aagcaggtga actacgaaca cttgagacag 6180
tttgacgaat cagcgcaaaa acaggtgcgt taccacgtcg cgcaaattac cgaatttaat 6240
caggcggact atatcgatac cttccggcaa atcgatacgc cgatactgtt catcaacggc 6300
gagcaggacg aatacactac agcgcaagat attaaggaac tcagtaacta tatcaataac 6360
tgcgaattta ttaccgtacc gcaggctggc cactttattt atatggaaag ccgctttgcg 6420
gccgattatt tcaacgacgt gatgaacggt tttctgtttg ttgaagaagc gatggcctcc 6480
tgaggataac aaactaaaat attgattcga caagacagga tggtgatatg agagtgataa 6540
tatgcgccct ggggtcctct ggcgatgttt acccatcgag cacgcgagag tagggaactg 6600
ccaggcatca aataaaacga aaggctcagt cgaaagactg ggcctttcgt tttatctgtt 6660
gtttgtcggt gaacgctctc ctgagtagga caaatccgcc gggagcggat ttgaacgatg 6720
ataagctgtc aaacatgaga attcttgaag acgaaagggc ctcgtgtgta caaacgttcg 6780
tcaaaagggc gacacaaaat tcctgcaggg gccggcccag cgccggcggt cgagtggcga 6840
cggcgcggct tgtccgcgcc ctggtagatt gcctggccgt aggccagcca tttttgagcg 6900
gccagcggcc gcgataggcc gacgcgaagc ggcggggcgt agggagcgca gcgaccgaag 6960
ggtaggcgct ttttgcagct cttcggctgt gcgctggcca gacagttatg cacaggccag 7020
gcgggtttta agagttttaa taagttttaa agagttttag gcggaaaaat cgcctttttt 7080
ctcttttata tcagtcactt acatgtgtga ccggttccca atgtacggct ttgggttccc 7140
aatgtacggg ttccggttcc caatgtacgg ctttgggttc ccaatgtacg tgctatccac 7200
aggaaagaga ccttttcgac ctttttcccc tgctagggca atttgcccta gcatctgctc 7260
cgtacattag gaaccggcgg atgcttcgcc ctcgatcagg ttgcggtagc gcatgactag 7320
gatcgggcca gcctgccccg cctcctcctt caaatcgtac tccggcaggt catttgaccc 7380
gatcagcttg cgcacggtga aacagaactt cttgaactct ccggcgctgc cactgcgttc 7440
gtagatcgtc ttgaacaacc atctggcttc tgccttgcct gcggcgcggc gtgccaggcg 7500
gtagagaaaa cggccgatgc cgggatcgat caaaaagtaa tcggggtgaa ccgtcagcac 7560
gtccgggttc ttgccttctg tgatctcgcg gtacatccaa tcaactagct cgatctcgat 7620
gtactccggc cgcccggttt cgctctttac gatcttgtag cggctaatca aggcttcacc 7680

```
ctcggatacc gtcaccaggc ggccgttctt ggccttcttc gtacgctgca tggcaacgtg   7740

cgtggtgttt aaccgaatgc aggtttctac caggtcgtct ttctgctttc cgccatcggc   7800

tcgccggcag aacttgagta cgtccgcaac gtgtggacgg aacacgcggc cgggcttgtc   7860

tcccttccct tcccggtatc ggttcatgga ttcggttaga tgggaaaccg ccatcagtac   7920

caggtcgtaa tcccacacac tggccatgcc ggccggccct gcggaaacct ctacgtgccc   7980

gtctggaagc tcgtagcgga tcacctcgcc agctcgtcgg tcacgcttcg acagacggaa   8040

aacggccacg tccatgatgc tgcgactatc gcgggtgccc acgtcataga gcatcggaac   8100

gaaaaaatct ggttgctcgt cgcccttggg cggcttccta atcgacggcg caccggctgc   8160

cggcggttgc cgggattctt tgcggattcg atcagcggcc gcttgccacg attcaccggg   8220

gcgtgcttct gcctcgatgc gttgccgctg ggcggcctgc gcggccttca acttctccac   8280

caggtcatca cccagcgccg cgccgatttg taccgggccg gatggtttgc gaccgctcac   8340

gccgattcct cgggcttggg ggttccagtg ccattgcagg gccggcagac aacccagccg   8400

cttacgcctg gccaaccgcc cgttcctcca cacatggggc attccacggc gtcggtgcct   8460

ggttgttctt gattttccat gccgcctcct ttagccgcta aaattcatct actcatttat   8520

tcatttgctc atttactctg gtagctgcgc gatgtattca gatagcagct cggtaatggt   8580

cttgccttgg cgtaccgcgt acatcttcag cttggtgtga tcctccgccg gcaactgaaa   8640

gttgacccgc ttcatggctg gcgtgtctgc caggctggcc aacgttgcag ccttgctgct   8700

gcgtgcgctc ggacggccgg cacttagcgt gtttgtgctt ttgctcattt tctctttacc   8760

tcattaactc aaatgagttt tgatttaatt tcagcggcca gcgcctggac ctcgcgggca   8820

gcgtcgccct cgggttctga ttcaagaacg gttgtgccgg cggcggcagt gcctgggtag   8880

ctcacgcgct gcgtgatacg ggactcaaga atgggcagct cgtacccggc cagcgcctcg   8940

gcaacctcac cgccgatgcg cgtgcctttg atcgcccgcg acacgacaaa ggccgcttgt   9000

agccttccat ccgtgacctc aatgcgctgc ttaaccagct ccaccaggtc ggcggtggcc   9060

catatgtcgt aagggcttgg ctgcaccgga atcagcacga agtcggctgc cttgatcgcg   9120

gacacagcca agtccgccgc ctggggcgct ccgtcgatca ctacgaagtc gcgccggccg   9180

atggccttca cgtcgcggtc aatcgtcggg cggtcgatgc cgacaacggt tagcggttga   9240

tcttcccgca cggccgccca atcgcgggca ctgccctggg gatcggaatc gactaacaga   9300

acatcggccc cggcgagttg cagggcgcgg gctagatggg ttgcgatggt cgtcttgcct   9360

gacccgcctt tctggttaag tacagcgata accttcatgc gttccccttg cgtatttgtt   9420

tatttactca tcgcatcata tacgcagcga ccgcatgacg caagctgttt tactcaaata   9480

cacatcacct ttttagacgg cggcgctcgg tttcttcagc ggccaagctg gccggccagg   9540

ccgccagctt ggcatcagac aaaccggcca ggatttcatg cagccgcacg gttccggatg   9600

agcattca                                                            9608
```

<210> SEQ ID NO 20
<211> LENGTH: 2132
<212> TYPE: DNA
<213> ORGANISM: Artificial Sequence
<220> FEATURE:
<223> OTHER INFORMATION: Synthetical operon rhlA_Pa rbwB_Srub

<400> SEQUENCE: 20

```
tttgggaggt gtgaaatgcg gcgcgaaagt ctgttggtat cggtttgcaa gggcctgcgg     60
```

```
gtacatgtcg agcgcgttgg gcaggatccc gggcgcagca cggtgatgct ggtcaacggc    120

gcgatggcga ccaccgcctc gttcgcccgg acctgcaagt gcctggccga acatttcaac    180

gtggtgctgt tcgacctgcc cttcgccggg cagtcgcgtc agcacaaccc gcagcggggg    240

ttgatcacca aggacgacga ggtggaaatc ctcctggcgc tgatcgagcg cttcgaggtc    300

aatcacctgg tctccgcgtc ctggggcggt atctccacgc tgctggcgct gtcgcgcaat    360

ccgcgcggca tccgcagctc ggtggtgatg gcattcgccc ctggactgaa ccaggcgatg    420

ctcgactacg tcgggcgggc gcaggcgctg atcgagctgg acgacaagtc ggcgatcggc    480

catctgctca acgagaccgt cggcaaatac ctgccgccgc gcctgaaagc cagcaaccat    540

cagcacatgg cttcgctggc caccggcgaa tacgagcagg cgcgctttca catcgaccag    600

gtgctggcgc tcaacgatcg ggctacctg gcttgcctgg agcggatcca gagccacgtg    660

catttcatca acggcagctg ggacgaatac accaccgccg aggacgcccg ccagttccgc    720

gactacctgc cgcactgcag tttctcgcgg gtggagggca ccgggcattt cctcgacctg    780

gagtccaagc tggccgcggt acgcgtgcac cgcgccctgc tcgagcacct gctgaagcaa    840

ccggagccgc agcgggcgga acgcgcggcg ggattccacg agatggccat cggctacgcc    900

tgaggataac aaactaaaat attgattcga caagacagga tggtgatatg agagtgataa    960

tatgcgccct ggggtcctct ggcgatgttt acccatgcat cgaaattggc gcgatattaa   1020

aagaaagaaa ccatgatgtg catatactta ccaatgaata cttcaaagat tacgttgagt   1080

ctcgcaatct ttcctttca gcagtaggca gtaaagagga ctttatccgt tcagtacgtg   1140

acagccagct atgggagaag aaaacctcat taataaaaat atctgcatac atggctaatt   1200

atcaggttgg tatgtttcat tcaatcgaga ggttggtaaa tgataattgt gtaattattc   1260

attctctttg ggtattctca gccaaggtgg ttagcgaaaa atattcgtta aaacgattcc   1320

cgataagcct taccaacgcc aaccttaaac tctgcccggg gaaatttatt agctggttgg   1380

aaagaaagct cggcacctca ttgaacctga aggctgaact ctttagacgc cgcctggttt   1440

ctccgctgtt acaggaggtc atcgcctcga taagaaaatc agagaacctc ccagccgata   1500

aaaacatcta taccgacctg gtagataggc gcttgaatcc tattattttg tatgagcctt   1560

ggttctacga aaaaaaaccg cagcacggat tttatatggg gttcctgtta aataaaaacc   1620

ggacattaga ccacgctccg ataatcaacc gctttgtgga caaaaaaacg gtggttttct   1680

tcaccagttg ggcattgtct gatgaagcag gcataaatca tgtcttaagc agtctgaaag   1740

atgaaggttt gaaatgtgta ctggtcaccc ccaccctcga cagcatccac gttgaagaaa   1800

atgtcatcag aacaccttac cttaatatgg atagcatcaa aggatgtctg tttgccattc   1860

accacggcgg catcggcacc agtgcccaac tgcttaaaaa cggcatacct cagttaatct   1920

acccaaaagc ctttgatcag ttcgaaaacg caagctctct cgaaagaata ggctgtggcg   1980

ttaaaggcgg cgatataaat gcgttgaggc atatgattaa aaagtcggtt accaatgata   2040

ataactgtgc tttttacgcc tcgcggctaa gtgaagagaa caaagaacga aacgatgcgc   2100

tggaacgttt actcatgggt taagctcgag ca                                 2132
```

<210> SEQ ID NO 21
<211> LENGTH: 10787
<212> TYPE: DNA
<213> ORGANISM: Artificial Sequence
<220> FEATURE:
<223> OTHER INFORMATION: Plasmid pACYC_rhlA_Pa rbwB_Srub

<400> SEQUENCE: 21

```
tcaggcgggc aagaatgtga ataaaggccg gataaaactt gtgcttattt ttctttacgg     60
tctttaaaaa ggccgtaata tccagctgaa cggtctggtt ataggtacat tgagcaactg    120
actgaaatgc ctcaaaatgt tctttacgat gccattggga tatatcaacg gtggtatatc    180
cagtgatttt tttctccatt ttagcttcct tagctcctga aaatctcgat aactcaaaaa    240
atacgcccgg tagtgatctt atttcattat ggtgaaagtt ggaacctctt acgtgccgat    300
caacgtctca ttttcgccaa aagttggccc agggcttccc ggtatcaaca gggacaccag    360
gatttattta ttctgcgaag tgatcttccg tcacaggtat ttattcggcg caaagtgcgt    420
cgggtgatgc tgccaactta ctgatttagt gtatgatggt gtttttgagg tgctccagtg    480
gcttctgttt ctatcagctg tccctcctgt tcagctactg acggggtggt gcgtaacggc    540
aaaagcaccg ccggacatca gcgctagcgg agtgtatact ggcttactat gttggcactg    600
atgagggtgt cagtgaagtg cttcatgtgg caggagaaaa aaggctgcac cggtgcgtca    660
gcagaatatg tgatacagga tatattccgc ttcctcgctc actgactcgc tacgctcggt    720
cgttcgactg cggcgagcgg aaatggctta cgaacggggc ggagatttcc tggaagatgc    780
caggaagata cttaacaggg aagtgagagg gccgcggcaa agccgttttt ccataggctc    840
cgcccccctg acaagcatca cgaaatctga cgctcaaatc agtggtggcg aaacccgaca    900
ggactataaa gataccaggc gtttccccct ggcggctccc tcgtgcgctc tcctgttcct    960
gcctttcggt ttaccggtgt cattccgctg ttatggccgc gtttgtctca ttccacgcct   1020
gacactcagt tccgggtagg cagttcgctc caagctggac tgtatgcacg aaccccccgt   1080
tcagtccgac cgctgcgcct tatccggtaa ctatcgtctt gagtccaacc cggaaagaca   1140
tgcaaaagca ccactggcag cagccactgg taattgattt agaggagtta gtcttgaagt   1200
catgcgccgg ttaaggctaa actgaaagga caagttttgg tgactgcgct cctccaagcc   1260
agttacctcg gttcaaagag ttggtagctc agagaacctt cgaaaaaccg ccctgcaagg   1320
cggttttttc gttttcagag caagagatta cgcgcagacc aaaacgatct caagaagatc   1380
atcttattaa tcagataaaa tatttctaga tttcagtgca atttatctct tcaaatgtag   1440
cacctgaagt cagccccata cgatataagt tgtaattctc atgtttgaca gcttatcatc   1500
gataagcttt aatgcggtag tttatcacag ttaaattgct aacgcagtca ggcaccgtgt   1560
atgattgaac aagatggatt gcacgcaggt tctccggccg cttgggtgga gaggctattc   1620
ggctatgact gggcacaaca gacaatcggc tgctctgatg ccgccgtgtt ccggctgtca   1680
gcgcaggggc gcccggttct ttttgtcaag accgacctgt ccggtgccct gaatgaactg   1740
caggacgagg cagcgcggct atcgtggctg gccacgacgg gcgttccttg cgcagctgtg   1800
ctcgacgttg tcactgaagc gggaagggac tggctgctat tgggcgaagt gccggggcag   1860
gatctcctgt catctcacct tgctcctgcc gagaaagtat ccatcatggc tgatgcaatg   1920
cggcggctgc atacgcttga tccggctacc tgcccattcg accaccaagc gaaacatcgc   1980
atcgagcgag cacgtactcg gatggaagcc ggtcttgtcg atcaggatga tctggacgaa   2040
gagcatcagg ggctcgcgcc agccgaactg ttcgccaggc tcaaggcgcg catgcccgac   2100
ggcgaggatc tcgtcgtgac ccatggcgat gcctgcttgc cgaatatcat ggtggaaaat   2160
ggccgctttt ctggattcat cgactgtggc cggctgggtg tggcggaccg ctatcaggac   2220
atagcgttgg ctacccgtga tattgctgaa gagcttggcg gcgaatgggc tgaccgcttc   2280
ctcgtgcttt acggtatcgc cgctcccgat tcgcagcgca tcgccttcta tcgccttctt   2340
```

-continued

```
gacgagttca tggaagccgg cggcacctcg ctaacggatt caccactcca agaattggag   2400
ccaatcaatt cttgcggaga actgtgaatg cgcaaaccaa cccttggcag aacatatcca   2460
tcgcgtccgc catctccagc agccgcacgc ggcgcatctc gggcagcgtt gggtcctggc   2520
cacgggtgcg catgatcgtg ctcctgtcgt tgaggacccg gctaggctgg cggggttgcc   2580
ttactggtta gcagaatgaa tcaccgatac gcgagcgaac gtgaagcgac tgctgctgca   2640
aaacgtctgc gacctgagca acaacatgaa tggtcttcgg tttccgtgtt tcgtaaagtc   2700
tggaaacgcg gaagtcccct acgtgctgct gaagttgccc gcaacagaga gtggaaccaa   2760
ccggtgatac cacgatacta tgactgagag tcaacgccat gagcggcctc atttcttatt   2820
ctgagttaca acagtccgca ccgctgtccg gtagctcctt ccggtgggcg cggggcatga   2880
ctatcgtcgc cgcacttatg actgtcttct ttatcatgca actcgtagga caggtgccgg   2940
cagcgcccaa cagtcccccg gccacggggc ctgccaccat acccacgccg aaacaagcgc   3000
cctgcaccat tatgttccgg atctgcatcg caggatgctg ctggctaccc tgtggaacac   3060
ctacatctgt attaacgaag cgctaaccgt ttttatcagg ctctgggagg cagaataaat   3120
gatcatatcg tcaattatta cctccacggg gagagcctga gcaaactggc ctcaggcatt   3180
tgagaagcac acggtcacac tgcttccggt agtcaataaa ccggtaaacc agcaatagac   3240
ataagcggct atttaacgac cctgccctga accgacgacc gggtcgaatt tgctttcgaa   3300
tttctgccat tcatccgctt attatcactt attcaggcgt agcaccaggc gtttaagggc   3360
accaataact gccttaaaaa aattacgccc cgccctgcca ctcatcgcag tactgttgta   3420
attcattaag cattctgccg acatggaagc catcacaaac ggcatgatga acctgaatcg   3480
ccagcggcat cagcaccttg tcgccttgcg tataatattt gcccatggat ttaaatttaa   3540
tctttctgcg aattgagatg acgccactgg ctgggcgtca tcccggtttc ccgggtaaac   3600
accaccgaaa aatagttact atcttcaaag ccacattcgg tcgaaatatc actgattaac   3660
aggcggctat gctggagaag atattgcgca tgacacactc tgacctgtcg cagatattga   3720
ttgatggtca ttccagtctg ctggcgaaat tgctgacgca aaacgcgctc actgcacgat   3780
gcctcatcac aaaatttatc cagcgcaaag ggacttttca ggctagccgc cagccgggta   3840
atcagcttat ccagcaacgt ttcgctggat gttggcggca acgaatcact ggtgtaacga   3900
tggcgattca gcaacatcac caactgcccg aacagcaact cagccatttc gttagcaaac   3960
ggcacatgct gactactttc atgctcaagc tgaccgataa cctgccgcgc ctgcgccatc   4020
cccatgctac ctaagcgcca gtgtggttgc cctgcgctgg cgttaaatcc cggaatcgcc   4080
ccctgccagt caagattcag cttcagacgc tccgggcaat aaataatatt ctgcaaaacc   4140
agatcgttaa cggaagcgta ggagtgttta tcgtcagcat gaatgtaaaa gagatcgcca   4200
cgggtaatgc gataagggcg atcgttgagt acatgcaggc cattaccgcg ccagacaatc   4260
accagctcac aaaaatcatg tgtatgttca gcaaagacat cttgcggata acggtcagcc   4320
acagcgactg cctgctggtc gctggcaaaa aaatcatctt tgagaagttt taactgatgc   4380
gccaccgtgg ctacctcggc cagagaacga agttgattat tcgcaatatg gcgtacaaat   4440
acgttgagaa gattcgcgtt attgcagaaa gccatcccgt ccctggcgaa tatcacgcgg   4500
tgaccagtta aactctcggc gaaaaagcgt cgaaaagtgg ttactgtcgc tgaatccaca   4560
gcgataggcg atgtcagtaa cgctggcctc gctgtggcgt agcagatgtc gggctttcat   4620
cagtcgcagg cggttcaggt atcgctgagg cgtcagtccc gtttgctgct taagctgccg   4680
atgtagcgta cgcagtgaaa gagaaaattg atccgccacg gcatcccaat tcacctcatc   4740
```

```
ggcaaaatgg tcctccagcc aggccagaag caagttgaga cgtgatgcgc tgttttccag   4800
gttctcctgc aaactgcttt tacgcagcaa gagcagtaat tgcataaaca agatctcgcg   4860
actggcggtc gagggtaaat cattttcccc ttcctgctgt tccatctgtg caaccagctg   4920
tcgcacctgc tgcaatacgc tgtggttaac gcgccagtga gacggatact gcccatccag   4980
ctcttgtggc agcaactgat tcagcccggc gagaaactga aatcgatccg gcgagcgata   5040
cagcacattg gtcagacaca gattatcggt atgttcatac agatgccgat catgatcgcg   5100
tacgaaacag accgtgccac cggtgatggt atagggctgc ccattaaaca catgaatacc   5160
cgtgccatgt tcgacaatca caatttcatg aaaatcatga tgatgttcag gaaaatccgc   5220
ctgcgggagc cggggttcta tcgccacgga cgcgttacca gacggaaaaa aatccacact   5280
atgtaatacg gtcatactgg cctcctgatg tcgtcaacac ggcgaaatag taatcacgag   5340
gtcaggttct accttaaat tttcgacgga aaaccacgta aaaaacgtcg atttttcaag   5400
atacagcgtg aattttcagg aaatgcggtg agcatcacat caccacaatt cagcaaattg   5460
tgaacatcat cacgttcatc tttccctggt tgccaatggc ccattttcct gtcagtaacg   5520
agaaggtcgc gaattcaggc gctttttaga ctggtcgtaa tgaacattta aatgaattcc   5580
cttgggactc tagagatccg cgggggccca ggagggggga tctggcattt ttgggaggtg   5640
tgaaatgcgg cgcgaaagtc tgttggtatc ggtttgcaag ggcctgcggg tacatgtcga   5700
gcgcgttggg caggatcccg ggcgcagcac ggtgatgctg gtcaacggcg cgatggcgac   5760
caccgcctcg ttcgcccgga cctgcaagtg cctggccgaa catttcaacg tggtgctgtt   5820
cgacctgccc ttcgccgggc agtcgcgtca gcacaacccg cagcgggggt tgatcaccaa   5880
ggacgacgag gtggaaatcc tcctggcgct gatcgagcgc ttcgaggtca atcacctggt   5940
ctccgcgtcc tggggcggta tctccacgct gctggcgctg tcgcgcaatc cgcgcggcat   6000
ccgcagctcg gtggtgatgg cattcgcccc tggactgaac caggcgatgc tcgactacgt   6060
cgggcgggcg caggcgctga tcgagctgga cgacaagtcg gcgatcggcc atctgctcaa   6120
cgagaccgtc ggcaaatacc tgccgccgcg cctgaaagcc agcaaccatc agcacatggc   6180
ttcgctggcc accggcgaat acgagcaggc gcgctttcac atcgaccagg tgctggcgct   6240
caacgatcgg ggctacctgg cttgcctgga gcggatccag agccacgtgc atttcatcaa   6300
cggcagctgg gacgaataca ccaccgccga ggacgcccgc cagttccgcg actacctgcc   6360
gcactgcagt ttctcgcggg tggagggcac cgggcatttc ctcgacctgg agtccaagct   6420
ggccgcggta cgcgtgcacc gcgccctgct cgagcacctg ctgaagcaac cggagccgca   6480
gcgggcggaa cgcgcggcgg gattccacga gatggccatc ggctacgcct gaggataaca   6540
aactaaaata ttgattcgac aagacaggat ggtgatatga gagtgataat atgcgccctg   6600
gggtcctctg gcgatgttta cccatgcatc gaaattggcg cgatattaaa agaaagaaac   6660
catgatgtgc atatacttac caatgaatac ttcaaagatt acgttgagtc tcgcaatctt   6720
tccttttcag cagtaggcag taaagaggac tttatccgtt cagtacgtga cagccagcta   6780
tgggagaaga aaacctcatt aataaaaata tctgcataca tggctaatta tcaggttggt   6840
atgtttcatt caatcgagag gttggtaaat gataattgtg taattattca ttctctttgg   6900
gtattctcag ccaaggtggt tagcgaaaaa tattcgttaa aacgattccc gataagcctt   6960
accaacgcca accttaaact ctgcccgggg aaatttatta gctggttgga aagaaagctc   7020
ggcacctcat tgaacctgaa ggctgaactc tttagacgcc gcctggtttc tccgctgtta   7080
```

-continued

```
caggaggtca tcgcctcgat aagaaaatca gagaacctcc cagccgataa aaacatctat   7140
accgacctgg tagataggcg cttgaatcct attattttgt atgagccttg gttctacgaa   7200
aaaaaaccgc agcacggatt ttatatgggg ttcctgttaa ataaaaaccg gacattagac   7260
cacgctccga taatcaaccg ctttgtggac aaaaaaacgg tggttttctt caccagttgg   7320
gcattgtctg atgaagcagg cataaatcat gtcttaagca gtctgaaaga tgaaggtttg   7380
aaatgtgtac tggtcacccc caccctcgac agcatccacg ttgaagaaaa tgtcatcaga   7440
acaccttacc ttaatatgga tagcatcaaa ggatgtctgt ttgccattca ccacggcggc   7500
atcggcacca gtgcccaact gcttaaaaac ggcatacctc agttaatcta cccaaaagcc   7560
tttgatcagt tcgaaaacgc aagctctctc gaaagaatag gctgtggcgt taaaggcggc   7620
gatataaatg cgttgaggca tatgattaaa aagtcggtta ccaatgataa taactgtgct   7680
ttttacgcct cgcggctaag tgaagagaac aaagaacgaa acgatgcgct ggaacgttta   7740
ctcatgggtt aagctcgagc acgcgagagt agggaactgc caggcatcaa ataaaacgaa   7800
aggctcagtc gaaagactgg gcctttcgtt ttatctgttg tttgtcggtg aacgctctcc   7860
tgagtaggac aaatccgccg ggagcggatt tgaacgatga taagctgtca aacatgagaa   7920
ttcttgaaga cgaaagggcc tcgtgtgtac aaacgttcgt caaaagggcg acacaaaatt   7980
cctgcagggg ccggcccagc gccggcggtc gagtggcgac ggcgcggctt gtccgcgccc   8040
tggtagattg cctggccgta ggccagccat ttttgagcgg ccagcggccg cgataggccg   8100
acgcgaagcg gcggggcgta gggagcgcag cgaccgaagg gtaggcgctt tttgcagctc   8160
ttcggctgtg cgctggccag acagttatgc acaggccagg cgggttttaa gagttttaat   8220
aagttttaaa gagttttagg cggaaaaatc gcctttttc tcttttatat cagtcactta   8280
catgtgtgac cggttcccaa tgtacggctt tgggttccca atgtacgggt tccggttccc   8340
aatgtacggc tttgggttcc caatgtacgt gctatccaca ggaaagagac cttttcgacc   8400
tttttcccct gctagggcaa tttgccctag catctgctcc gtacattagg aaccggcgga   8460
tgcttcgccc tcgatcaggt tgcggtagcg catgactagg atcgggccag cctgccccgc   8520
ctcctccttc aaatcgtact ccggcaggtc atttgacccg atcagcttgc gcacggtgaa   8580
acagaacttc ttgaactctc cggcgctgcc actgcgttcg tagatcgtct tgaacaacca   8640
tctggcttct gccttgcctg cggcgcggcg tgccaggcgg tagagaaaac ggccgatgcc   8700
gggatcgatc aaaaagtaat cggggtgaac cgtcagcacg tccgggttct tgccttctgt   8760
gatctcgcgg tacatccaat caactagctc gatctcgatg tactccggcc gcccggtttc   8820
gctctttacg atcttgtagc ggctaatcaa ggcttcaccc tcggataccg tcaccaggcg   8880
gccgttcttg gccttcttcg tacgctgcat ggcaacgtgc gtggtgttta accgaatgca   8940
ggtttctacc aggtcgtctt tctgctttcc gccatcggct cgccggcaga acttgagtac   9000
gtccgcaacg tgtggacgga acacgcggcc gggcttgtct cccttccctt cccggtatcg   9060
gttcatggat tcggttagat gggaaaccgc catcagtacc aggtcgtaat cccacacact   9120
ggccatgccg gccggccctg cggaaacctc tacgtgcccg tctggaagct cgtagcggat   9180
cacctcgcca gctcgtcggt cacgcttcga cagacggaaa acggccacgt ccatgatgct   9240
gcgactatcg cgggtgccca cgtcatagag catcggaacg aaaaaatctg gttgctcgtc   9300
gcccttgggc ggcttcctaa tcgacggcgc accggctgcc ggcggttgcc gggattcttt   9360
gcggattcga tcagcggccg cttgccacga ttcaccgggg cgtgcttctg cctcgatgcg   9420
ttgccgctgg gcggcctgcg cggccttcaa cttctccacc aggtcatcac ccagcgccgc   9480
```

-continued

```
gccgatttgt accgggccgg atggtttgcg accgctcacg ccgattcctc gggcttgggg    9540

gttccagtgc cattgcaggg ccggcagaca acccagccgc ttacgcctgg ccaaccgccc    9600

gttcctccac acatggggca ttccacggcg tcggtgcctg gttgttcttg attttccatg    9660

ccgcctcctt tagccgctaa aattcatcta ctcatttatt catttgctca tttactctgg    9720

tagctgcgcg atgtattcag atagcagctc ggtaatggtc ttgccttggc gtaccgcgta    9780

catcttcagc ttggtgtgat cctccgccgg caactgaaag ttgacccgct tcatggctgg    9840

cgtgtctgcc aggctggcca acgttgcagc cttgctgctg cgtgcgctcg gacggccggc    9900

acttagcgtg tttgtgcttt tgctcatttt ctctttacct cattaactca aatgagtttt    9960

gatttaattt cagcggccag cgcctggacc tcgcgggcag cgtcgccctc gggttctgat   10020

tcaagaacgg ttgtgccggc ggcggcagtg cctgggtagc tcacgcgctg cgtgatacgg   10080

gactcaagaa tgggcagctc gtacccggcc agcgcctcgg caacctcacc gccgatgcgc   10140

gtgcctttga tcgcccgcga cacgacaaag gccgcttgta gccttccatc cgtgacctca   10200

atgcgctgct taaccagctc caccaggtcg gcggtggccc atatgtcgta agggcttggc   10260

tgcaccggaa tcagcacgaa gtcggctgcc ttgatcgcgg acacagccaa gtccgccgcc   10320

tggggcgctc cgtcgatcac tacgaagtcg cgccggccga tggccttcac gtcgcggtca   10380

atcgtcgggc ggtcgatgcc gacaacggtt agcggttgat cttcccgcac ggccgcccaa   10440

tcgcgggcac tgccctgggg atcggaatcg actaacagaa catcggcccc ggcgagttgc   10500

agggcgcggg ctagatgggt tgcgatggtc gtcttgcctg acccgccttt ctggttaagt   10560

acagcgataa ccttcatgcg ttccccttgc gtatttgttt atttactcat cgcatcatat   10620

acgcagcgac cgcatgacgc aagctgtttt actcaaatac acatcacctt tttagacggc   10680

ggcgctcggt ttcttcagcg gccaagctgg ccggccaggc cgccagcttg gcatcagaca   10740

aaccggccag gatttcatgc agccgcacgg ttccggatga gcattca                 10787
```